United States Patent
Kozikowski et al.

(10) Patent No.: US 8,207,216 B2
(45) Date of Patent: Jun. 26, 2012

(54) BENZOFURAN-3-YL(INDOL-3-YL) MALEIMIDES AS POTENT GSK3 INHIBITORS

(75) Inventors: Alan P. Kozikowski, Chicago, IL (US); Irina Gaysina, Berwyn, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 88 days.

(21) Appl. No.: 12/488,433

(22) Filed: Jun. 19, 2009

(65) Prior Publication Data

US 2010/0004308 A1    Jan. 7, 2010

Related U.S. Application Data

(63) Continuation-in-part of application No. PCT/US2007/088248, filed on Dec. 19, 2007.

(60) Provisional application No. 60/870,825, filed on Dec. 19, 2006.

(51) Int. Cl.
  *A61K 31/404* (2006.01)
  *C07D 405/14* (2006.01)
  *C07D 209/56* (2006.01)
(52) U.S. Cl. ........ 514/414; 548/454; 548/430; 544/143; 514/235.2; 514/411
(58) Field of Classification Search ............... 514/235.2, 514/414, 411; 548/454, 430; 544/143
See application file for complete search history.

(56) References Cited

U.S. PATENT DOCUMENTS

| | | | |
|---|---|---|---|
| 5,057,614 A | 10/1991 | Davis et al. |
| 5,721,245 A | 2/1998 | Davis et al. |
| RE36,736 E | 6/2000 | Davis et al. |
| 6,417,185 B1 | 7/2002 | Goff et al. |
| 6,441,053 B1 | 8/2002 | Klein et al. |
| 6,479,490 B2 | 11/2002 | Gong et al. |
| 6,489,344 B1 | 12/2002 | Nuss et al. |
| 6,608,063 B2 | 8/2003 | Nuss et al. |
| 6,780,625 B2 | 8/2004 | Eldar-Finkelman |
| 6,800,632 B2 | 10/2004 | Nuss et al. |
| 6,890,931 B2 | 5/2005 | Beat et al. |
| 6,916,821 B2 | 7/2005 | Bear et al. |
| 6,949,547 B2 | 9/2005 | Nuss et al. |
| 6,977,262 B2 | 12/2005 | Kohara et al. |
| 6,989,382 B2 | 1/2006 | Wagman et al. |
| 7,037,918 B2 | 5/2006 | Nuss et al. |
| 7,045,519 B2 | 5/2006 | Nuss et al. |
| 7,125,878 B2 | 10/2006 | Zhang et al. |
| 2003/0176484 A1 | 9/2003 | Day-Lollini et al. |
| 2004/0052822 A1 | 3/2004 | Kohara et al. |
| 2004/0138273 A1 | 7/2004 | Wagman et al. |
| 2004/0210063 A1 | 10/2004 | Bowler et al. |
| 2005/0075276 A1 | 4/2005 | Rudd |
| 2005/0234120 A1 | 10/2005 | Heckel et al. |
| 2005/0288321 A1 | 12/2005 | Albaugh et al. |
| 2006/0089369 A1 | 4/2006 | Nuss et al. |
| 2006/0217368 A1 | 9/2006 | Morishita et al. |

FOREIGN PATENT DOCUMENTS

| | | |
|---|---|---|
| EP | 1 224 932 A1 | 7/2002 |
| WO | WO 99/65897 | 12/1999 |
| WO | WO 00/12497 | 3/2000 |
| WO | WO 00/38675 | 7/2000 |
| WO | WO 02/10158 | 2/2002 |
| WO | WO 02/46183 | 6/2002 |
| WO | WO 03/076398 | 9/2003 |
| WO | WO 2005/002552 | 1/2005 |
| WO | WO 2005/111018 | 11/2005 |
| WO | WO 2007/008514 | 1/2007 |
| WO | WO 2008/077138 | 6/2008 |

OTHER PUBLICATIONS

Ma et al. Chinese Journal of Chemistry 2001, 19(5), 489-492 (CAS Abstract and structures).*
Byrn et al., Chapter 11 Hydrates and Solvates in Solid-State Chemistry of Drugs (2nd Ed. 1999), 233-247.*
Morissette et al. Adv. Drug Delivery Rev. 2004, 56, 275-300.*
A.M. Rouhi, Chem. & Eng. News, Feb. 24, 2003, 81(8), 32-35.*
Gani et al. Natural Product Reports 2010, 27, 489-498.*

(Continued)

*Primary Examiner* — Jason M Nolan
(74) *Attorney, Agent, or Firm* — Greenlee Sullivan P.C.

(57) ABSTRACT

Compounds of formula:

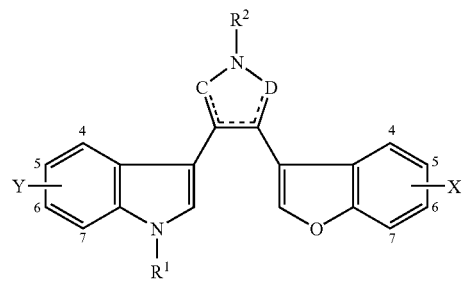

and pharmaceutically acceptable salts, esters and solvates thereof, where variables are defined in the specification, useful generally as inhibitors of protein kinases and particularly useful for inhibition of GSK-3.
Pharmaceutically compositions and medicaments containing a compound of the invention are provided. The invention provides methods of treatment of protein kinase-related disease, disorders or conditions. The invention provides methods of treatment of GSK-3-related diseases, disorders or conditions. More specifically, methods of treatment of bipolar disorder, including mania, schizophrenia, stroke, epilepsy, motor neuron disease, cranial or spinal trauma, neurodegenerative disorders, including multiple sclerosis (MS), Alzheimer's disease, Fragile X syndrome, autism, Huntington's disease, Parkinson's disease, amylotrophic lateral sclerosis (ALS), AIDS-associated dementia, diabetes, particularly type II diabetes, cardiomycete hypertrophy, reperfusion/ischemia, cancer, particularly colorectal cancer, pancreatic cancer, allergies and/or asthma and hair loss or baldness.

22 Claims, 2 Drawing Sheets

OTHER PUBLICATIONS

Schafer et al. Drug Discovery Today 2008, 13 (21/22), 913-916.*
Medicines in Development for Mental Illnesses 2010.*
Horig et al., Journal of Translational Medicine 2004, 2(44).*
Chen, W., Gaisina, I.N., Gunosewoyo, H., Malekiani, S.A., Hanania, T., Kozikowski, A.P. (Sep. 2011) "Structure-Guided Design of a Highly Selective Glycogen Synthase Kinase-3-beta Inhibitor: a Superior Neuroprotective Pyrazolone Showing Antimania Effects," ChemMedChem 6, 1587-1592 Wiley-VCH Verlag GmbH& Co. KGaA, Weinheim—published on-line Jul. 12, 2011.
Kozikowski, A.P., Gunosewoyo, H., Guo, S., Gaisina, I.N., Walter, R.L., Ketcherside, A., McClung, C.A., Mesecar, A., Caldarone, B. (Sep. 2011) "Identification of a Glycogen Synthase Kinase-3beta Inhibitor that Attenuates Hyperactivity in CLOCK Mutant Mice," ChemMedChem 6(9):1593-1602 Wiley-VCH Verlag GmbH& Co. KGaA, Weinheim—published on-line Jul. 5, 2011.
Kim, K. H., Gaisina, I., Gallier F., Holzle, D., Blond, S.Y., Mesecar, A., Kozikowski, A.P. (Dec. 2009) "Use of molecular modeling, docking, and 3D-QSAR studies for the determination of the binding mode of benzofuran-3-yl-(indol-3-yl)maleimides as GSK-3β inhibitors," J. Mol. Model 15:1463-1479 Springer-Verlag; published on line May 14, 2009.
Coghlan et al. (Sep. 7, 2000) "Selective Small Molecule Inhibitors of Glycogen Synthase Kinase-3 Modulate Glycogen Metabolism and Gene Transcription," *Chem. Biol.* 7:793-803.

Davis, P.D. et al. (1992) "Inhibitors of Protein Kinase C. 1. 2,3-bisarymaleimides," J. Medicinal Chem. 35:177-184.
Engler et al. (Jan. 2005) "The Development of Potent and Selective Bisarylmaleimide GSK3 Inhibitors," *Bioorg. Med. Chem. Lett.* 15:899-903.
Gaisina et al. (Web Release Mar. 16, 2009) "From a Natural Product Lead to the Identification of Potent and Selective Benzofuran-3-yl-(indol-3-yl)Maleimides as Glycogen Synthase Kinase 3β Inhibitors that Suppress Proliferation and Survival of Pancreatic Cancer Cells," *J. Med. Chem.* 52(7):1853-1863.
Extended Search Report for EP application 07865893.7, EP Regional Stage of PCT/US07/088248, Dated May 4, 2011.
International Search Report and Written Opinion, Corresponding to International Application No. PCT/US07/088248, Mailed Mar. 25, 2008.
Kozikowski et al. (Feb. 13, 2006) "Highly Potent and Specific GSK-3β Inhibitors that Block Tau Phosphorylation and Decrease α-Synuclein Protein Expression in a Cellular Model of Parkinson's Disease," *ChemMedChem* 1(2):256-266.
Kozikowski et al. (Web Release Jun. 7, 2007) "Structure-Based Design Leads to the Identification of Lithium Mimetics That Block Mania-Like Effects in Rodents. Possible New GSK-3β Therapies for Bipolar Disorders," *J. Am. Chem. Soc.*129(26):8328-8332.

* cited by examiner

BENZOFURAN-3-YL(INDOL-3-YL) MALEIMIDES AS POTENT GSK3 INHIBITORS

CROSS-REFERENCE TO RELATED APPLICATIONS

This application is a continuation-in-part of International application PCT/US2007/088248, filed Dec. 19, 2007 in English and which designates the United States and claims the benefit of U.S. provisional application 60/870,825, filed Dec. 19, 2006. Each of these applications is incorporated by reference in its entirety herein.

U.S. GOVERNMENT SUPPORT

This invention was made with United States government support through the National Institutes of Health under grant numbers R01 CA 101811 and R01 MH 079400. The United States government has certain rights in the invention.

BACKGROUND OF THE INVENTION

The search for new therapeutic agents has been greatly aided in recent years by better understanding of the structure of enzymes and other biomolecules associated with target diseases. One important class of enzymes that has been the subject of extensive study is the protein kinases.

Protein kinases mediate intracellular signal transduction. They do this by effecting a phosphorylation in response to extracellular and other stimuli to cause a variety of cellular responses to occur inside the cell. Examples of such stimuli include environmental and chemical stress signals (e.g. osmotic shock, heat shock, ultraviolet radiation, bacterial endotoxin, H2O2), cytokines (e.g. interleukin-1 (IL-1) and tumor necrosis factors (TNF-α)), and growth factors (e.g. granulocyte macrophage-colony-stimulating factor (GM-CSF), and fibroblast growth factor (FGF). An extracellular stimulus may effect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, central nervous system disorders, Alzheimer's disease or hormone-related diseases. Accordingly, there has been a substantial effort in medicinal chemistry to find protein kinase inhibitors that are effective as therapeutic agents.

Glycogen synthase kinase-3 (GSK-3) is a serine/threonine protein kinase comprised of α and β isoforms that are each encoded by distinct genes. Coghlan et al., Chemistry & Biology, 7,793-803 (2000); Kim and Kimmel, Curr. Opinion Genetics Dev., 10, 508-514(2000). GSK-3 has been implicated in various diseases including diabetes, CNS disorders such as manic depressive disorder, neurodegenerative diseases, such as Alzheimer's disease, and acute neuronal trauma (stroke and head trauma), cardiomyocete hypertrophy, and cancer. WO 99/65897; WO 00/38675; and Haq et al., J. Cell Biol. (2000) 151, 117. Inhibition of GSK-3 can also be useful in the treatment and prevention of disorders including Fragile X syndrome, autism, mental retardation, schizophrenia and Down's Syndrome. These diseases may be caused by, or result in, the abnormal operation of certain cell signaling pathways in which GSK-3 plays a role. GSK-3 has been found to phosphorylate and modulate the activity of a number of regulatory proteins. These proteins include glycogen synthase which is the rate limiting enzyme necessary for glycogen synthesis, the microtubule associated protein Tau, the gene transcription factor β-catenin, the translation initiation factor e1F2B, as well as ATP citrate lyase, axin, heat shock factor-1, c-Jun, c-Myc, c-Myb, CREB, and CEPBn. These diverse protein targets implicate GSK-3 in many aspects of cellular metabolism, proliferation, differentiation and development. (Meijer L. et al. (2004) "Pharmacological inhibitors or glycogen synthase kinase 3," Trends Pharmacol. Sci. 25(9):471-480 and Wagman A. et al. (2004) "Discovery and Development of GSK-3 Inhibitors for the Treatment of Type 2 Diabetes," Curr. Pharmaceutical Design, 10:1105-1137 provide recent reviews of GSK-3 inhibitors.)

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake. Klein et al., PNAS, 93, 8455-9 (1996); Cross et al., Biochem. J., 303, 21-26 (1994); Cohen, Biochem. Soc. Trans., 21, 555-567 (1993); Massillon et al., Biochem J. 299,123-128 (1994). However, in a diabetic patient where the insulin response is impaired, glycogen synthesis and glucose uptake fail to increase despite the presence of relatively high blood levels of insulin. This leads to abnormally high blood levels of glucose with acute and long term effects that may ultimately result in cardiovascular disease, renal failure and blindness. In such patients, the normal insulin-induced inhibition of GSK-3 fails to occur. It has also been reported that in patients with type 11 diabetes, GSK-3 is overexpressed. WO 00/38675. Therapeutic inhibitors of GSK-3 are therefore potentially useful for treating diabetic patients suffering from an impaired response to insulin.

GSK-3 activity has also been associated with Alzheimer's disease. Alzheimer's disease is among the most important health care problems in the world. The past decade has seen the adoption of the first class of medications, the cholinesterase inhibitors, effective in improving cognitive symptoms in Alzheimer's disease. These drugs provide symptomatic relief; effective disease-modifying therapy remains a major, elusive goal. Substantial efforts have been made to apply findings from laboratory research, as well as genetic and epidemiologic studies, to the identification of potential strategies for influencing Alzheimer's disease pathology. Alzheimer's disease is a progressive dementia which develops in late middle ages (45 to 65 years old) and its etiological changes are shrinkage of cerebral cortex due to a neuronal cell loss and degeneration of the neurons while, from the pathological view, many senile plaques and neurofibrillary tangles are noted in the brain. There is no pathologically substantial difference between the disease and senile dementia caused by the so-called natural aging which develops in the senile period of 65 years and older ages and, therefore, this disease is called senile dementia of Alzheimer type.

Alzheimer's disease is characterized by the well-known p-beta-amyloid peptide and the formation of intracellular neurofibrillary tangles. The neurofibrillary tangles contain hyperphosphorylated Tau protein, where Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells. Lovestone et al., Current Biology 4, 1077-86 (1994); Brownlees et al., Neuroreport, 8, 3251-55 (1997). Therefore, it is believed that GSK-3 activity may promote generation of the neurofibrillary tangles and the progression of Alzheimer's disease.

Another substrate of GSK-3 is β-catenin which is degraded after phosphorylation by GSK-3. Reduced levels of β-catenin have been reported in schizophrenic patients and have also been associated with other diseases related to increase in neuronal cell death. Zhong et al., Nature, 395, 698-702 (1998); Takashima et al., PNAS, 90, 7789-93 (1993); Pei et al., J. Neuropathol. Exp, 56, 70-78 (1997).

More than 2 million American adults, or about 1 percent of the population age 18 and older in any given year, have bipolar disorder (manic depressive disorder.) Current treatments include the so-called "mood stabilizers," lithium and valproic acid. Both are relatively dated drugs that are only partially effective and produce various undesirable side effects.

Efforts to understand the mechanism of action of lithium, have demonstrated that specific inhibitors of the enzyme glycogen synthase kinase-3β (GSK-3β) mimic the therapeutic action of mood stabilizers and therefore have potential for improved drugs for treating patients with bipolar disorder as well as certain neurodegenerative disorders. The pro-apoptotic properties of the GSK-3 enzyme also indicate a potential for such inhibitors as neuroprotective agents. Additionally, the neuroprotection function of such inhibitors may further contribute to their therapeutic efficacy of as mood disorder drugs. Certain inhibitors of GSK-3β have been shown to exert a neuroprotective action in vitro (Kozikowski, A. P.; Gaysina, I. N.; Petukhov, P. A.; Sridhar, J; King, L; Blond, S. Y.; Duka, T.; Rusnak, M.; Sidhu, A., ChemMedChem 2006, 1, (2), 256-266.) This work employed a cellular model of Parkinson's disease.

McBride, S. M. et al (2005) Pharmacological rescue of synaptic plasticity, courtship behavior and mushroom body defects in a *Drosophila* model of fragile X syndrome, Neuron 45:753-764 report that a *Drosophila* model of Fragile X can be treated with lithium or metabotropic glutamate receptor (MGluR) antagonists (see also: Raymond, F. L. and Tarpey P. (2006) The genetics of metal retardation. Human Molecular Genetics 15 (Review Issue No. 2) R110-R116). U.S. Pat. Nos. 6,916,821 and 6,890,931, report the use of Group I MGluR antagonists for the treatment and prevention of disorders, including Fragile X, autism, mental retardation, schizophrenia and Down's Syndrome. As well as for the treatment of epilepsy and anxiety in individuals having Fragile X syndrome, autism, mental retardation, schizophrenia and Down's Syndrome. As noted above, inhibitors of GSK-3β mimic the therapeutic action of lithium and as such are expected to be beneficial in the treatment of Fragile X syndrome and related disorders. Also GSK-3 is turned on by glutamate signaling indicating that antagonists of MGluR can affect GSK-3.

For many of the aforementioned diseases associated with abnormal GSK-3 activity, other protein kinases have also been targeted for treating the same diseases. However, the various protein kinases often act through different biological pathways. For example, certain quinazoline derivatives have been reported recently as inhibitors of p38 kinase. WO 00/12497. The compounds are reported to be useful for treating conditions characterized by enhanced p38 activity and/or enhanced TGF-β activity. While p38 activity has been implicated in a wide variety of diseases, including diabetes, p38 kinase is not reported to be a constituent of an insulin-signaling pathway that regulates glycogen synthesis or glucose uptake. Therefore, unlike GSK-3, p38 inhibition would not be expected to enhance glycogen synthesis and/or glucose uptake.

Because of the biological importance of GSK-3, there has been significant interest in therapeutically effective GSK-3 inhibitors. The following references relate to small molecule inhibitors of GSK-3 and their applications.

U.S. Pat. No. 6,441,053 reports inhibitors of GSK-3 and methods for identifying and using such inhibitors for the treatment of GSK-3 related disorders which are indicated to include bipolar disorder, including mania, Alzheimer's disease, diabetes, and leucopenia. The reference further indicates that GSK-3 inhibitors are useful in the treatment of disorders of conditions that respond to administration of lithium, GSK-3 inhibitors are also indicated to be useful for reducing the motility of mammalian spermatozoa.

WO 00/38675 (Smithkline Beecham) reports certain bisindole maleimides, indolyl aryl maleimides and indolocarbazoles as inhibitors of GSK-3β. Such inhibitors are indicated to be useful in the treatment of diabetes, chronic neurodegenerative conditions, manic depression, mood disorders, such as schizophrenia, neurotraumatic diseases, such as acute stroke, hair loss and cancer.

WO 02/10158 (Hoffman-LaRoche) and U.S. Pat. No. 6,479,490 report 3-indolyl-4-phenyl-1H-pyrrole-2,5-dione derivatives as inhibitors of GSK-3β. It is further reported that inhibition of GSK-3β activity reduces the level of CD4+ T-helper 2 cell (Th2). These cells produce cyctokines, promote IgE production and eosinophil differentiation. Th2-specific cytokines are important in the pathogenesis of allergies and asthma. This report indicates that inhibitors of GSK-3β are useful in the treatment of allergies and asthma.

WO 05/002552 (Astex Technology) reports certain compounds as inhibitors of cyclin dependent kinase, GSK-3 kinase and Aurora kinase. GSK-3 kinase is reported to be associated with embryonic development, protein synthesis, cell proliferation and differentiation, microtubule dynamics, cell motility, and cellular apoptosis. GSK-3 kinase is indicated to be implicated in diabetes, cancer, Alzheimer's disease, Huntington's disease, stroke, epilepsy, motor neuron diseases, and head trauma and as such inhibitors of GSK-3 kinase are useful in the treatment of such disease states. In particular, inhibitors of GSK-3 kinases are reported to be useful in treatment of cancer, particularly colorectal cancer, and in the treatment of disease or conditions characterized by neuronal apoptosis to limit and/or prevent neurodegeneration.

WO 05/111018 (Aventis) reports certain pyridazinone derivatives as inhibitors of GSK-3β. These inhibitors are reported to be useful in the treatment of neurodegenerative diseases (such as Alzheimer's disease, Parkinson's disease, frontoparietal dementia, corticobasal degeneration and Pick's disease), stroke, cranial and or spinal trauma, peripheral neuropathies, obesity, metabolic disease, type II diabetes, essential hypertension, atherosclerosis, cardiovascular diseases, polycystic ovary syndrome, syndrome X and immunodeficiency.

Published U.S. application U.S. 2006/0089369 (Chiron) reports certain pyrimidine or pyridine-based inhibitors of GSK-3 for treatment of disorders mediated by GSK-3 including diabetes, neurodegenerative disorders, including Alzheimer's disease, obesity, atherosclerotic cardiovascular disease, essential hypertension, polycystic ovary syndrome, syndrome X, ischemia, especially cerebral ischemia, traumatic brain injury, bipolar disorder, immunodeficiency and cancer. The reference states that agents that inhibit GSK-3 activity are useful in the treatment of disorders that are mediated by GSK-3 activity and that inhibition of GSK-3 mimics the activation of growth factor signaling pathways and consequently GSK3 inhibitors are useful in the treatment of diseases in which such pathways are insufficiently active.

Published U.S. application U.S. 2003/0176484 reports the use of inhibitors of GSK-3β in a mammal to promote bone formation, increase bone mineral density, reduce fracture rate, increase fracture healing rate, increase cancellous bone formation, increase new bone formation and to treat osteoporosis.

Published U.S. application U.S. 2006/0217368 reports GSK-3 inhibitors for nerve regeneration, and as agents for the promotion of neuropoiesis of neural stem cells. Drugs of the invention are reported to be useful as a therapeutic for neurological diseases such as Parkinson's disease, Alzheimer's disease, Down's disease, cerebrovascular disorder, cerebral stroke, spinal cord injury, Huntington's disease, multiple sclerosis, amyotrophic lateral sclerosis, epilepsy, anxiety disorder, schizophrenia, depression and manic depressive psychosis.

Published U.S. application 20050075276 reports the use of inhibitors of GSK-3α or β to augment CD28 dependent -T-cell responses. The invention is directed at least in part to a method of enhancing CD28 mediated and dependent T-cell responses against viral, bacterial, fungal or prion infections. Thus, inhibitors of GSK-3 are indicated to be useful in the treatment of viral, bacterial, fungal or prion infections.

U.S. Pat. Nos. 7,045,519, 7,037,918, 6,989,382, 6,977,262, 6,949,547, 6,800,632, 6,780,625, 6,608,063, 6,489,344, 6,479,490, and 6,417,185 relate to GSK-3 inhibitors. Published U.S. Patent applications U.S. 2005/0234120, 2004/0052822, 2004/0138273, and 2004/0210063 relate to GSK-3 inhibitors.

Inhibitors of GSK-3 have wide application as therapeutics and are in general important targets for pharmaceutical applications. A number of synthetic GSK-3 inhibitors have been reported, however, there remains a clear need for GSK-3 inhibitors that are potent, selective, safe, effective and which exhibit minimal undesired side-effects.

This invention relates at least in part to benzofuranyl derivatives of indolylmaleimides which are protein kinase inhibitors and particularly those which are GSK-3 inhibitors.

EP 1224932 relates to certain indolylmaleimides which are reported to be cell death inhibitors useful as pharmaceuticals or as a preservative for organs, tissues or cells. Compounds of formula:

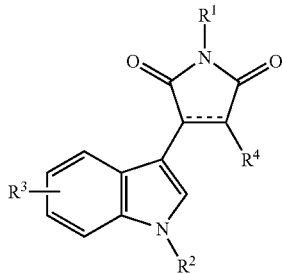

are reported, where the variables are defined in the patent application. Among many other groups, $R^4$ can be selected from an aryl group, other than 3-indolyl, which aryl group can be substituted. Compounds 18 and 19 in Table 1 of the reference have $R^4$ that is an unsubstituted benzofuranyl, with $R^2$ that is methyl and $R^1$ that is H (18) or methyl (19). No test data are listed in Table 2 of the reference for either of compounds 18 or 19. There is nothing in the reference that indicates that either of these compounds is a protein kinase inhibitor and nothing that indicates that either of these compounds is an inhibitor of GSK-3.

Engler T. A., et al "The development of potent and selective bisarylmaleimide GSK3 inhibitors," Bioorg. Med. Chem. Lett. (2005) Jan. 15:899-903 reports certain GSK3 inhibitors of formula:

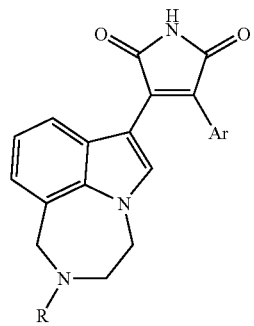

where Ar was certain bicyclic heteroaromatic groups. Ar was reported to include:

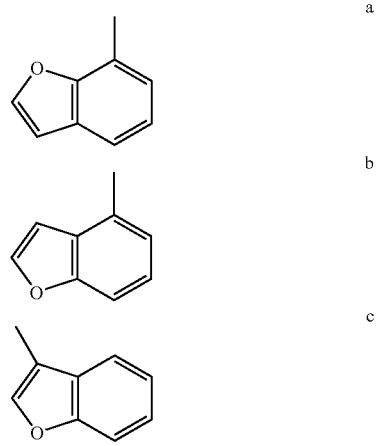

among a number of additional Ar groups, where a is a benzofuran-7-yl group, b is a benzofuran-4-yl group and c is a benzofuran-3-yl group. Certain compounds including compounds in which Ar is a or b are reported to be potent and selective GSK3 inhibitors. Data for selectivity of inhibition of GSK-3 compared to inhibition of CDK2, CDK4 and PKCβII kinases is reported. Data is reported for a single compound where Ar is c and where R is H. This compound is reported to have GSK3 IC50 of 64 nM with ratio of $IC_{50}$ of PKCβII/GSK3 of 37.

U.S. Pat. No. 5,721,245 (Davis) reports compounds of formula:

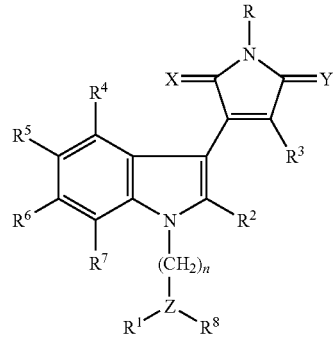

where among others X and Y are O, $R^1$ and $R^2$ taken together are a group of the formula —$(CH_2)_n$— or $R^1$ and $R^7$ taken together are a group of the formula —$(CH_2)_n$—, Z is N or CH, n is an integer from 1-5, m is an integer from 0 to 5 and $R^3$ is an aryl or aromatic heterocyclic group. Aromatic heterocyclic is defined as "a 5-membered or 6-membered heterocyclic aromatic group which can optionally carry a fused benzene ring" which can be substituted or unsubstituted. Exemplary heterocyclic groups are reported to be 2-thienyl, 3-thienyl, 3-benzothienyl, 3-benzofuranyl, 2-pyrrolyl, 3-indolyl and the like. Compounds are reported to be useful in the control or prevention of inflammatory, immunological, oncological, bronchopulmonary and cardiovascular disorders or in the treatment of asthma or AIDS. The compounds are further reported to be protein kinase inhibitors and as such inhibitors of cellular processes. The patent refers in particular to inhibition of protein kinase C.

WO 03/076398 and corresponding US 20050288321 report GSK-3 kinase inhibitors having the structure:

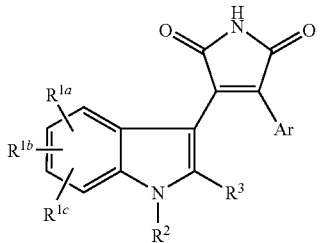

where Ar is benzofur-7-yl optionally substituted in the phenyl ring with $R^8$ and $R^9$, 1-($R^7$)-indol-4-yl, benzofur-4-yl, quinolin-5-yl, quinolin-7-yl, isoquinolin-5-yl, isoquinolin-3-yl, imidazo[1,2-a]pyridin-3-yl, imidazo[1,2-a]pyridin-5-yl, furo[3,2-c]pyridin-7-yl, benzo[1,3]dioxol-4-yl, 2,2-difluorobenzo[1,3]dioxol-4-yl, or 2,3-dihydrobenzofur-7-yl optionally substituted in the phenyl ring with $R^8$ and $R^9$ and in the dihydrofuryl ring with C1-C4 alkyl and $R^8$ is —$NHCO_2$ (C1-C4 alkyl), —$NHSO_2$(C1-C4 alkyl), halo, amino, —O— $(CH_2)_m$-G, —NH(O)(C1-C4 alkyl), C1-C4 alkoxy, hydroxyl, —O—R10, C1-C4 alkyl, C1-C4 alkylthio, or —$(CH_2)_m$-G and $R^9$ is halo, where G is hydroxyl, $NR^{11}R^{12}$ or piperidin-4-yl, $R^{11}$ and $R^{12}$ are independently selected from the group consisting of hydrogen, C1-C4 alkyl, cyclopropylmethyl, benzyl, or, taken together with the nitrogen to which they are attached form a piperidine, 4-hydroxypiperidine, 4-(C1-C4 alkyl)piperidine, N—($R^{13}$)-piperazine, or morpholine ring where $R^{13}$ is hydrogen, C(O)—(C1-C4 alkyl), or C1-C4 alkyl.

U.S. Pat. No. 5,057,614 (Davis) see also U.S. RE 36736 reports compounds of formula:

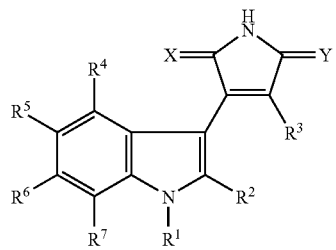

where $R^2$ is hydrogen among other groups, and $R^1$ is hydrogen, alkyl, aryl, araalkyl, hydroxyalkyl, and haloalkyl among other groups. These compounds are said to be inhibitors of protein kinase useful in the treatment of illnesses including inflammatory, immunological, bronchopulmonary and cardiovascular disorders where among others X and Y are O and $R^3$ is a carbocyclic or heterocyclic aromatic group. The $R^3$ heterocyclic aromatic group is reported to be a 5- or 6-membered heterocyclic aromatic group which can optionally carry a fused benzene ring and which can be unsubstituted or substituted, for example, with one or more, preferably one to three, substituents selected from halogen, alkyl, hydroxy, alkoxy, haloalkyl, nitro, amino, acylamino, mono- or dialkylamino, alkylthio, alkylsulphinyl and alkylsulphonyl. Examples of $R^3$ heterocyclic aromatic groups given in the patent are 2- or 3-thienyl, 3-benzothienyl, 1-methyl-2-pyrrolyl, 1-benzimidazolyl, 3-indolyl, 1- or 2-methyl-3-indolyl, 1-methoxymethyl-3-indolyl, 1-(1-methoxyethyl)-3-indolyl, 1-(2-hydroxypropyl)-3-indolyl, 1-(4-hydroxybutyl)-3-indolyl, 1-[I-(2-hydroxyethylthio)-ethyl]-3-indolyl, 1-[1-(2-mercaptoethylthio)ethyl]-3-indolyl, 1-(I-phenylthioethyl)-3-indolyl, I-[1-(carboxymethylthio)ethyl]-3-indolyl and 1-benzyl-3-indolyl.

SUMMARY OF THE INVENTION

The present invention provides compounds which are inhibitors of protein kinases and in particular are inhibitors of glycogen synthase kinase 3 (GSK-3).

The invention provides compounds of formula 1:

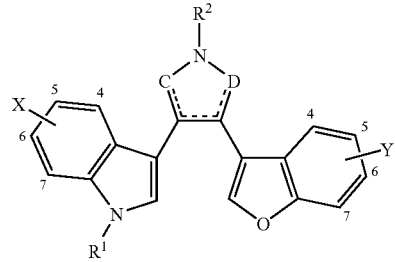

and pharmaceutically acceptable salts, esters and solvates (including hydrates) thereof,
where:
C and D are selected from the groups:

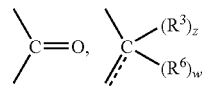

where w and z are 1 or 0, and w and z are not both 0; or

where doted lines in the central ring above and in the group indicate single or double bonds as appropriate to satisfy valency;

$R^1$ and $R^2$, independently of each other, are selected from H, alkyl, aryl, heterocyclic, arylalkyl, heteroaryl, heteroarylalkyl, alkoxyalkyl, aryloxyalkyl, aminoalkyl, thioalkyl, thioalkoxy, ether or thioether;

$R^3$ and $R^5$, independently of each other, are selected from H, alkyl, aryl, heterocyclic, arylalkyl, heteroaryl, heteroarylalkyl, alkoxyalkyl, aryloxyalkyl, aminoalkyl, thioalkyl, thioalkoxy, ether or thioether;

each $R^6$, independently of each $R^3$, can take all values of $R^3$ or is —$OR^4$, where $R^4$ is selected from H, alkyl, aryl, heterocyclic, arylalkyl, heteroaryl, heteroarylalkyl, alkoxyalkyl, aryloxyalkyl, aminoalkyl, thioalkyl, thioalkoxy, ether or thioether; and X and Y represent one, two, three or four non-hydrogen substituents on the indicated ring, wherein each X and Y substituent, independently of any other X or Y substituent, is selected from halogen, —OH, —CN, —NO$_2$, alkyl, alkenyl, alkynyl, aryl, alkoxyalkyl, thioalkoxylalkyl, ether, thioether, heterocyclic, heteroaryl, OR', —N(R)$_2$, —N(R)$_3$$^+$, —CO—N(R)$_2$, —NHCO—R, —NR'—CO—R, —NR—CO—N(R)$_2$, —CS—N(R)$_2$, —NHCSR, —NR'—CS—R, —NR—CS—N(R)$_2$, amidine, —COH, —CO—R', —CO$_2$H, —CO$_2$—, —CO$_2$R', —CS—R, —OCO—R, —SO$_2$N(R)$_2$, —NR—SO$_2$R, —SO$_2$—R, —SO—R, —SH and —SR; two X or two Y together can form a 5- to 8-member ring containing carbon and optionally containing one or two heteroatoms (i.e., O, N or S); X or Y or both may also be hydrogens; where R, independently of R', is selected from H, alkyl, alkenyl, alkynyl, aryl and arylalkyl groups and R', independent of R, is selected from alkyl, alkenyl, alkynyl, aryl or arylalkyl groups, with the exceptions that C and D cannot both be

C and D cannot both be

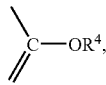

C and D cannot both be

and C and D cannot both be

The compound of formula 1 above comprises three distinct ring groups, the ring on the left is an optionally substituted indo-3-yl, the ring on the right is an optionally substituted benzofuran-3-yl ring and the central ring can be various different rings dependent upon the C and D groups.

In specific embodiments, C and D are not

In other embodiments, C and D are both

Ring numbering for X and Y substituents on the indolyl and benzofuranyl rings are as indicated in the above chemical formula. Additionally two X or two Y, substituted ortho to one another on the indicated ring, can together form a 5- to 8-member ring and particularly a 5- to 8-member ring between the points of attachment of the X's and Y's, which rings contain carbon and may contain one or two heteroatoms (e.g., O, N, or S). Additionally, one of $R^3$, $R^4$ or $R^5$ together with one of X or Y substituted at the 4-position on the indicated ring, can together form a 5 to 8-member ring containing carbon and optionally containing one or two heteroatoms. Additionally, $R^1$ together with one Y, can form a ring which contains carbon and may contain one or two heteroatoms (e.g., O, N, or S). There are a maximum of 4 X non-hydrogen substituents and a maximum of 4 Y non-hydrogen substituents.

All alkyl, alkenyl, alkynyl, aryl, arylalkyl, alkoxyalkyl, thioalkoxylalkyl, ether, thioether, heterocyclic, heteroaryl and heteroarylalkyl groups and any carbon atoms of any $R^1$, $R^2$, X, Y, R and R' of formula 1 are, unless otherwise specified, optionally substituted, wherein optional substitution is defined herein below and includes substitution with one or more halogens, —OH, —CN, alkyl, alkenyl, alkynyl, aryl, heterocyclic, heteroaryl, OR', —N(R)$_2$, —N(R)$_3$$^+$, —CO—N(R)$_2$, —NHCO—R, —NR'—CO—R, —NR—CO—N(R)$_2$, —CS—N(R)$_2$, —NHCSR, —NR'—CS—R, —NR—CS—N(R)$_2$, amidine, —COH, —CO—R', —CO$_2$H, —CO$_2$—, —CO$_2$R', —CS—R, —OCO—R, —SO$_2$N(R)$_2$, —NR—SO$_2$R, —SO$_2$—R, —SO—R, —SH or —SR. In specific embodiments R and R' groups of substituent groups are unsubstituted alkyl, alkenyl, alkynyl, aryl, heterocyclic, arylalkyl or heteroaryl groups. In other embodiments, alkyl, alkenyl, alkynyl, aryl, heterocyclic, arylalkyl or heteroaryl groups are substituted with one or more halogens, OH groups, CN groups and alkyl groups.

In specific embodiments, alkyl, alkenyl, alkynyl, aryl, aryllkyl, alkoxyalkyl, heterocyclic, heteroaryl and heteroarylalkyl groups of any $R^1$ and $R^2$ groups are unsubstituted. In specific embodiments, alkyl, alkenyl, alkynyl, aryl, arylalkyl, alkoxyalkyl, heterocyclic, heteroaryl and heteroarylalkyl groups of any X or Y groups are unsubstituted. In specific embodiments, one or more alkyl, alkenyl, alkynyl, aryl, arylalkyl, alkoxyalkyl, heterocyclic, heteroaryl and/or heteroarylalkyl groups of any $R^1$ and $R^2$ groups are substituted with one or more halogens. In specific embodiments, one or more alkyl, alkenyl, alkynyl, aryl, arylalkyl, alkoxyalkyl, heterocyclic, heteroaryl and/or heteroarylalkyl groups of any X or Y groups are substituted with one or more halogens.

In specific embodiments, one or more alkyl, alkenyl, alkynyl, aryl, arylalkyl, alkoxyalkyl, heterocyclic, heteroaryl and/or heteroarylalkyl groups of any $R^1$ and $R^2$ groups are substituted with one or more hydroxyl groups. In specific embodiments, one or more alkyl, alkenyl, alkynyl, aryl, arylalkyl, alkoxyalkyl, heterocyclic, heteroaryl and/or heteroarylalkyl groups of any X or Y groups are substituted with one or more hydroxyl groups.

In specific embodiments, one or more alkyl, alkenyl, alkynyl, aryl, arylalkyl, alkoxyalkyl, heterocyclic, heteroaryl and/or heteroarylalkyl groups of any $R^1$ and $R^2$ groups are substituted with one or more alkoxy groups. In specific embodiments, one or more alkyl, alkenyl, alkynyl, aryl, arylalkyl, alkoxyalkyl, heterocyclic, heteroaryl and/or heteroarylalkyl groups of any X or Y groups are substituted with one or more alkoxy groups. Alkoxy groups include those having 1-3 carbon atoms.

In specific embodiments, one or more alkyl, alkenyl, alkynyl, aryl, arylalkyl, alkoxyalkyl, heterocyclic, heteroaryl and/or heteroarylalkyl groups of any $R^1$ and $R^2$ groups are substituted with one or more carboxylate or carboxylate ester groups. In specific embodiments, one or more alkyl, alkenyl, alkynyl, aryl, arylalkyl, alkoxyalkyl, heterocyclic, heteroaryl and/or heteroarylalkyl groups of any X or Y groups are substituted with one or more carboxylate or carboxylate ester groups. Carboxylate ester groups include carboxylate alkyl esters, particularly those in which the ester alkyl group has 1-6 carbon atoms or 1-3 carbon atoms.

In specific embodiments, one or more of X or Y can be an alkyl group which is substituted with one or more halogens, one or more hydroxy groups, one or more alkoxy groups, one or more carboxylate groups or one or more carboxylate ester groups.

In specific embodiments, $R^1$ is a group other than an amine, $R^1$ is a group other than hydrogen or an alkyl having 1-3 carbon atoms, or $R^1$ is a group other than a group which links the nitrogen to which $R^1$ is attached to the a substituent on the indoyl ring (particularly the fused benzene ring of indoyl).

In specific embodiments, when C and D are both

$R^1$ is a group other than an amine.

In specific embodiments, when C and D are both

$R^1$ is a group other than hydrogen or an alkyl having 1-3 carbon atoms.

In specific embodiments, when C and D are both

$R^1$ is a group other than a group which links the nitrogen to which $R^1$ is attached to a substituent on the indoyl ring.

In specific embodiments, the benzofuran-3-yl ring of formula 1 is substituted with at least one non-hydrogen substituent.

In specific embodiments, the benzofuran-3-yl and the indo-3-yl rings of formula 1 are both substituted with at least one non-hydrogen substituent.

In specific embodiments, when C and D are both

the benzofuran-3-yl ring of formula 1 is substituted with at least one non-hydrogen substituent.

In specific embodiments, when C and D are both

the benzofuran-3-yl and the indo-3-yl rings are both substituted with at least one non-hydrogen substituent.

In specific embodiments of formula 1, the benzofuran-3-yl ring is not linked through one of its Y substituents to the central ring. In other specific embodiments of formula 1, the indo-3-yl ring is not linked through one of its X substituents to the central ring. In additional embodiments of formula 1, neither the indo-3-yl ring nor the benzofuran-3-yl ring is linked by any X or Y substituents to the central ring.

In specific embodiments:

C and D are both

one of C or D is

and the other is

one of C or D

is and the other is

or one of C or D is

and the other is

In specific embodiments, the central ring of the compound of formula 1 is selected from rings:

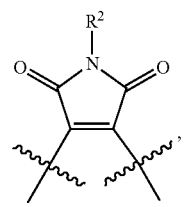

(A1)

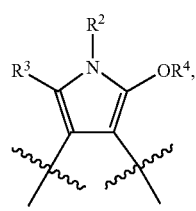

(A2a)

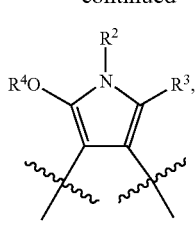

(A2b)

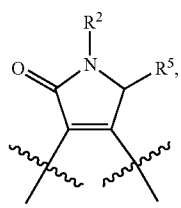

(A3a)

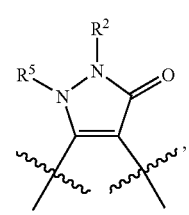

(A3b)

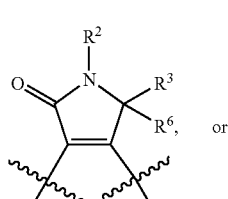

(A4a)

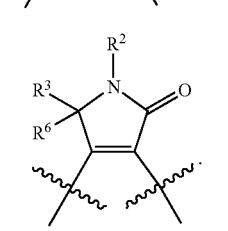

(A4b)

In specific embodiments of ring A1, $R^2$ is H, alkyl or aryl. In more specific embodiments of ring 1, $R^2$ is alkyl having 1-3 carbon atoms, H, a phenyl or a benzyl group. In specific embodiments of rings A2a and A2b, $R^4$ is alkyl, aryl or arylalkyl and $R^3$ is H, alkyl, aryl or arylalkyl In specific embodiments of rings A3a and A3b, $R^2$ is H, alkyl or aryl and $R^5$ is H, alkyl, aryl or arylalkyl. In specific embodiments of rings A4a or A4b, $R^2$ is H, alkyl or aryl, $R^3$ is H, alkyl or aryl and $R^6$ is independently of $R^3$ H, alkyl or aryl. In other embodiments, $R^2$ is H or alkyl, $R^3$ is H or alkyl, $R^6$ is H, alkyl or $OR^4$, $R^4$ is H or alkyl or $R^5$ is H or alkyl. In more specific embodiments of the above rings, $R^2$ is H or a methyl group.

In specific embodiments $R^1$ is H, alkyl, alkyl having 1-4 carbon atoms, aryl and heteroaryl. In other embodiments, $R^1$ is $-(CH_2)_n-N(R)_2$, where n is an integer from 1-6, $-(CH_2)_m-OH$, where m is an integer from 1-6 or $-(CH_2)_p-CO_2H$ where p is an integer from 1-6. In additional embodiments, $R^1$ is H, methyl, cyclopropyl, isopropyl, t-butyl or phenyl. In additional embodiments, $R^1$ is H an alkyl group, particularly an alkyl group having 1-6 carbon atoms, which is substituted with one or more halogens, particularly one or more fluorines, one or more $-OH$ groups or one or more $-N(R)_2$ groups. In additional embodiments, $R^1$ is $-CF_3$, $-CHF_2$, $-CH_2-CF_3$, or $-(CH_2)_n-OH$, where n is an integer from 1 to 6 In a specific embodiment, $R^1$ is methyl. In other specific embodiments, $R^1$ is $-(CH_2)_m-OH$, where m is an integer from 1-3.

In specific embodiments, $R^2$ is H, alkyl, alkyl having 1-4 carbon atoms, aryl or heteroaryl. In other embodiments, $R^2$ is H, methyl, isopropyl, t-butyl, or phenyl. In a specific embodiment $R^2$ is hydrogen.

In specific embodiments, $R^1$ is methyl and $R^2$ is hydrogen.

In specific embodiments, $R^3$ is hydrogen.

In specific embodiments, X represents one, two, three or four substituents independently selected from halogens, $-OH$, $-CN$, $-NO_2$, alkyl, alkenyl, alkynyl, aryl, heterocyclic, heteroaryl, $-OR'$, $-N(R)_2$, $-N(R)_3^+$, $-CO-N(R)_2$, $-NHCO(R)$, $-NR'-CO-R$, $-NR-CO-N(R)_2$, $-CO_2H$, $-CO_2-$, amidine, $-CO_2R'$, $-OCO-R$, $-SO_2N(R)_2$, $-N(R)_2SO_2-R$, $-SO_2-R$, $-SH$ or $-SR$, where R and R' are as defined above.

In other specific embodiments, X represents one non-hydrogen substituent as noted. In other specific embodiments, X represents two non-hydrogen substituents as noted. In additional specific embodiments, X represents one non-hydrogen substituent at the 4, 5, 6 or 7 position on the indolyl ring. In other specific embodiments, X represents a single non-hydrogen substituent at the 5 position of the indolyl ring. In additional specific embodiments, X represents two non-hydrogen substituents at two of the 4, 5, 6 or 7 positions on the indolyl ring. In additional embodiments, X represents two non-hydrogen substituents at the 5 and 6, the 5 and 7 or the 6 and 7 positions of the indolyl ring. In additional specific embodiments, X represents three non-hydrogen substituents at the 4, 5, 6 or 7 positions on the indolyl ring.

In specific embodiments, X is one or more halogens, $-OH$, alkyl, alkyl having 1-4 carbon atoms, cyclic alkyl, cyclic alkyl having 1-4 carbon atoms, alkenyl, alkenyl having 2 to 4 carbon atoms, alkynyl, alkynyl having 2-4 carbon atoms, $-C\equiv CH$, $-O$-alkyl, $-O$-Bn (Bn=$-CH_2$-phenyl), halogenated alkyl.

In additional specific embodiments, each X is selected independently from F, Br, Cl, I, methyl, ethyl, cyclopropyl, t-butyl, $-OCH_3$, $-O$-Bn, $-OH$, $-C\equiv CH$, $-CH_2-OH$, $-CN$, $-NO_2$, $-CO_2CH_3$, $-CONH_2$, $-SO_2NH_2$, $-NHCHO$, $-NHSO_2CH_3$, $-CF_3$, $-NHCO_2Et$, $-SO_2$-Ph (Ph=phenyl), $-NHCOPh$, or $-NHSO_2Ph$.

In more specific embodiments, X is one or more of $-F$, $-Br$, $-Cl$, $-O$-alkyl, $-OCH_3$, $-OBn$, $-OH$, $-C\equiv CH$, $-CF_3$, or cyclopropyl. In yet more specific embodiments, X is 5-F, 5-Br, 5-Cl, 5-I, 5-$OCH_3$, 5-CN, 5-OBn, 5-OH, 6-I, 6-Br, 6-Cl, 6-CN, 6-phenyl, 6-p-Cl-phenyl, 6-OBn, 6-OH, 7-Br, 7-OBn, 7-OH, 5-$C\equiv CH$, 5-cyclopropyl, 5-$C\equiv CH$-cyclopropyl, 5-morpholine, 6-$CH_3$, 7-$CH_2OH$, 7-$CH_2OCH_3$, 6-$CF_3$, 6-$S-CH_3$, 6-$S-CH_2CH_3$, 6-$CH=CH_2$, 6-$C\equiv CH$, 6-$CH_2F_2$, 7-$(CH_2)_2-OH$, and/or 7-$(CH_2)_2-CO_2H$.

In specific embodiments, X represents two substituents on the ring which together form a 5- or 6-member ring containing carbon and optionally containing one or two heteroatoms. In specific embodiments, X represents two substituents on the 5 and 6 positions which together form an alkylene or alkyleneoxy group which forms a 5-member ring fused to the ring upon which the X groups are bonded. In specific embodiments, X represents two substituents on the 5 and 6 positions which together form an alkylenedioxy group which forms a 5-member ring fused to the ring upon which the X groups are bonded. In specific embodiments, X represents two substituents on the 5 and 6 positions which together form a methylenedioxy group which forms a 5-member ring fused to the ring upon which the X groups are bonded. In specific embodiments, X represents two substituents on the 6 and 7 ring positions which together form a $(CH)_4$ moiety which forms a 6-member benzene ring fused to the ring upon which the X groups are bonded. In specific embodiments, X represents two substituents on the 5 and 6 ring positions which together form a $(CH)_4$ moiety which forms a 6-member benzene ring fused to the ring upon which the X groups are bonded.

In specific embodiments, X is one or more of a halogen, alkoxy, alkoxy- substituted alkyl, COOH-substituted alkyl, COO-alkyl-substituted alkyl, hydroxyl- substituted alkyl, fluorine-substituted alkyl, alkenyl, aryl or arylalkyl, arylalkyl-substituted amine, aryl-substituted amine, carboxamidine, acyloxy, heteroaryl, alkyl-substituted alkynyl, fluorine-substituted alkoxy, hydroxyl-substituted alkoxy, amine-substituted alkoxy, sulfonamide-substituted alkyl, alkyl or aryl-substituted urea, carboxy-substituted alkenyl, or a sulfonamide-substituted fluoroalkyl. In specific embodiments, X is one or more of a halogen, alkoxy, hydroxyl-substituted alkyl, fluorine-substituted alkyl, or aryl, arylakyl-substituted amine, aryl-substituted amine, carboxamidine, acyloxy, heteroaryl, alkyl-substituted alkynyl, sulfonamide-substituted alkyl, alkyl or aryl-substituted urea, or a sulfonamide-substituted fluoroalkyl. More specifically, X can be one of the listed groups substituted on any ring position. More specifically, X can be one of the listed groups substituted on the 5, 6 or 7 position of the indicated ring. In specific embodiments, two of X substituted on adjacent ring positions (ortho to each other) are joined to form a 5- or 6-member carbon ring in which one or two carbons are replaced with a heteroatom, which heteroatom can specifically be oxygen. In other specific embodiments, one of X is a halogen and a second X is one of the listed groups.

In additional embodiments, X is one or more of the substituents illustrated in Scheme 16.

In specific embodiments, Y represents one, two or three substituents independently selected from halogens, —OH, —CN, —NO$_2$, alkyl, alkenyl, alkynyl, aryl, alkoxyalkyl, thioalkoxylalkyl, ether, thioether, alkoxy-substituted alkyl, COOH-substituted alkyl, COO-alkyl-substituted alkyl, —OR', —N(R)$_2$, —N(R)$_3^+$, —CO—N(R)$_2$, —NHCO(R), —NR'—CO—R, —NR—CO—N(R)$_2$, —CO$_2$H, —CO$_2$—, amidine, —CO$_2$R', —OCO—R, —SO$_2$N(R)$_2$, —N(R)$_2$SO$_2$—R, —SO$_2$—R, —SH or —SR, where R and R' are as defined above. In other specific embodiments, Y represents one substituent as noted. In other specific embodiments, Y represents two substituents as noted. In additional specific embodiments, Y represents one substituent at the 4, 5, 6 or 7 position on the indolyl ring. In other specific embodiments, Y represents a single substituent at the 5 position of the indolyl ring. In additional specific embodiments, Y represents two substituents at two of the 4, 5, 6 or 7 positions on the indolyl ring. In additional embodiments, Y represents two substituents at the 5 and 6 or the 5 and 7 positions of the indolyl ring. In additional specific embodiments, Y represents three substituents at the 4, 5, 6 or 7 positions on the indolyl ring.

In specific embodiments, Y is one or more halogens, —OH, —CN, alkyl, alkyl having 1-4 carbon atoms, cyclic alkyl, cyclic alkyl having 1-4 carbon atoms, alkenyl, alkenyl having 2 to 4 carbon atoms, alkynyl, alkynyl having 2-4 carbon atoms, —C≡CH, phenyl, benzyl, —O-alkyl, —S-alkyl, —O-Bn (Bn=—CH$_2$-phenyl), —O-Bn-OCH$_3$, —(CH$_2$)$_q$—OR" (where R" is H or alkyl and q is an integer ranging from 1-6), —(CH$_2$)$_r$—CO$_2$H, where r is an integer from 1-6, —C≡C—R, halogenated alkyl. In specific embodiments, in which Y is an alkyl group having 1-4 carbon atoms, the alkyl group is optionally substituted with one or more hydroxyl groups, one or more alkoxy groups, one or more carboxylate (COOH) or caroxylate ester (—COO-alkyl) groups. In specific embodiments, two Y substitutes on different positions form a ring containing carbon and optionally containing one or two heteroatoms. In specific embodiments, two Y substituents at different sites together form a methylene dioxy group and form a five-member or six-member ring, In another specific embodiment, two Y substituents on adjacent sites form a six-member benzene ring.

In additional specific embodiments, each Y is selected independently from F, Br, Cl, I, methyl, ethyl, cyclopropyl, t-butyl, phenyl, halophenyl, —OCH$_3$, —O—CH$_2$-cyclopropyl, —O—CH$_2$-cyclobutyl, —O-Bn, —O-Bn-OCH$_3$, —OH, —SCH$_3$, —SCH$_2$CH$_3$, —C≡CH, —CH$_2$—C≡CH, —C≡CH-cyclopropyl, —CH$_2$—OH, —(CH$_2$)$_2$OH, —(CH$_2$)$_3$OH, —CH$_2$OCH$_3$, —CH═CHCO$_2$H, —CH$_2$CH$_2$CO$_2$H, —CH$_2$CH$_2$CO$_2$CH$_2$CH$_3$, —CN, —CO$_2$CH$_3$, —CONH$_2$, —SO$_2$NH$_2$, —NHCHO, —NHSO$_2$CH$_3$, —CF$_3$, —NHCO$_2$Et, —SO$_2$-Ph (Ph=phenyl), —NHCOPh, —NHSO$_2$Ph, and morpholine

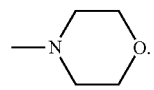

In more specific embodiments, Y is one or more halogens, —OH, —CH$_2$OR', or alkoxy (—OR') where R' is an alkyl group having 1-3 carbon atoms. In yet more specific embodiments, Y is 5-F, 6-F, 5-Br, 6-CH$_2$—OH, 6-CH$_2$OCH$_3$, 7-CH$_2$OCH$_3$, 6-O—CH$_2$-cyclopropyl, 6-O—CH$_2$-cyclobutyl, 6-O-(p-CH$_3$O)-Bn, 6-CH$_2$—C≡CH, 6-CH$_2$CH$_2$CO$_2$H, 6-OH, 6-OCH$_3$, 7-OCH$_3$, and/or 7-CH$_2$—CH$_2$—COCH$_2$CH$_3$.

In specific embodiments, Y is one or more of a halogen, alkoxy, hydoxyl-substituted alkyl, fluorine-substituted alkyl, alkenyl or aryl, arylalkyl-substituted amine, aryl-substituted amine, carboxamide, carboxamidine, acyloxy, heteroaryl, alkyl-substituted alkynyl, fluorine-substituted alkoxy, hydroxyl-substituted alkoxy, amino-substituted alkoxy, sulfonamide-substituted alkyl, alky-I or aryl-substituted urea, carboxy-substituted alkenyl, or a sulfonamido-substituted fluoroalkyl. In specific embodiments, Y is one or more of halogen, acetyloxy, carboxy-substituted alkenyl, alkoxy, substituted alkoxy, fluorine-substituted alkoxy, amine-substituted alkoxy, hydoxyl-substituted alkoxy. In specific embodiments, Y is two of the above listed substituents. In additional embodiments, one Y is a halogen and a second Y is one of the listed substituents. In specific embodiments, Y is one or more of the substituents illustrated in Scheme 16.

In specific embodiments, one of $R^4$ or $R^5$ and one X or Y substituent at position 4 of the ring to which the X or Y is bonded together form a linker between the rings to which the substituents are bonded. In specific embodiments, this linker is a carbon chain in which one or more carbon atoms can be substituted, particularly with one or more halogens, one or more OH groups or one or more NH$_2$ groups and/or in which the linker chain comprises one or more heteroatoms. The carbon chain may be saturated or it may contain one or more carbon-carbon double bonds. In particular embodiments, the linker is a —(CH$_2$)$_p$- chain where p is 1-10 and preferably 1-5 or 2-4. In other specific embodiments, this linker is an ether or thioether chain, e.g., a —(CH$_2$)$_p$-chain in which one or more —CH$_2$- groups are replaced with O or S, respectively, where p is 2-10 and preferably 2-5 or 3-6.

In specific embodiments, $R^5$ is selected from an unsubstituted alkyl group, an alkyl group substituted with one or more hydroxyls or halogens, or an ether or thioether group. In specific embodiments, $R^5$ is a methyl or ethyl group, or a hydroxyethyl, alkoxyethyl, methoxyethyl, fluoroalkyl, or 2,2,2-trifluoroethyl group.

In specific embodiments, the invention provides compounds of formula 1 above in which either or both of X or Y are one or more non-hydrogen substituents when $R^1$ is —$CH_3$ and $R^2$ is —H or —$CH_3$. In specific embodiments, the invention provides compounds of formula 1 above in which in specific embodiments, either or both of X or Y are one or more non-hydrogen substituents, when $R^1$ and $R^2$ are —H or —$CH_3$. In specific embodiments, the invention provides compounds of formula 1 above in which either or both of X or Y are one or more non-hydrogen substituents when $R^1$ and $R^2$ are —H or unsubstituted alkyl groups having 1-4 carbon atoms. In specific embodiments, the invention provides compounds of formula 1 above in which either or both of X or Y are one or more non-hydrogen substituents when $R^1$ and $R^2$ are —H or unsubstituted alkyl.

In a specific embodiment of formulas 2A and 2B, $X_4$ is an alkyl group substituted with an alkoxy, carboxylate or carboxylate ester group. In a specific embodiment of formulas 2A and 2B, $X_4$ is an alkyl group having 1-4 carbon atoms which is substituted with an alkoxy, carboxylate or carboxylate ester group. In a specific embodiment of formulas 2A and 2B, $X_4$ is an alkyl group having 1-4 carbon atoms which is substituted with one alkoxy, carboxylate or carboxylate ester group. In a specific embodiment of formulas 2A and 2B, $X_4$ is an alkyl group having 1-4 carbon atoms which is substituted with an alkoxy, carboxylate or carboxylate ester group, wherein the carboxylate ester group is an alkyl ester and the alkyl group of the ester has 1-6 carbon atoms. In a specific embodiment of formulas 2A and 2B where $X_4$ is an alkyl group substituted with and OH, alkoxy, carboxylate or carboxylate ester group, all Y substituents are hydrogens. In a specific embodiment of formulas 2A and 2B where $X_4$ is an alkyl group substituted with and OH, alkoxy, carboxylate or carboxylate ester group, at least one of $Y_2$-$Y_4$ is a halogen, or alkoxy group having 1-3 carbon atoms. In a specific embodiment of formulas 2A and 2B where $X_4$ is an alkyl group substituted with and OH, alkoxy, carboxylate or carboxylate ester group, at least one of $Y_2$ is a halogen, or $Y_4$ is an alkoxy group having 1-3 carbon atoms. In a specific embodiment of formulas 2A and 2B where $X_4$ is an alkyl group substituted with alkoxy, carboxylate or carboxylate ester group, at least two of $Y_2$-$Y_4$ are halogens. In specific embodiments, the alkyl group substituted with an OH, alkoxy, carboxylate or carboxylate ester group has 1 or 2 carbon atoms. In specific embodiments, $X_4$ is —$(CH_2)_n$—OH, —$(CH_2)_n$—O alkyl, —$(CH_2)_n$—$CO_2H$, or —$(CH_2)_n$—$CO_2$alkyl, where n is an integer ranging from 1-4. In specific embodiments $X_4$ is —$(CH_2)_n$—O alkyl or —$(CH_2)_n$—$CO_2$-alkyl where n is an integer ranging from 1-4 and the alkyl group has 1-6 or 1-3 carbon atoms.

In specific embodiments, $R^1$ is not, in combination with an X substituent at position 7 in the indoyl ring, a 6-, 7- or 8-member ring having carbon atoms and a nitrogen.

In other specific embodiments, particularly when all of Y are hydrogens, $R^1$ is not a —$(CH_2)_m$-Z($R^{11}$)($R^{12}$) group where Z is N or CH, m is an integer from 0 to 5 as reported in U.S. Pat. No. 5,721,245.

Certain of the compounds, salts, esters, solvates and prodrugs of this invention are useful as protein kinase inhibitors. In specific embodiments, compounds, salts, esters and solvates of this invention are useful as inhibitors of GSK-3. In more specific embodiments, compounds, salts, esters and solvates of this invention are useful as inhibitors of GSK 3-β.

GSK-3 inhibitors of this invention of formula 1 (and salts, esters, solvates and prodrugs thereof) are useful for the treatment of any diseases, conditions, symptoms or disorders associated with GSK-3 and particularly those associated with GSK-3β. In specific embodiments, compounds of this invention exhibiting Ki of <300 nM on either GSK-3 isoforms (α or β) are useful in treatment of any such diseases, conditions, symptoms or disorders. In additional specific embodiments, compounds of this invention exhibiting Ki of <25 nM on either GSK-3 isoforms (α or β) are useful in treatment of any such diseases, conditions, symptoms or disorders. In specific embodiments, compounds of this invention which inhibit hyperactivity produced by the combination of amphetamine/chlorodiazepoxide in a mouse model as described herein are particularly useful in the treatment of bipolar disorder and other mood disorders.

In preferred embodiments, GSK-3β inhibitors of this invention exhibit the ability to pass the brain-blood barrier as assessed in animal models. In a specific embodiment, a compound having this ability is compound 19 (Table 1).

Additional aspects of the invention are prodrugs of the compounds of this invention useful for treatment of disorders, conditions, and symptoms as described herein.

Other aspects of the present invention are pharmaceutical compositions comprising a compound of the present invention in combination with a pharmaceutically acceptable carrier wherein the compound is present in the composition in a therapeutically effective amount. In specific embodiments, the invention provides pharmaceutical compositions comprising a therapeutically effective amount of a compound of this invention which is a GSK-3 inhibitor in combination with a pharmaceutically acceptable carrier. In more specific embodiments, the invention provides pharmaceutical compositions comprising a therapeutically effective amount of a compound of this invention which is a GSK-3β inhibitor in combination with a pharmaceutically acceptable carrier.

In a more specific embodiment, the invention provides pharmaceutical compositions for treatment of bipolar disorder, including mania, or any of the symptoms or complications thereof, which comprises a therapeutically effective amount of a GSK-3 inhibitor of formula 1 or a pharmaceutically acceptable salt, ester, or solvate thereof, in combination with a pharmaceutically acceptable carrier.

In another more specific embodiment, the invention provides pharmaceutical compositions for treatment of schizophrenia, stroke, epilepsy, motor neuron disease, cranial or spinal trauma, or any of the symptoms or complications thereof, which comprises a therapeutically effective amount of a GSK-3 inhibitor of formula 1 or a pharmaceutically acceptable salt, ester, or solvate thereof, in combination with a pharmaceutically acceptable carrier.

In a more specific embodiment, the invention provides pharmaceutical compositions for treatment of neurodegenerative disorders, including multiple sclerosis (MS), Alzheimer's disease, Parkinson's disease, amylotrophic lateral sclerosis (ALS), AIDS-associated dementia, or any of the symptoms or complications thereof, which comprises a therapeutically effective amount of a GSK-3 inhibitor of formula 1 or a pharmaceutically acceptable salt, ester, or solvate thereof, in combination with a pharmaceutically acceptable carrier.

In a more specific embodiment, the invention provides pharmaceutical compositions for treatment of diabetes, particularly type II diabetes or any of the symptoms or complications thereof, which comprises a therapeutically effective amount of a GSK-3 inhibitor of formula 1 or a pharmaceutically acceptable salt, ester, or solvate thereof, in combination with a pharmaceutically acceptable carrier.

In another more specific embodiment, the invention provides pharmaceutical compositions for treatment of cardiomycete hypertrophy, reperfusion/ischemia or any of the symptoms or complications thereof, which comprises a therapeutically effective amount of a GSK-3 inhibitor of formula 1 or a pharmaceutically acceptable salt, ester, or solvate thereof, in combination with a pharmaceutically acceptable carrier.

In another more specific embodiment, the invention provides pharmaceutical compositions for treatment of cancer, particularly colorectal cancer or any of the symptoms or complications thereof, which comprises a therapeutically effective amount of a GSK-3 inhibitor of formula 1 or a pharmaceutically acceptable salt, ester, or solvate thereof, in combination with a pharmaceutically acceptable carrier. In another specific embodiment, the invention provides pharmaceutical compositions for treatment of pancreatic cancer or for the treatment of ovarian cancer which comprises a therapeutically effective amount of a compound of formula 2A or 2B or a pharmaceutically acceptable salt, ester, or solvate thereof, in combination with a pharmaceutically acceptable carrier.

In another more specific embodiment, the invention provides pharmaceutical compositions for treatment of allergies and/or asthma or any of the symptoms or complications thereof, which comprises a therapeutically effective amount of a GSK-3 inhibitor of formula 1 or a pharmaceutically acceptable salt, ester, or solvate thereof, in combination with a pharmaceutically acceptable carrier.

In another more specific embodiment, the invention provides pharmaceutical compositions for treatment of hair loss or baldness which comprises a therapeutically effective amount of a GSK-3 inhibitor of formula 1 or a pharmaceutically acceptable salt, ester, or solvate thereof, in combination with a pharmaceutically acceptable carrier.

Also included in the invention is a method of treating a GSK-3-related disorder, particularly a GSK-3β disorder, in an animal comprising administering to the animal a therapeutically effective amount of a GSK-3 (or more specifically a GSK-3β) inhibitor in a pharmaceutically acceptable carrier. Preferably, the animal is a mammal, and more preferably, the mammal is a human. More specifically the invention provides a method for treatment of bipolar disorder in which a therapeutically effect amount of a GSK-3 inhibitor of this invention is administered to an individual in need of such treatment. More specifically the invention provides a method for treatment of type II diabetes in which a therapeutically effect amount of a GSK-3 inhibitor of this invention is administered to an individual in need of such treatment. More specifically the invention provides a method for treatment of cancer in which a therapeutically effect amount of a GSK-3 inhibitor of this invention is administered to an individual in need of such treatment.

The invention further provides medicaments comprising a compound of formula 1 or a pharmaceutically acceptable salt, ester or solvate thereof for use in treatment of a GSK-3-related or a GSK-3β-related disease, disorder or condition. Medicaments can further comprise a pharmaceutically acceptable carrier. The invention additional relates to methods for the preparation of such medicaments for the treatment of a GSK-3-related or a GSK-3β-related disease, disorder or condition. The invention additionally relates to the use of a GSK-3 inhibitor of formula 1 or pharmaceutically acceptable salt, ester of solvate thereof for the preparation of a medicament for the treatment of a GSK-3-related or a GSK-3β-related disease.

The invention further provides medicaments comprising a compound of formula 2 or a pharmaceutically acceptable salt, ester or solvate thereof for use in treatment of cancer, including colorectal cancer, pancreatic cancer and/or ovarian cancer. Medicaments can further comprise a pharmaceutically acceptable carrier. The invention additional relates to methods for the preparation of such medicaments. The invention additionally relates to the use of a compound of formula 2 or pharmaceutically acceptable salt, ester of solvate thereof for the preparation of a medicament for the treatment of cancer, particularly colorectal cancer, pancreatic cancer and/or ovarian cancer.

Additional aspects of the invention will be apparent on review of the description herein including the figures and the specific examples.

DETAILED DESCRIPTION OF THE INVENTION

Figure 1A:
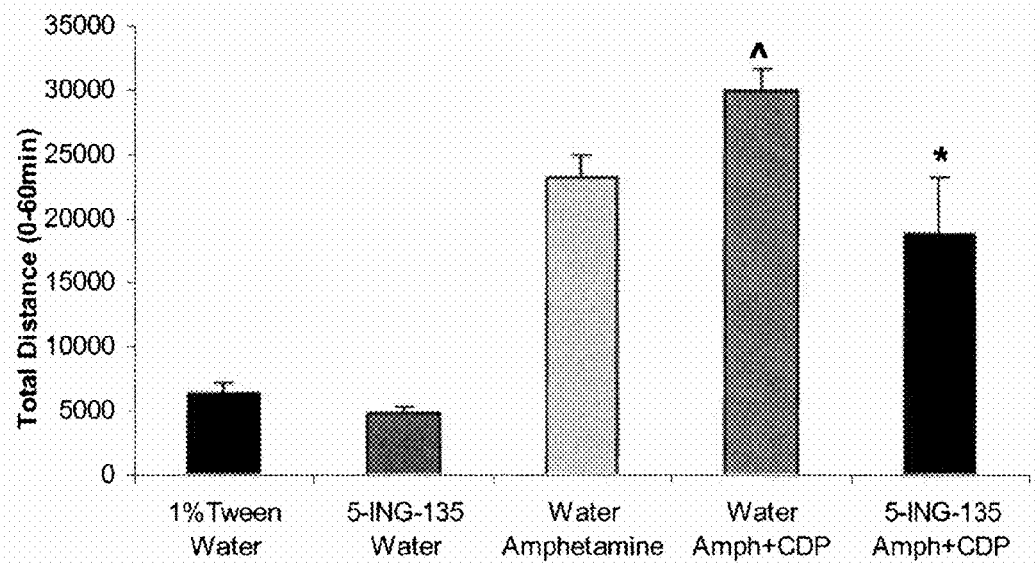
FIG. 1A is a graph illustrating inhibition of chlorodiazepoxide (CDP) and amphetamine-induced hyperactivity in C57BL/6J mice by GSK-3β inhibitor 5-ING-135 as assessed by locomotor activity which is measured by total distance from 0 to 60 minutes. Control treatments are as indicated.

This invention relates to benzofuranyl-indolyl maleimides and related molecules which are protein kinase inhibitors. Certain of the compounds of this invention are inhibitors of GSK-3. Certain compounds of this invention exhibit $K_i$ values of less than 23 nM as measured against GSK-3β (see Table 2). Certain compounds of this invention exhibit $K_i$ values of 4 nM or lower as measured against GSK-3β. Certain compounds of this invention exhibit $K_i$ values as low as 0.4 nM as measured against GSK-3β. Certain compounds of the invention were assessed for utility for the treatment of bipolar disorder employing a hyperactivity model of mania in mice. Certain compounds of the invention exhibit selectivity of inhibition of GSK-3 compared to other protein kinases, such as those protein kinases listed in Table 3.

Certain compounds of this invention exhibit inhibition with $IC_{50}$ values in antiproliferation assays employing pancreatic cancer cell lines of less than 25 microM. Certain compounds of this invention exhibit inhibition with $IC_{50}$ values in antiproliferation assays employing pancreatic cancer cell lines of less than 10 microM or less or 1 microM or less.

Details of this invention have been described in Kozikowski et al. (2007) J. Amer. Chem. Soc. 129 (26) 8328-8332; and Gaisina, I. N., et al. (2009) J. Med. Chemistry 52(7)1853-1863, each of which is incorporated by reference herein.

The invention relates generally to compounds of formula 1 above and to compounds of other formulas herein as well as to pharmaceutical compositions comprising one or more of the compounds of the formulas herein for various applications as described herein.

Definitions of terms used in this application are provided herein below.

The term "protein kinase" is used generically herein to refer to any protein kinase expressed in mammalian tissue. The phrase "protein kinase-related" in reference to diseases, disorders, conditions etc. refers to any disorders, conditions or diseases that are mediated, caused, enhanced or exacerbated by a protein kinase. A number of protein kinases are known in the art. Of particular interest with respect to the compounds of this invention are cyclin-dependent kinases (e.g., CDK-2, CDK-5, etc.) and protein kinase C (PKC). Additional protein kinases are listed in Table 3. Disease, disorders or conditions that are protein kinase-related include autoimmune diseases, inflammatory diseases, neurological and neurodegenerative diseases, cancer, cardiovascular diseases, allergies and asthma, Alzheimer's disease or hormone-related diseases.

GSK-3 is used herein as it is most generally used in the art to refer to all isoforms of glycogen synthase kinase-3 which are expressed in mammalian tissue. Currently, two isoforms ($\alpha$ and $\beta$) of GSK-3 are known. A third form of GSK-3 designed GSK-3$\beta$2 which is a splicing variant of GSK-3$\beta$ has been reported. The two isoforms appear to have independent regulatory roles, because GSK-3$\alpha$ cannot fully compensate for GSK-3$\beta$ deficiency, as demonstrated by the fact that GSK-3 knockouts are lethal in mice. While differences in gene expression and protein levels of the isoforms have been observed, no difference in biological function and substrate affinity have been reported for the isoforms.

The term "selectivity" is used herein in reference to inhibition of protein kinases by small molecules, particularly those of this invention. In general, an inhibitor of one protein kinase may also inhibit one or more other protein kinases. Because the different protein kinases exhibit effects in a variety of biological processes, it will generally be preferred when wishing to inhibit a target protein kinase to employ those inhibitors which selectively inhibit the target protein kinase. While absolute selectivity is not necessarily required, for therapeutic applications it is desirable to avoid undesired side-effects and thus to avoid ancillary inhibition of protein kinases other than the target protein kinases. Inhibitors preferred for use in therapeutic application are those which exhibit effective inhibition of the target and minimal inhibition of protein kinases the inhibition of which will be detrimental. Because a disease, disorder or condition may have a complex etiology which is mediated by more than one protein kinase, protein kinase inhibitors which inhibit multiple protein kinases may in some cases provide additional therapeutic benefit.

As used herein the phrase "GSK-3-related", including "GSK-3$\beta$-related", in reference to diseases, conditions or disorders are those that are mediated, caused, enhanced or exacerbated by GSK-3 ($\alpha$ or $\beta$) or more specifically GSK-3$\beta$. GSK-3 and GSK-3$\beta$-related disorders include metabolic disorders and diseases, including type II diabetes, disorders or conditions of the central nervous system, including bipolar disorder, depression, manic depressive psychosis, mood disorders, mania, anxiety disorder, schizophrenia, neurodegenerative disorders or diseases, including Alzheimer's disease, Parkinson's disease, frontoparietal dementia, corticobasal degeneration, Pick's disease, Down's disease, multiple sclerosis, X, immunodeficiency, osteoporosis, bone-loss, fractures, leucopenia, Huntington's disease, amyotrophic lateral sclerosis, motor neuron diseases, neurotraumaic diseases, such as cranial or spinal trauma, stroke, ischemia, especially cerebral ischemia, epilepsy, diseases associated with abnormal cell proliferation, such as cancer and particularly colorectal cancer, pancreatic cancer and ovarian cancer, allergies and asthma, disorders or diseases associated with high levels of TH2 cells, peripheral neuropathies, obesity, essential hypertension, atherosclerosis, cardiovascular diseases, polycystic ovary syndrome, syndrome X, and viral, bacterial, fungal or prion infections. GSK-3 inhibitors can also be used to promotion of bone formation, increase bone mineral density, reduce fracture rate, increase fracture healing rate, increase cancellous bone formation, and increase new bone formation. Additionally, inhibition of GSK3 mimics the activation of growth factor signaling pathways and consequently GSK3 inhibitors are useful in the treatment of diseases in which such pathways are insufficiently active. GSK-3 inhibitors are also indicated to be useful for reducing the motility of mammalian spermatozoa.

In specific embodiments, inhibitors of GSK-3$\beta$ of this invention are useful in the treatment of bipolar disorder and related conditions or disorders or the symptoms thereof. In other specific embodiments, inhibitors of GSK-3$\beta$ of this invention are useful in the treatment of type II diabetes. In other specific embodiments, inhibitors of GSK-3$\beta$ of this invention are useful in the treatment of Alzheimer's disease. In additional specific embodiments, inhibitors of GSK-3$\beta$ of this invention are useful in the treatment of cancer, particularly colorectal cancer and pancreatic cancer.

Compounds of the invention include those of formulas 2A and 2B:

Formula 2A

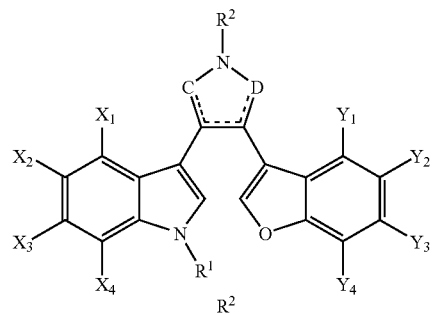

Formula 2B

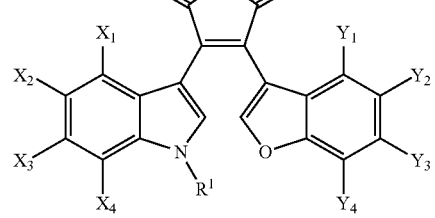

and pharmaceutically acceptable salts esters and solvates thereof wherein:

Variables C and D for formula 2A are as defined for formula 1, above;

$R^1$ and $R^2$, independently of one another, are selected from H or alkyl, particularly alkyl groups having 1-3 carbon atoms;

$X_1$ and $Y_1$ are both hydrogens;

$X_2$, $X_3$ and $X_4$ are selected from hydrogen, halogen, trifluoromethyl, alkoxy or two of $X_2$, $X_3$ or $X_4$ together form a six-member alkyl, alkenyl or aromatic ring in which one or two CH or CH$_2$ groups are optionally replaced with oxygen; and $Y_2$, $Y_3$ and $Y_4$, are selected from hydrogen, halogen, or alkoxy groups, wherein at least two of $X_2$-$X_4$ are groups other than hydrogen except that when $Y_4$ is an alkoxy group, at least one of $X_2$-$X_4$ is a group other than hydrogen and wherein at least one of $Y_2$-$Y_4$ is a group other than hydrogen except that when two of $X_2$, $X_3$ and $X_4$ are halogens $Y_2$-$Y_4$ can all be hydrogens.

In additional embodiments of formula 2A or 2B, two of $X_2$-$X_4$ are halogens or trifluoromethyl groups. In additional embodiments of formula 2A or 2B, two of $X_2$-$X_4$ are halogens or trifluoromethyl groups and one of $Y_2$-$Y_4$ is a halogen or alkoxy group having 1-3 carbon atoms. In more specific embodiments of formula 2A or 2B, two of $X_2$-$X_4$ are halogens. In more specific embodiments of formula 2A or 2B, two of $X_2$-$X_4$ are halogens and one of $Y_2$-$Y_4$ is a halogen or alkoxy group having 1-3 carbon atoms. In more specific embodiments of formula 2A or 2B, $X_2$ and $X_3$ are halogens. In more specific embodiments of formula 2A or 2B, $X_3$ and $X_4$ are halogens. In more specific embodiments of formula 2A or 2B, $X_2$ and $X_3$ are halogens, $Y_4$ is an alkoxy group having 1-3 carbon atoms and $Y_2$ and $Y_3$ are hydrogens or halogens. In more specific embodiments of formula 2, $X_3$ and $X_4$ are halogens, $Y_4$ is an alkoxy group having 1-3 carbon atoms and $Y_2$ and $Y_3$ are hydrogens or halogens.

In additional embodiments of formula 2A or 2B, two of $Y_2$-$Y_4$ are halogens or alkoxy groups having 1-3 carbon atoms. In additional embodiments of formula 2A or 2B, $Y_2$ and $Y_3$ are halogens. In additional embodiments of formula 2A or 2B, $Y_4$ is an alkoxy group having 1-3 carbon atoms. In more specific embodiments of formula 2A or 2B, two of $Y_2$-$Y_4$ are halogens or alkoxy groups having 1-3 carbon atoms and at least one of $X_2$-$X_4$ is a halogen or trifluormethyl group. In more specific embodiments of formula 2A or 2B, two of $Y_2$-$Y_4$ are halogens or alkoxy groups having 1-3 carbon atoms and at least one of $X_2$-$X_4$ is a halogen. In more specific embodiments of formula 2A or 2B, two of $Y_2$-$Y_4$ are halogens or alkoxy groups having 1-3 carbon atoms and at least one of $X_2$-$X_4$ is a trifluoromethyl group. In more specific embodiments of formula 2A or 2B, two of $Y_2$-$Y_4$ are halogens or alkoxy groups having 1-3 carbon atoms and two of $X_2$-$X_4$ are halogens or trifluoromethyl groups. In more specific embodiments of formula 2A or 2B, two of $Y_2$-$Y_4$ are halogens and two of $X_2$-$X_4$ are halogens or trifluoromethyl groups. In more specific embodiments of formula 2A or 2B, two of $Y_2$-$Y_4$ are halogens and $X_2$ and $X_3$ are halogens or trifluoromethyl groups. In more specific embodiments of formula 2A or 2B, two of $Y_2$-$Y_4$ are halogens and $X_3$ and $X_4$ are halogens. In more specific embodiments of formula 2A or 2B, two of $Y_2$-$Y_4$ are halogens and two of $X_2$-$X_4$ together form an alkyleneoxy group. In more specific embodiments of formula 2A or 2B, two of $Y_2$-$Y_4$ are halogens and two of $X_2$-$X_4$ together form an alkylenedioxy group. In more specific embodiments of formula 2A or 2B, two of $Y_2$-$Y_4$ are halogens and two of $X_2$-$X_4$ together form a methyleneoxy group. In more specific embodiments of formula 2A or 2B, two of $Y_2$-$Y_4$ are halogens and $X_2$ and $X_3$ together form an alkyleneoxy group. In more specific embodiments of formula 2A or 2B, two of $Y_2$-$Y_4$ are halogens and $X_2$ and $X_3$ together form an alkylenedioxy group. In more specific embodiments of formula 2A or 2B, two of $Y_2$-$Y_4$ are halogens and $X_2$ and $X_3$ together form a methyleneoxy group. In more specific embodiments of formula 2A or 2B, two of $Y_2$-$Y_4$ are halogens and two of $X_2$-$X_4$ together form a 1-H benzo group. In more specific embodiments of formula 2A or 2B, two of $Y_2$-$Y_4$ are halogens and $X_2$ and $X_3$ together form a 1-H benzo group fused to the. In more specific embodiments of formula 2A or 2B, two of $Y_2$-$Y_4$ are halogens and $X_3$ and $X_4$ together form a 1-H benzo group. In more specific embodiments of formula 2A or 2B, $Y_2$ and $Y_3$ are halogens and $X_2$ and $X_3$ together form a 1-H benzo group. In more specific embodiments of formula 2A or 2B, $Y_2$ and $Y_3$ are halogens and $X_3$ and $X_4$ together form a 1-H benzo group. In specific embodiments, $Y_2$ and $Y_3$ are both fluorines. In specific embodiments of formula 2A or 2B, $Y_2$ is fluorine.

In additional embodiments of formula 2A or 2B, $Y_4$ is an alkoxy group having 1-3 carbon atoms. In additional embodiments of formula 2A or 2B, $Y_4$ is a methoxy group. In more specific embodiments of formula 2A or 2B, $Y_4$ is an alkoxy group having 1-3 carbon atoms and at least one of $X_2$-$X_4$ is a halogen or trifluoromethyl group. In more specific embodiments of formula 2A or 2B, $Y_4$ is a methyoxy group and at least one of $X_2$-$X_4$ is a halogen or trifluoromethyl group. In more specific embodiments of formula 2A or 2B, $Y_4$ is an alkoxy group having 1-3 carbon atoms and two of $X_2$-$X_4$ are halogens or trifluoromethyl groups. In more specific embodiments of formula 2A or 2B, $Y_4$ is a methyoxy group and at least two of $X_2$-$X_4$ are halogens or trifluoromethyl groups. In more specific embodiments of formula 2A or 2B, $Y_4$ is an alkoxy group having 1-3 carbon atoms and $X_2$ is a trifluoromethyl group. In more specific embodiments of formula 2A or 2B, $Y_4$ is a methyoxy group and $X_2$ is a trifluoromethyl group. In more specific embodiments of formula 2A or 2B, $Y_4$ is an alkoxy group having 1-3 carbon atoms and $X_2$ is a halogen. In more specific embodiments of formula 2A or 2B, $Y_4$ is a methyoxy group and $X_2$ is a halogen. In more specific embodiments of formula 2A or 2B, $Y_4$ is an alkoxy group having 1-3 carbon atoms and $X_2$ and $X_3$ are both halogens. In more specific embodiments of formula 2A or 2B, $Y_4$ is a methyoxy group and $X_2$ and $X_3$ are both halogens. In more specific embodiments of formula 2A or 2B, $Y_4$ is an alkoxy group having 1-3 carbon atoms and $X_2$ and $X_3$ together form an alkyleneoxy group. In more specific embodiments of formula 2A or 2B, $Y_4$ is a methoxy group and $X_2$ and $X_3$ together form an alkyleneoxy group. In more specific embodiments of formula 2A or 2B, $Y_4$ is an alkoxy group having 1-3 carbon atoms and $X_2$ and $X_3$ together form an alkylenedioxy group. In more specific embodiments of formula 2A or 2B, $Y_4$ is a methoxy group and $X_2$ and $X_3$ together form an alkylenedioxy group. In more specific embodiments of formula 2A or 2B, $Y_4$ is an alkoxy group having 1-3 carbon atoms and $X_2$ and $X_3$ together form an methylenedioxy group. In more specific embodiments of formula 2A or 2B, $Y_4$ is a methoxy group and $X_2$ and $X_3$ together form a methylenedioxy group. In further embodiments of formula 2A or 2B, $Y_2$ and $Y_3$ are hydrogens and $Y_4$ is an alkoxy group having 1-3 carbon atoms. In further embodiments of formula 2A or 2B, $Y_2$ and $Y_3$ are hydrogens and $Y_4$ is a methoxy group.

In additional embodiments of formula 2A or 2B, one of $X_2$-$X_4$ is a halogen or trifluoromethyl group, $Y_4$ is an alkoxy group having 1-3 carbon atoms and $Y_2$ and $Y_3$ are hydrogens or halogens. In more specific embodiments of formula 2A or 2B, one of $X_2$-$X_4$ is a halogen or a trifluoromethyl group, $Y_4$ is an alkoxy group having 1-3 carbon atoms and $Y_2$ and $Y_3$ are hydrogens. In yet more specific embodiments of formula 2A or 2B, $X_2$ is a halogen or a trifluoromethyl group, $X_3$ and $X_4$ are hydrogens, $Y_4$ is an alkoxy group having 1-3 carbon atoms and $Y_2$ and $Y_3$ are hydrogens. In particular embodiments of formula 2A or 2B, $X_2$ and $X_3$ are fluorine or chlorine. In particular embodiments of formula 2A or 2B, $X_2$ and $X_3$ are fluorine or iodine. In particular embodiments of formula 2A or 2B, $X_2$ is fluorine and $X_3$ is chlorine or iodine. In particular embodiments of formula 2A or 2B, $X_2$ is bromine. In particular embodiments of formula 2A or 2B, $X_2$ is a trifluoromethyl group. In particular embodiments of formula 2A or 2B, $X_2$ and $X_3$ together are a 5,6-methylenedioxy group. In particular embodiments of formula 2A or 2B, $X_3$ and $X_4$ together form a 1H-benzo group. In more particular embodiments of formula 2A or 2B, $Y_4$ is a methoxy group.

In a specific embodiment, the invention provides compounds of formula 2A or 2B in which two of $X_2$-$X_4$ are halogens and in particular are chlorine, bromine or iodine. In a specific embodiment, the invention provides compounds of formula 2A or 2B in which $X_2$ and $X_3$ or $X_3$ and $X_4$ are halogens and in particular are chlorine, bromine or iodine. In a specific embodiment, the invention provides compounds of formula 2A or 2B in which $X_2$ and $X_3$ or $X_3$ and $X_4$ are the same halogen or different halogens, particularly where one of $X_2$ or $X_3$ is chlorine and the other of $X_2$ or $X_3$ is flourine, bromine or iodine or particularly where one of $X_3$ or $X_4$ is chlorine and the other of $X_3$ or $X_4$ is flourine, bromine or iodine. In additional embodiments in which two of $X_2$-$X_4$ are halogens, all remaining X and Y variables are hydrogens. In additional embodiments in which two of $X_2$-$X_4$ are halogens, at least one or at least two of $Y_2$-$Y_4$ are alkoxy having 1-3 carbon atoms or halogens. In additional embodiments in which two of $X_2$-$X_4$ are halogens, one or two of $Y_2$-$Y_4$ are alkoxy having 1-3 carbon atoms or halogens and the remaining X variables and Y variables are hydrogen.

In a specific embodiment, the invention provides compounds of formula 2A or 2B in which one of $X_2$-$X_4$ are halogens and in particular are chlorine, bromine or iodine. In a specific embodiment, the invention provides compounds of formula 2A or 2B in which $X_2$ is a halogen and in particular is chlorine, bromine or iodine. In a specific embodiment, the invention provides compounds of formula 2A or 2B in which $X_3$ is a halogen and in particular is chlorine, bromine or iodine. In a specific embodiment, the invention provides compounds of formula 2A or 2B in which $X_4$ is a halogen and in particular is chlorine, bromine or iodine. In additional embodiments in which one of $X_2$-$X_4$ is a halogen, one or two of $Y_2$-$Y_4$ are alkoxy having 1-3 carbon atoms or halogens. In additional embodiments in which one of $X_2$-$X_4$ is a halogen and one or two of $Y_2$-$Y_4$ are alkoxy having 1-3 carbon atoms or halogens, all remaining X and Y variables are hydrogens. In additional embodiments in which one of $X_2$-$X_4$ is a halogen, all of $Y_1$-$Y_4$ are hydrogens. In additional embodiments in which one of $X_2$-$X_4$ is a halogen all remaining X variables and all of $Y_1$-$Y_4$ are hydrogens.

In specific embodiments, of the compounds of formula 2A or 2B, $X_2$ is Cl or I and all other X and Y variables are H. In specific embodiments, of the compounds of formula 2A or 2B, $X_2$ is Br, Cl or I, $Y_4$ is hydrogen or an alkoxy having 1-3 carbon atoms, particularly methoxy, and all other X and Y variables are H. In specific embodiments, of the compounds of formula 2A or 2B, $X_2$ is Cl and $X_3$ is F, $Y_4$ is hydrogen or an alkoxy having 1-3 carbon atoms and all other X and Y variables are H. In specific embodiments, of the compounds of formula 2A or 2B, $X_2$ is F and $X_3$ is Br or I, $Y_4$ is hydrogen or an alkoxy having 1-3 carbon atoms and all other X and Y variables are H. In specific embodiments of the compounds of formula 2A or 2B, $X_2$ is Cl and $X_3$ is Br or I, $Y_4$ is hydrogen or an alkoxy having 1-3 carbon atoms and all other X and Y variables are H. In specific embodiments of the compounds of formula 2A or 2B, $X_2$ is Br and $X_3$ is F, Cl or I, $Y_4$ is an alkoxy having 1-3 carbon atoms and all other X and Y variables are H. In specific embodiments of the compounds of formula 2A or 2B, $X_2$ is I and $X_3$ is F, Cl or Br, $Y_4$ is hydrogen or an alkoxy having 1-3 carbon atoms and all other X and Y variables are H.

In specific embodiments of the formulas 2A or 2B, two of $X_2$-$X_4$ are substituents which together form an alkylene or alkyleneoxy group which forms a carbocyclic or heterocyclic ring, particularly a 5-8 member ring carbocyclic or heterocyclic fused to the ring upon which the X groups are bonded. In specific embodiments of the formulas 2A or 2B, $X_2$ and $X_3$ are substituents which together form an alkylene or alkyleneoxy group which forms a carbocyclic or heterocyclic ring, particularly a 5-8 member ring carbocyclic or heterocyclic fused to the ring upon which the X groups are bonded. In specific embodiments of the formulas 2A or 2B, $X_3$ and $X_4$ are substituents which together form an alkylene or alkyleneoxy group which forms a carbocyclic or heterocyclic ring, particularly a 5-8 member ring carbocyclic or heterocyclic fused to the ring upon which the X groups are bonded. In additional specific embodiments, the fused ring formed is a 5- or 6-member ring. In additional specific embodiments, the fused ring contains one or two oxygen atoms. In additional embodiments in which two of $X_2$-$X_4$ are substituents which together form a carbocyclic or heterocyclic ring, at least one of $Y_2$-$Y_4$ is a halogen, an alkoxy group having 1-3 carbon atoms. In additional embodiments in which two of $X_2$-$X_4$ are substituents which together form a carbocyclic or heterocyclic ring, at least one of $Y_2$-$Y_4$ is a halogen, particularly a fluorine, a chlorine, a bromine or an iodine. In additional embodiments in which two of $X_2$-$X_4$ are substituents which together form a carbocyclic or heterocyclic ring, at least one of $Y_2$-$Y_4$ is a halogen, particularly a chlorine, a bromine or an iodine an alkoxy group having 1-3 carbon atoms. In additional embodiments in which two of $X_2$-$X_4$ are substituents which together form a carbocyclic or heterocyclic ring, $Y_2$ is a halogen, particularly a fluorine, chlorine, a bromine or an iodine. In additional embodiments in which two of $X_2$-$X_4$ are substituents which together form a carbocyclic or heterocyclic ring, $Y_2$ is a chlorine, a bromine or an iodine. In additional embodiments in which two of $X_2$-$X_4$ are substituents which together form a carbocyclic or heterocyclic ring, at least one of $Y_2$-$Y_4$ is an alkoxy group having 1-3 carbon atoms. In additional embodiments in which two of $X_2$-$X_4$ are substituents which together form a carbocyclic or heterocyclic ring, and $Y_4$ is an alkoxy group having 1-3 carbon atoms. In additional embodiments in which two of $X_2$-$X_4$ are substituents which together form a carbocyclic or heterocyclic ring, $Y_4$ is an alkoxy group having 1-3 carbon atoms and the remaining X and Y groups are hydrogens or halogens. In specific embodiments, the alkoxy group is a group other than methoxy.

In more specific embodiments of formula 2A or 2B, two of $X_1$-$X_4$ together form a 1-H benzo group fused with the indoyly ring. In more specific embodiments of formula 2A or 2B, two of $X_1$-$X_2$ together form a 1-H benzo group fused with the indoyly ring. In more specific embodiments of formula 2A or 2B, two of $X_2$-$X_3$ together form a 1-H benzo group fused with the indoyly ring. In more specific embodiments of formula 2A or 2B, two of $X_3$-$X_4$ together form a 1-H benzo group fused with the indoyly ring. In more specific embodiments of formula 2A or 2B where two of $X_1$-$X_4$ together form a 1-H benzo group fused with the indoyly ring, and one of $Y_2$-$Y_4$ is a halogen or an alkoxy group having 1-3 carbon atoms. In more specific embodiments of formula 2A or 2B, two of $X_1$-$X_4$ together form a 1-H benzo group fused with the indoyly ring, and $Y_4$ is an alkoxy group having 1-3 carbon atoms. In more specific embodiments of formula 2A or 2B, two of $X_1$-$X_4$ together form a 1-H benzo group fused with the indoyly ring, and $Y_2$ is a halogen. In more specific embodiments of formula 2A or 2B, two of $X_1$-$X_4$ together form a 1-H benzo group fused with the indoyly ring, and $Y_2$ is a chlorine, bromine or iodine. In more specific embodiments of formula 2A or 2B where two of $X_1$-$X_4$ together form a 1-H benzo group fused with the indoyly ring, one of $Y_2$-$Y_4$ is a halogen or an alkoxy group having 1-3 carbon atoms and the remaining X and Y groups are hydrogens or halogens. In more specific embodiments of formula 2A or 2B where two of $X_1$-$X_4$ together form a 1-H benzo group fused with the indoyl ring, one of $Y_2$-$Y_4$ is a halogen or an alkoxy group having 1-3 carbon atoms and the remaining X and Y groups are hydrogens. In a specific embodiment of formulas 2A and 2B, $X_4$ is an alkyl group substituted with and OH, alkoxy, carboxylate or carboxylate ester group. In a specific embodiment of formulas 2A and 2B, $X_4$ is an alkyl group substituted with an alkoxy, carboxylate or carboxylate ester group. In a specific embodiment of formulas 2A and 2B, $X_4$ is an alkyl group having 1-4 carbon atoms which is substituted with an alkoxy, carboxylate or carboxylate ester group. In a specific embodiment of formulas 2A and 2B, $X_4$ is an alkyl group having 1-4 carbon atoms which is substituted with one alkoxy, carboxylate or carboxylate ester group. In a specific embodiment of formulas 2A and 2B, $X_4$ is an alkyl group having 1-4 carbon atoms which is substituted with an alkoxy, carboxylate or carboxylate ester group, wherein the carboxylate ester group is an alkyl ester and the alkyl group of the ester has 1-6 carbon atoms. In a specific embodiment of formulas 2A and 2B where $X_4$ is an alkyl group substituted with and OH, alkoxy, carboxylate or carboxylate ester group, all Y substituents are hydrogens. In a specific embodiment of formulas 2A and 2B where $X_4$ is an alkyl group substituted with and OH, alkoxy, carboxylate or carboxylate ester group, at least one of $Y_2$-$Y_4$ is a halogen, or alkoxy group having 1-3 carbon atoms. In a specific embodiment of formulas 2A and 2B where $X_4$ is an alkyl group substituted with and OH, alkoxy, carboxylate or carboxylate ester group, at least one of $Y_2$ is a halogen, or $Y_4$ is an alkoxy group having 1-3 carbon atoms. In a specific embodiment of formulas 2A and 2B where $X_4$ is an alkyl group substituted with alkoxy, carboxylate or carboxylate ester group, at least two of $Y_2$-$Y_4$ are halogens. In specific embodiments, the alkyl group substituted with an OH, alkoxy, carboxylate or carboxylate ester group has 1 or 2 carbon atoms. In specific embodiments $X_4$ is —$(CH_2)_n$—OH, —$(CH_2)_n$—O alkyl, —$(CH_2)_n$—$CO_2H$, or —$(CH_2)_n$—$CO_2$alkyl where n is an integer ranging from 1-4. In specific embodiments $X_4$ is —$(CH_2)_n$—O alkyl or —$(CH_2)_n$—$CO_2$-alkyl where n is an integer ranging from 1-4 and the alkyl group has 1-6 or 1-3 carbon atoms.

In a specific embodiment of formulas 2A or 2B, $X_2$ is a halogen and/or $X_4$ is an alkyl group substituted with an OH, alkoxy, carboxylate or carboxylate ester group and $Y_2$-$Y_4$ are selected from hydrogens, halogens, alkoxy groups, an alkyl group substituted with an OH, an alkyl group substituted with an alkoxy, an alkyl group substituted with a carboxylate or an alkyl group substituted with an carboxylate ester group. In a specific embodiment of formulas 2A or 2B, $X_2$ is a halogen and/or $X_4$ is an alkyl group substituted with an OH, alkoxy, carboxylate or carboxylate ester group and $Y_2$ is a halogen. In a specific embodiment of formulas 2A or 2B, $X_2$ is a halogen and/or $X_4$ is an alkyl group substituted with an OH, alkoxy, carboxylate or carboxylate ester group and $Y_3$ or $Y_4$ are alkoxy groups, an alkyl group substituted with an OH, an alkyl group substituted with an alkoxy, an alkyl group substituted with a carboxylate or an alkyl group substituted with an carboxylate ester group. In a specific embodiment of formulas 2A or 2B, $X_2$ is a halogen and/or $X_4$ is an alkyl group substituted with an OH, alkoxy, carboxylate or carboxylate ester group and $Y_4$ is an alkoxy group, an alkyl group substituted with an OH, an alkyl group substituted with an alkoxy, an alkyl group substituted with a carboxylate or an alkyl group substituted with an carboxylate ester group. In a specific embodiment of formulas 2A or 2B, $X_2$ is a halogen and/or $X_4$ is an alkyl group substituted with an OH, alkoxy, carboxylate or carboxylate ester group and $Y_3$ is an alkoxy group, an alkyl group substituted with an OH, an alkyl group substituted with an alkoxy, an alkyl group substituted with a carboxylate or an alkyl group substituted with an carboxylate ester group. In specific embodiments, the alkyl group substituted with an OH, alkoxy, carboxylate or carboxylate ester group has 1-4 carbon atoms or 1-2 carbon atoms. In specific embodiments the substituted alkyl group is —$(CH_2)_n$—OH, —$(CH_2)_n$—O alkyl, —$(CH_2)_n$—$CO_2H$, or —$(CH_2)_n$—$CO_2$alkyl where n is an integer ranging from 1-4 or n is 1-2. In specific embodiments, the substituted alkyl group is —$(CH_2)_n$—O alkyl or —$(CH_2)_n$—$CO_2$-alkyl, where n is an integer ranging from 1-4 and the alkyl groups has 1-6 or 1-3 carbon atoms.

In a specific embodiment of formulas 2A or 2B, $X_2$ is a halogen and/or $X_4$ is an alkyl group substituted with an OH, alkoxy, carboxylate or carboxylate ester group, $Y_2$-$Y_4$ are selected from hydrogens, halogens, alkoxy groups, an alkyl group substituted with an OH, an alkyl group substituted with an alkoxy, an alkyl group substituted with a carboxylate or an alkyl group substituted with an carboxylate ester group and any remaining X substituents are halogens or hydrogens. In a specific embodiment of formulas 2A or 2B, $X_2$ is a halogen and/or $X_4$ is an alkyl group substituted with an OH, alkoxy, carboxylate or carboxylate ester group, $Y_2$-$Y_4$ are selected from hydrogens, halogens, alkoxy groups, an alkyl group substituted with an OH, an alkyl group substituted with an alkoxy, an alkyl group substituted with a carboxylate or an alkyl group substituted with an carboxylate ester group and any remaining X substituents are hydrogens. In a specific embodiment, the invention provides compounds 91, 92 or 93 of Table 1.

In a specific embodiment, the invention provides compounds of formula 2A or 2B with exception that the compounds are compounds other than those identified in Table 1. In a specific embodiment, compounds of formulas 1, 2A and 2B are useful for the treatment of cancer, particularly pancreatic cancer and ovarian cancer. In a specific embodiment, compounds 10, 12, 15, 40, 19, 49 and 55 of Table 1 are useful for the treatment of cancer, particularly pancreatic cancer and ovarian cancer. In a specific embodiment, compounds 10, 12, 15, 40, and 19 of Table 1 are useful for the treatment of cancer, particularly pancreatic cancer and ovarian cancer.

Compounds of formula 1 that are useful in the pharmaceutical compositions and methods of this invention include those of formula 3:

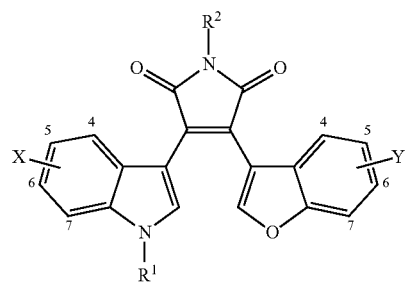

where all variables are as defined above, and where in particular $R^2$ is H, alkyl, aryl or arylalkyl. In particular, variables of formula 3 for X, Y, $R^1$ and $R^2$ may be as defined for formulas 2A and 2B above.

Compounds of formula 1 that are useful in the pharmaceutical compositions and methods of this invention include those of formula 4A:

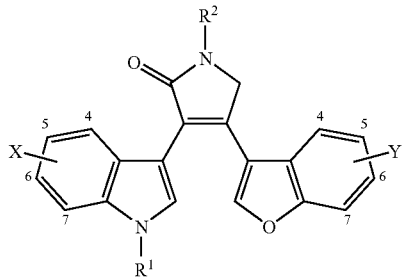

where all variables are as defined above, and where in particular $R^2$ is H, alkyl, aryl or arylalkyl. In particular, variables of formula 4A for X, Y, $R^1$ and $R^2$ may be as defined for formulas 2A and 2B above.

Compounds of formula 1 that are useful in the pharmaceutical compositions and methods of this invention include those of formula 4B:

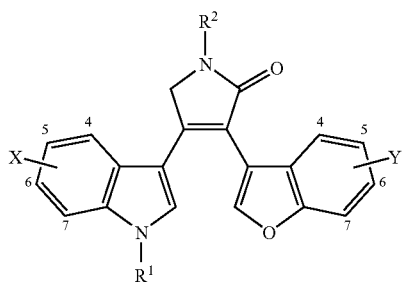

where all variables are as defined above, and where in particular $R^2$ is H, alkyl, aryl or arylalkyl. In particular, variables of formula 4B for X, Y, $R^1$ and $R^2$ may be as defined for formulas 2A and 2B above.

Compounds of formula 1 that are useful in the pharmaceutical compositions and methods of this invention include those of formula 5A:

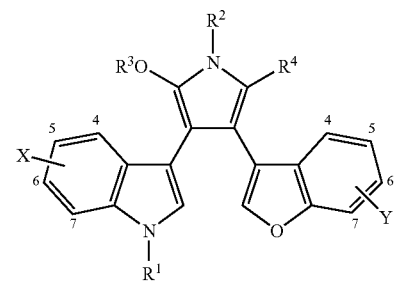

where all variables are as defined above, and where in particular $R^2$ is H, alkyl, aryl or arylalkyl, in particular $R^3$ is H, alkyl, aryl or arylalkyl and in particular $R^4$ is H, alkyl, aryl or arylalkyl. In particular, variables of formula 5A for X, Y, $R^1$ and $R^2$ may be as defined for formulas 2A and 2B above.

Compounds of formula 1 that are useful in the pharmaceutical compositions and methods of this invention include those of formula 5B:

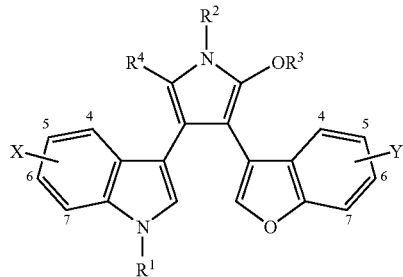

where all variables are as defined above, and where in particular $R^2$ is H, alkyl, aryl or arylalkyl, in particular $R^3$ is alkyl, aryl or arylalkyl and in particular $R^4$ is H, alkyl, aryl or arylalkyl. In particular, variables of formula 5B for X, Y, $R^1$ and $R^2$ may be as defined for formulas 2A and 2B above.

Compounds of formula 1 are useful in the pharmaceutical compositions and methods of this invention include those of formula 6A:

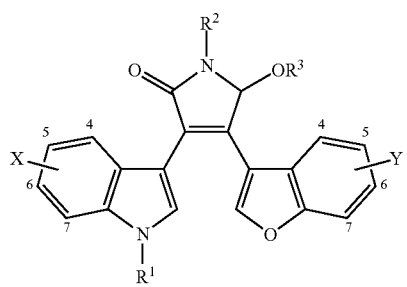

where variables are as defined above and where in particular $R^2$ is H, alkyl, aryl or arylalkyl and $R^5$ in particular is H, alkyl, aryl or arylalkyl. In particular, variables of formula 6A for X, Y, $R^1$ and $R^2$ may be as defined for formulas 2A and 2B above.

Compounds of formula 1 that are useful in the pharmaceutical compositions and methods of this invention include those of formula 6B:

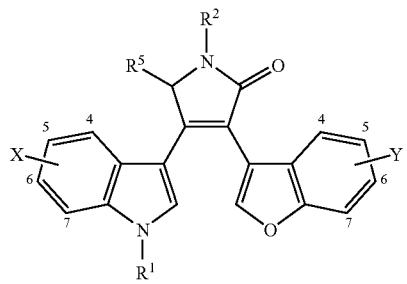

where variables are as defined above and where in particular $R^2$ is H, alkyl, aryl or arylalkyl and $R^5$ in particular is H, alkyl, aryl or arylalkyl. In particular, variables of formula 6B for X, Y, $R^1$ and $R^2$ may be as defined for formulas 2A and 2B above.

Compounds of formula 1 that are useful in the pharmaceutical compositions and methods of this invention include those of formula 7A:

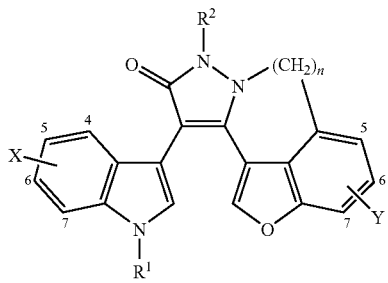

where variables are as defined above and where in particular $R^2$ is H, alkyl, aryl or arylalkyl and n is an integer ranging from 1 to 6. In specific embodiments n is 2 to 4. In particular, variables of formula 7A for X, Y, $R^1$ and $R^2$ may be as defined for formulas 2A and 2B above.

Compounds of formula 1 that are useful in the pharmaceutical compositions and methods of this invention include those of formula 7B:

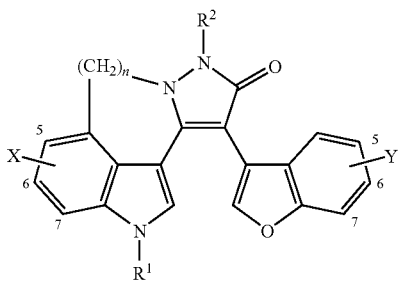

where variables are as defined above and where in particular $R^2$ is H, alkyl, aryl or arylalkyl and n is an integer ranging from 1 to 6. In specific embodiments n is 2 to 4. In particular, variables of formula 7B for X, Y, $R^1$ and $R^2$ may be as defined for formulas 2A and 2B above.

The term "alkyl" refers to a monoradical of a branched or unbranched (straight-chain or linear) saturated hydrocarbon and to cycloalkyl groups having one or more rings. Unless otherwise indicated preferred alkyl groups have 1 to 20 carbon atoms and more preferred are those that contain 1-10 carbon atoms. Short alkyl groups are those having 1 to 6 carbon atoms including methyl, ethyl, propyl, butyl, pentyl and hexyl groups, including all isomers thereof. Long alkyl groups are those having 8-20 carbon atoms and preferably those having 8-12. The term "cycloalkyl" refers specifically to alkyl groups having at least one non-aromatic ring of 3 or more carbons. The term applies to groups having a single cyclic ring or multiple rings which may be condensed or fused rings. Preferred cycloalkyl groups have at least one ring of 3-8 carbon atoms and more preferably a ring of 3-6 carbon atoms. Cycloalkyl groups include, by way of example, single ring structures such as cyclopropyl, cyclobutyl, cyclopentyl, cyclohexyl, cyclooctyl, and the like, or multiple ring structures such as adamantanyl, and the like. Unless otherwise indicated alkyl groups, including cycloalkyl, groups are optionally substituted as defined below.

The term "alkenyl" refers to a monoradical of a branched or unbranched unsaturated hydrocarbon group having one or more double bonds and to cycloalkenyl group having one or more rings wherein at least one ring contains a double bond. Unless otherwise indicated preferred alkyl groups have 1 to 20 carbon atoms and more preferred are those that contain 1-10 carbon atoms. Alkenyl groups may contain one or more double bonds (C=C) which may be conjugated or unconjugated. Preferred alkenyl groups are those having 1 or 2 double bonds and include omega-alkenyl groups. Short alkenyl groups are those having 2 to 6 carbon atoms including ethylene(vinyl), propylene, butylene, pentylene and hexylene groups including all isomers thereof. Long alkenyl groups are those having 8-20 carbon atoms and preferably those having 8-12. The term "cycloalkenyl" refers to alkenyl groups having at least one carbon ring containing and which have at least one double bond. The double bond may be in the ring. The term includes groups having rings containing 3 or more carbons. The cycloalkenyl group may contain a single cyclic ring or multiple rings which may be fused or condensed. Rings of these groups can contain 5-8 carbon atoms. Cycloalkenyl groups include, by way of example, single ring structures (monocyclic) such as cyclopropenyl, cyclobutenyl, cyclopentenyl, cyclohexenyl, cyclooctenyl, cylcooctadienyl and cyclooctatrienyl as well as multiple ring structures. Unless otherwise indicated alkenyl groups including cycloalkenyl groups are optionally substituted as defined below.

The term "alkynyl" refers to a monoradical of an unsaturated hydrocarbon having one or more triple bonds (C≡C). Unless otherwise indicated preferred alkyl groups have 1 to 20 carbon atoms and more preferred are those that contain 1-10 carbon atoms. Alkynyl groups include ethynyl, propargyl, and the like. Short alkynyl groups are those having 2 to 6 carbon atoms, including all isomers thereof. Long alkynyl groups are those having 8-20 carbon atoms and preferably those having 8-12 carbon atoms. The term "cycloalkynyl" refers to cyclic alkynyl groups of from 3 to 3-20 carbon atoms having a single cyclic ring or multiple rings which may be fused or condensed and at least one triple bond (C≡C) which may be in the ring. Rings of these groups can contain 5-8 carbon atoms. Unless otherwise indicated alkyl groups including cycloalkyl groups are optionally substituted as defined below.

The term "alicyclyl" generically refers to a monoradical that contains a carbon ring which may be a saturated ring (e.g., cyclohexyl) or unsaturated (e.g., cyclohexenyl), but is not aromatic (e.g., the term does not refer to aryl groups). Ring structures have three or more carbon atoms and typically have 3-10 carbon atoms. As indicated above for cycloalkane, cycloalkenes and cycloakynes, alicyclic radical can contain one ring or multiple rings (bicyclic, tricyclic etc.)

The term "heterocyclyl" generically refers to a monoradical that contains at least one ring of atoms, which may be a saturated, unsaturated or aromatic ring wherein one or more carbons of the ring are replaced with heteroatoms (a non-carbon atom). To satisfy valence the heteroatom may be bonded to H or a substituent groups. A ring may contain one or more different heteroatoms. Ring carbons may be replaced with —O—, —S—, —NR—, —N=, —PR—, or —POR among others, where R is an alkyl, aryl, heterocyclyl or heteroaryl group. Preferred heteroatoms are —O—, —S—, —NR— and —N=. Heterocyclyl groups include those containing 3 to 20 carbon atoms and those carrying 1-6 heteroatoms which may be the same or different.

The term "aryl" refers to a monoradical containing at least one aromatic ring. The radical is formally derived by removing a hydrogen from a ring carbon. Aryl groups contain one or more rings at least one of which is aromatic. Rings of aryl groups may be linked by a single bond or a linker group or may be fused. Exemplary aryl groups include phenyl, biphenyl and naphthyl groups. Aryl groups include those having from 6 to 20 carbon atoms and those containing 6-12 carbon atoms. Unless otherwise noted aryl groups are optionally substituted as described herein.

The term "arylalkyl" refers to a group that contains at least one alkyl group and at least one aryl group, the aryl group may be substituted on the alkyl group (e.g., benzyl (Bn, —CH$_2$—C$_6$H$_5$) or the alkyl group may be substituted on the aryl group (e.g., tolyl, —C$_6$H$_4$—CH$_3$). Unless otherwise noted either the alkyl and/or the aryl portion of the arylalkyl group can be substituted as described herein.

The term "heteroaryl" refers to a group that contains at least one aromatic ring in which one or more of the ring carbons is replaced with a heteroatom (non-carbon atom). To satisfy valence the heteroatom may be bonded to H or one or more substituent groups. Ring carbons may be replaced with —O—, —S—, —NR—, —N=, —PR—, or —POR among others, where R is an alkyl, aryl, heterocyclyl or heteroaryl group. Heteroaryl groups may also include one or more aryl groups (carbon aromatic rings). Heteroaromatic and aryl rings of the heteroaryl group may be linked by a single bond or a linker group or may be fused. Heteroaryl groups include those having aromatic rings with 5 or 6 ring atoms of which 1-3 ring atoms are heteroatoms. Preferred heteroatoms are —O—, —S—, —NR— and —N=. Heteroaryl groups include those containing 6-30 carbon atoms as well as those containing 6-12 carbon atoms. Unless otherwise noted heteroaryl groups are optionally substituted as described herein. Heteroaryl groups include among others those derived formally by removal of a H from pyrrole, furan, thiophene, imidazole, oxazole, isoxazole, thiazole, isothiazole, triazole, pyrazole, pyridine, pyrazine, pyridazine, furazan, pyrimidine, quinoline, indole, indazole, purine, isoquinoline, quinoxaline, quinazoline, cinnoline, pteridine, carbazole, phenanthridine, acridine, phenanthroline, phenazine, phthalazine, carboline, isoindole, phenarsazine, indolizine, naphthyridine, and the like. In specific embodiments, heteroaryl groups include furanyl, pyrrolyl, pyridinyl, pyrazinyl or pyrimidinyl groups.

The term "heteroarylalkyl" is analogous to the term "arylalkyl" above. It refers to a group that contains at least one alkyl group and at least one heteroaryl group, the heteroaryl group may be substituted on the alkyl group or on the heteroaryl group. A heteroaryl group may also contain one or more aryl groups (one or more carbon aromatic rings). Unless otherwise noted either the alkyl and/or the aryl portion of the arylalkyl group are optionally substituted as described herein.

In compounds herein containing two or more rings (aryl, heteroaryl, alicyclyl, or heterocyclyl), rings can be directly linked to each other through a single bond or through a bivalent radical linker which can be an "alkylene" derived from an alkyl group, or an "alkenylene" derived from an alkenyl group, which functions as a linker between two other chemical groups, e.g., between two alicyclic, heterocyclic, aryl, or heteroaryl rings. The terms alkanediyl (or alkenediyl) can also be used. Bivalent radical linker groups that may be in the compounds of this invention include heteroalkylene groups and bivalent radicals and heteroalkenylene groups and bivalent radicals in which one or more —CH$_2$— of an alkylene group or alkenylene group are replaced with an —O—, —S—, —CO, —NR—CO—, —O—CO—, or —NR—CO—NR— group where each R, independent of other R, is H, alkyl or aryl group. Carbon atoms of the alkylene and other bivalent linker groups are optionally substituted as described herein. In particular embodiments, the bivalent linker groups are substituted with one or more —OH or —NH$_2$ groups. In specific embodiments, such as those compounds of formulas 5a and 5b, two rings of a compound of the invention are linked via an alkylene chain.

The term "oxy" refers to —O— and is used in combination with descriptors for other organic radical to indicate —O-M groups where M is alkyl, alkenyl, alkynyl, aryl, aryl alkyl, heterocyclyl, heteroaryl or heteroarylalkyl, as in alkoxy, alkenoxy, alkynoxy, aryloxy, arylalkoxy, heteroaryloxy, heterocyclyloxy.

The term "alkoxy" (or alkoxide) refers to a —O-alkyl group, where alkyl groups are as defined above. The term alkenoxy (alkenoxide) refers to a —O-alkenyl group where alkenyl groups are as defined above and wherein a double bond is preferably not positioned at the carbon bonded to the oxygen. The term alkynoxy (alkynoxide) refers to a —O-alkynyl group where alkynyl groups are as defined above and wherein a triple bond is not positioned at the carbon bonded to the oxygen. Unless otherwise noted, alkyl, alkenyl and alkynyl portions of the alkoxy, alkenoxy and alkynoxy groups are optionally substituted as described herein.

The terms "hydroxyl" or "hydroxide" refer to —OH.

The terms "aryloxy," "heteroaryloxy" and "heterocyclyloxy" refer to the —O-M group where M is an aryl, heteroaryl or heterocyclyl radical, respectively.

The term "alkoxyalkyl" refers to the group —(CH$_2$)$_n$—O-alkyl (also termed an alkyl substituted with an alkoxy group) and substituted derivatives thereof where the carbons of the group are optionally substituted with one or more substituents as defined herein.

The term "thioalkoxyalkyl" refers to the group —(CH$_2$)$_n$—S-alkyl and substituted derivatives thereof where the carbons of the group are optionally substituted with one or more substituents as defined herein.

The term "acyl" refers to the radical —CO—R' where R' is an alkyl, alkenyl, alkynyl, aryl, heterocyclyl, or heteroaryl radical as described above and CO is C=O (a carbonyl group). The term "formyl" refers to the —COH group. The term "acetyl" refers to —CO—CH$_3$.

The term "acyloxy" refers to the radical —CO—O—R' where R' is an alkyl, alkenyl, alkynyl, aryl, heterocyclyl, or heteroaryl radical as described above.

The term "carboxy" or "carboxylate" refers to the group —CO—OH or its anionic form —COO— (carboxylate). The term "carboxylate ester" refers to the group —COOR' where R' is an alkyl, alkenyl, alkynyl, aryl or heteroaryl group and in particular embodiments is an alkyl ester.

The term "oxycarbonyl" refers to the radical —O—CO—R' where R' is an alkyl, alkenyl, alkynyl, aryl, heterocyclyl, or heteroaryl radical as described above.

The term "ether group" is used herein to refer to an alkyl group in which one or more —CH$_2$— groups are replaced with —O—. Unless otherwise stated, preferred ether groups have from 3 to 30 carbon atoms and more preferably have 6 to 22 carbon atoms. Ether groups include groups of the formula: —[(CH$_2$)$_n$—O—]$_m$—R where n and m are integers ranging from 1-10 and more particularly where n and m are 1-6 and those in which n is 2-4 and m is 1 or 2 and where R is H, alkyl, alkenyl, alkyl, alkenyl, alkynyl, aryl, heterocyclyl, or heteroaryl radicals as described above. Carbon atoms of ether groups are optionally substituted.

The term "thioether group" is used herein to refer to an alkyl group in which one or more —CH$_2$— groups are replaced with —S—. Unless otherwise stated preferred alkoxyalkyl groups have from 3 to 30 carbon atoms and more preferably have 6 to 22 carbon atoms. Thioether groups include groups of the formula: —[(CH$_2$)$_n$—S—]$_m$—R where n and m are integers ranging from 1-10 and more particularly where n and m are 1-6 and those in which n is 2-4 and m is 1 or 2 and where R is H, alkyl, alkenyl, alkyl, alkenyl, alkynyl, aryl, heterocyclyl, or heteroaryl radicals as described above. Carbon atoms of ether groups are optionally substituted.

Ether and thioether groups can be branched by substitution of one or more carbons of the group with alkyl groups.

The term "sulfenyl" refers to the radical —S—R' where R' is an alkyl, alkenyl, alkynyl, aryl, heterocyclyl, or heteroaryl radical as described above. The term "sulfhydryl" refers to the —SH group.

The term "sulfonyl" refers to the radical —SO$_2$—R' where R' is an alkyl, alkenyl, alkynyl, aryl, heterocyclyl, or heteroaryl radical as described above.

The term "sulfonate" refers to the radical —SO$_3$—R" where R" is hydrogen, alkyl, alkenyl, alkynyl, aryl, heterocyclyl, or heteroaryl radical as described above. An "alkyl sulfonate" group refers to a sulfonate group wherein R" is alkyl. An "aryl sulfonate" group refers to an sulfonate group wherein at least one R" is aryl. The group —SO$_3$H can be in the ionic form —SO$_3^-$.

The term "amino" refers generically to a —N(R)$_2$ group wherein each R, independently of other R groups, is hydrogen, alkyl, alkenyl, alkynyl, aryl, heterocyclyl, or heteroaryl radical as described above. Two of R may be linked to form a ring. An "alkyl amino" group refers to an amino group wherein at least one R is alkyl. An "aryl amino" group refers to an amino group wherein at least one R is aryl.

The term "amido" refers generically to an —CO—N(R)$_2$ group wherein each R, independently of other R, is hydrogen, alkyl, alkenyl, alkynyl, aryl, heterocyclyl, or heteroaryl radical as described above. Two of R may be linked to form a ring. An "alkyl amido" group refers to an amido group wherein at least one R is alkyl. An "aryl amido" group refers to an amido group wherein at least one R is aryl.

The term "aminoacyl" refers generically to an —NR—CO—R group wherein R independently of other R is hydrogen, alkyl, alkenyl, alkynyl, aryl, heterocyclyl, or heteroaryl radical as described above. Two of R may be linked to form a ring. An "alkyl aminoacyl" group refers to an aminoacyl group wherein at least one R is alkyl. An "aryl amido" group refers to an aminoacyl group wherein at least one R is aryl.

The term "carbamyl" refers to an —NR—CO—OR group wherein R independently of other R is hydrogen, alkyl, alkenyl, alkynyl, aryl, heterocyclyl, or heteroaryl radical as described above. Two of R may be linked to form a ring. The term includes the —NHCO—OH (also —NHCO—O—) group and the —NHCO—OR" group.

The term "imine" refers generically to an —N=C(R")$_2$ group or an —CR"=NR" group wherein R independently of other R is hydrogen, alkyl, alkenyl, alkynyl, aryl, heterocyclyl, or heteroaryl radical as described above. Two of R may be linked to form a ring. An "alkyl imine" group refers to an imine group wherein at least one R is alkyl. An "aryl imine" group refers to an imine group wherein at least one R is aryl.

The term "urea" or "urely" refers herein to a urea group —NR—CO—N(R)$_2$ wherein R independently of other R is hydrogen, alkyl, alkenyl, alkynyl, aryl, heterocyclyl, or heteroaryl radical as described above. In specific embodiments, all of R are H. In other embodiments, the urea has the structure —NH—CO—NH—R' wherein R' is an alkyl, alkenyl, alkynyl, aryl, heterocyclyl, or heteroaryl radical as described above.

The term "amidine" refers to a group having the structure:

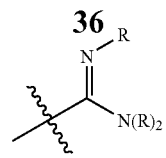

where each R, independent of other R, can be hydrogen, alkyl, heterocyclic, aryl or heteroaryl each of which can be optionally substituted. The term carboxyamidine refers to the group illustrated above in which all R are H:

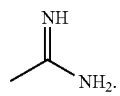

The term "phosphonate" refers to either a —PO(OR)$_2$ group or an —O—PO(OR) group where R independently of other R is hydrogen, alkyl, alkenyl, alkynyl, aryl, heterocyclyl, or heteroaryl radical as described above. Two of R may be linked to form a ring. An "alkyl phosphonate" group refers to a phosphonate group wherein at least one R is alkyl. An "aryl phosphonate" group refers to a phosphonate group wherein at least one R is aryl.

The term "phosphinate" refers to either a —PO(OR) group or a —OPOR group where R independently of other R is hydrogen, alkyl, alkenyl, alkynyl, aryl, heterocyclyl, or heteroaryl radical as described above. Two of R may be linked to form a ring. An "alkyl phosphinate" group refers to a phosphinate group wherein at least one R is alkyl. An "aryl phosphinate" group refers to a phosphinate group wherein at least one R is aryl.

The term "haloalkyl" refers to an alkyl as defined herein substituted by one or more halides (e.g., F—, Cl—, I—, Br—) as defined herein, which may be the same or different. A haloalkyl group may, for example, contain 1-10 halide substituents. Representative haloalkyl groups include, by way of example, trifluoromethyl, 3-fluorododecyl,12,12,12-trifluorododecyl, 2-bromooctyl, 3-bromo-6-chloroheptyl, and the like. Haloalkyl groups include fluoroalkyl groups. A perhaloalkyl group refers to an alkyl group in which all H have been replaced with halogen atoms. A perfluoroalkyl group is an alkyl group in which all H have been replaced with fluorine. Exemplary perhaloalkyl groups include trifluoromethyl and pentafluoroethyl groups.

The term "hydroxylalkyl" refer to an alkyl group substituted by one or more hydroxyl groups. A hydroxyalkyl group may, for example, contain 1-10 hydroxy substituents. An exemplary hydroxyalkyl group is hydroxymethyl (—CH$_2$—OH).

Alkyl, alkenyl, alkynyl, aryl, arylalkyl, heterocyclyl, heteroaryl and heteroarylalkyl groups may be substituted or unsubstituted. These groups may be optionally substituted as described herein and may contain non-hydrogen substituents dependent upon the number of carbon or other atoms in the group and the degree of unsaturation of the group. Unless otherwise indicated substituted alkyl, alkenyl alkynyl aryl, heterocyclyl and heterocyclyl groups preferably contain 1-10, and more preferably 1-6, and more preferably 1, 2 or 3 non-hydrogen substituents.

Optional substitution refers most generally to substitution of any carbon atom of any group herein including any C of a substituent group herein, with one or more of the following functional groups: cyano, isocyano, halogen (Cl, F, Br or I), hydroxyl, alkyl (including C1-C6 alkyl and C1-C3 alkyl), alkenyl, alkynyl, aryl, heteroaryl, arylalkyl, heteroarylalkyl, heterocyclyl, acyl, formyl, acetyl, haloalkyl, haloary, alkyloxy (including C1-C6 alkoxy or C1-C3 alkoxy), alkenoxy, alkynoxy, aryloxy, benzyloxy, phenyloxy(benzoyl), acyloxy, alkyl acyloxy, oxycarbonyl, alkyl oxycarbonyl —NH$_2$ (or —NH$_3^+$), amino, alkylamino, arylamino, amido, alkyl amido, arylamido, —CO—NH$_2$, imino, alkyl imino, aryl imino, ether, thioether, —SH, sulfenyl, alkyl sulfenyl (including C1-C6 alkyl sulfenyl and C1-C3 alkyl sulfenyl), hydroxyalkyl, haloalkyl, fluoroalkyl, pefluoroalkyl, trifluoromethyl, sulfonate, sulfonyl, phosponate, phosphinate or silyl, wherein alkyl, alkenyl, alkynyl, aryl, heteroaryl, arylalkyl, heteroarylalkyl, and heterocyclyl groups of the substituents are in turn optionally substituted with one or more of: cyano, isocyano, halogen, —NH$_2$ (or —NH$_3^+$), hydroxyl, —CO—NH$_2$, —COOH (or carboxylate) or —SH. Preferred substituents for compounds of formula 1 are described hereinabove.

Synthetic Methods

Bis-heteroaryl maleimides and related compounds of this invention are made by condensation of 3-indolylglyoxylic acid esters and the appropriately substituted benzofuranyl-3-acetamides (See Scheme 1, Method A). (Faul, M. M.; Winneroski, L. L.; Krumrich, C. A., *J Org. Chem.* 1998, 63, (17), 6053-6058; Faul, M. M.; Winneroski, L. L.; Krumrich, C. A., *Tetrahedron Lett.* 1999, 40, (6), 1109-1112.) The precursors are accessible from the appropriate indoles by acylation with oxalyl chloride, followed by ester formation (Faul et al. 1999), whereas the benzofurans were prepared by aminolysis of the corresponding ester. The benzofuran component can be readily prepared by Wittig reaction on the requisite benzofuranone. (Deshpande, A. R.; Paradkar, M. V., *Indian J. of Chem., Section B: Org. Chem. Including Med. Chem.* 1992, 31 B(8), 526-528.) Alternatively, a similar condensation of 3-benzofuranyl glyoxylic acid esters and the appropriately substituted indoyl-3-acetamides (Method B) can be employed. The choice between Method A and B is typically made based on ready availability of starting materials or ease of methods for making starting materials.

Exemplary synthetic schemes and details of synthetic methods are provided in the Examples. Compounds of this invention are prepared employing methods as described herein or are prepared by routine modification or adaptation of the methods herein, for example, by selection of starting materials, or variation of reagents, solvents and/or purification methods, in view of what is known in the art. Starting materials and reagents used for the preparation of the compounds of this invention or salts, esters, solvates and prodrugs thereof are available from commercial sources or can be prepared using well-known procedures. It will be appreciated by one of ordinary skill in the art that various methods for purification of starting materials, reagents, intermediates and final products of syntheses can be employed including among others filtration, distillation, crystallization, chromatography and related conventional methods. Further, starting materials, reagents, intermediates and final products of syntheses can be characterized using conventional methods, for example to obtain physical constants and spectroscopic data.

Exemplary compounds of this invention include those of Table 1 and those illustrated in Scheme 16.

Pharmaceutical Compositions and Methods of Treatment

The present invention provides methods of preventing or treating disorders, diseases conditions and symptoms in a mammal and particularly in a human, by administering to an individual in need of treatment or prophylaxis, a therapeutically effective amount of a compound of this invention to the mammal in need thereof. The result of treatment can be partially or completely alleviating, inhibiting, preventing, ameliorating and/or relieving the disorder, condition or one or more symptoms thereof. Administration includes any form of administration that is known in the art to be effective for a given type of disease or disorder, is intended to encompass administration in any appropriate dosage form and further is intended to encompass administration of a compound, pharmaceutically acceptable salt, solvate or ester thereof alone or in a pharmaceutically acceptable carrier thereof or administration of a prodrug derivative or analog of a compound of this invention which will form an equivalent amount of the active compound or substance within the body. An individual in need of treatment or prophylaxis includes those who have been diagnosed to have a given disorder or condition and to those who are suspected, for example, as a consequence of the display of certain symptoms, of having such disorders or conditions.

TABLE 1

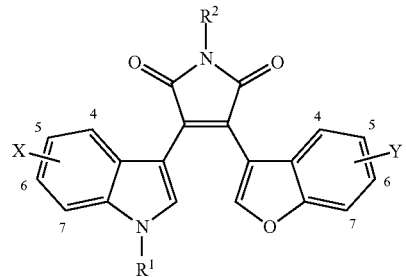

Exemplary Substituted 3-(benzofuran-3-yl)-4-(indol-3-yl)-maleimides

| # | X | Y | R$^1$ | R$^2$ |
|---|---|---|---|---|
| 1 | H | H | CH$_3$ | H |
| 2 | H | 5-F | H | H |
| 3 | H | 5-Br | CH$_3$ | H |
| 4 | H | 7-OCH$_3$ | CH$_3$ | H |
| 5 | 5-F | H | H | H |
| 6 | 5-F | H | CH$_3$ | H |
| 7 | 5-F | 6-CH$_2$OH | CH$_3$ | H |
| 8 | 5-F | 6-CH$_2$OCH$_3$ | CH$_3$ | H |
| 9 | 5-F | 6-OH | CH$_3$ | H |
| 10 | 5-F, 6-I | 7-OCH$_3$ | CH$_3$ | H |
| 11 | 5-F, 6-Br | 7-OCH$_3$ | CH$_3$ | H |
| 12 | 5-F, 6-Cl | H | CH$_3$ | H |
| 13 | 5-F, 6-Cl | 6-CH$_2$OH | CH$_3$ | H |
| 14 | 5-F, 6-Cl | 6-OCH$_3$ | CH$_3$ | H |
| 15 | 5-F, 6-Cl | 7-OCH$_3$ | CH$_3$ | H |
| 16 | 5-F, 6-Cl— | 6-O-cyclobutylmethyl | CH$_3$ | H |
| 17 | 5-F, 6-Cl— | 6-O-cyclopropylmethyl | CH$_3$ | H |
| 18 | 5-F, 6-p-Cl—Ph | 7-OCH$_3$ | CH$_3$ | H |
| 19 | 5-Br | H | CH$_3$ | H |
| 20 | 5-Br | 7-OCH$_3$ | CH$_3$ | H |
| 21 | 5-Br | H | (CH$_2$)$_3$OH | H |
| 22 | 5-Br | 6-CH$_2$OH | CH$_3$ | H |
| 23 | 5-Br | 6-O-propargyl | CH$_3$ | H |
| 24 | 5-Br | 6-O-allyl | CH$_3$ | H |
| 25 | 5-Br | 6-O-(p-CH$_3$O)-Bn | CH$_3$ | H |
| 26 | 5-,7-di-Br | 7-OCH$_3$ | CH$_3$ | H |
| 27 | 5-Cl | 5-F | CH$_3$ | H |
| 28 | 5-I | H | CH$_3$ | H |
| 29 | 5-I | 5-F | CH$_3$ | H |

TABLE 1-continued

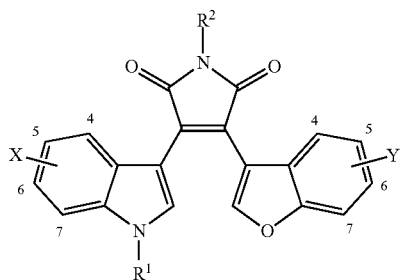

Exemplary Substituted 3-(benzofuran-3-yl)-4-(indol-3-yl)-maleimides

| # | X | Y | $R^1$ | $R^2$ |
|---|---|---|---|---|
| 30 | 5-OH | H | $CH_3$ | H |
| 31 | 5-OBn | H | $CH_3$ | H |
| 32 | 5-OBn | H | $(CH_2)_3OH$ | H |
| 33 | 5-CN | H | $CH_3$ | H |
| 34 | 5-CN | 6-$CH_2OH$ | $CH_3$ | H |
| 35 | 5-CN | 5,6-di-F | cyclopropylmethyl | H |
| 36 | 5-C≡CH | H | $CH_3$ | H |
| 37 | 5-cyclopropyl | H | $CH_3$ | H |
| 38 | 5-(ethynyl-cyclopropyl) | 5-F | $CH_3$ | H |
| 39 | 5-Morpholine | H | $CH_3$ | H |
| 40 | 5,6-Methylene dioxy | 5-F | $CH_3$ | H |
| 41 | 5-$OCH_3$ | H | $CH_3$ | H |
| 42 | 5-$OCH_3$, 6-Cl | H | $CH_3$ | H |
| 43 | 5-$OCH_3$, 6-I | H | $CH_3$ | H |
| 44 | 5-OBn | H | H | H |
| 45 | 6-OH | H | $CH_3$ | H |
| 46 | 6-OH | 5-F | $CH_3$ | H |
| 47 | 6-OBn | H | $CH_3$ | H |
| 48 | 6-OBn | 5-F | $CH_3$ | H |
| 49 | 6-$CF_3$ | 7-$OCH_3$ | $CH_3$ | H |
| 50 | 7-$CH_2OH$ | H | $CH_3$ | H |
| 51 | 7-$CH_2OH$ | 6-$CH_2OH$ | $CH_3$ | H |
| 52 | 7-$CH_2OMe$ | H | $CH_3$ | H |
| 53 | 7-OH | H | $CH_3$ | H |
| 54 | 7-OBn | H | $CH_3$ | H |
| 55 | 1H-benzo[g] | 5-, 6-di-F | $CH_3$ | H |
| 56 | 5-F | 6-$CH_2OH$ | $CH_3$ | $CH_3$ |
| 57 | 5-F, 6-CN | 5-F | $CH_3$ | H |
| 58 | 5-F, 6-$CF_3$ | 5-F | $CH_3$ | H |
| 59 | 5-F, 6-CH=$CH_2$ | 5-F | $CH_3$ | H |
| 60 | 5-F, 6-C≡CH | 5-F | $CH_3$ | H |
| 61 | 5-F, 6-OH | 5-F | $CH_3$ | H |
| 62 | 5-F, 6-SMe | 5-F | $CH_3$ | H |
| 63 | 5-F, 6-SEt | 5-F | $CH_3$ | H |
| 64 | 5,6-di-Cl | 5-F | $CH_3$ | H |
| 65 | 5-Cl, 6-OH | 5-F | $CH_3$ | H |
| 66 | 5-$CF_3$ | 5-F | $CH_3$ | H |
| 67 | 5-CN | 5-F | $CH_3$ | H |
| 68 | 5-OMe, 6-Cl | 5-F | $CH_3$ | H |
| 69 | 5-OMe, 6-Br | 5-F | $CH_3$ | H |
| 70 | 5-CN | 5-F | $CH_3$ | H |
| 71 | 5-$CF_3$ | 6-OMe | $CH_3$ | H |
| 72 | 5-CN | 6-OMe | $CH_3$ | H |
| 73 | 6-$CHF_2$ | 7-OMe | $CH_3$ | H |
| 74 | 5-$CF_3$ | 7-OMe | $CH_3$ | H |
| 75 | 5-Cl, 6-OH | 6-$CH_2OH$ | $CH_3$ | H |
| 76 | 5-F, 6-Me | 6-$CH_2OH$ | $CH_3$ | H |
| 77 | 5-F, 6-Cl | 6-$CH_2OMe$ | $CH_3$ | H |
| 78 | 5-CN | 6-$CH_2CH_2OH$ | $CH_3$ | H |
| 79 | 5-Br | 6-$CH_2CH_2CO_2H$ | $CH_3$ | H |
| 80 | 6-$CH_2OH$ | H | $CH_3$ | H |
| 81 | 6-$CH_2OMe$ | H | $CH_3$ | H |

TABLE 1-continued

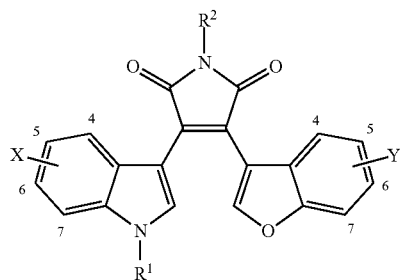

Exemplary Substituted 3-(benzofuran-3-yl)-4-(indol-3-yl)-maleimides

| # | X | Y | $R^1$ | $R^2$ |
|---|---|---|---|---|
| 82 | 7-$CH_2OH$ | H | $CH_3$ | H |
| 83 | 7-$CH_2OH$ | 6-$CH_2OH$ | $CH_3$ | H |
| 85 | 7-$CH_2CH_2OH$ | H | $CH_3$ | H |
| 86 | 7-$CH_2CH_2CO_2H$ | H | $CH_3$ | H |
| 87 | 7-$CH(CH_3)$=$CH_2$ | H | $CH_3$ | H |
| 88 | 7-$C(CH_3)_2OCH_3$ | H | $CH_3$ | H |
| 89 | 5-$CF_3$ | 5-F | $CH_2CF_3$ | H |
| 90 | H | 5-F | $CH_2CF_3$ | H |
| 91 | 5-F | 6-$CH_2OCH_3$ | $CH_3$ | H |
| 92 | 7-$CH_2OMe$ | 6-$CH_2OH$ | $CH_3$ | H |
| 93 | 7-$CH_2CH_2COOEt$ | H | $CH_3$ | H |

The term "therapeutically effective amount," as used herein, refers to the amount of a compound of Formula 1 (or a salt, ester or solvate thereof) that, when administered to an individual is effective to at least partially treat a disorder, disease or condition from which the individual is suffering, to at least partially ameliorate a symptom of such disorder, disease or condition, to prevent or ameliorate a disorder or condition which may affect an individual or to prevent further deterioration or decrease the severity of a disorder or conditions which may affect an individual. As is understood in the art, the therapeutically effective amount of a given compound will depend at least in part upon, the mode of administration, any carrier or vehicle (e.g., solution, emulsion, etc.) employed, the specific disorder or condition, and the specific individual to whom the compound is to be administered (age, weight, condition, sex, etc.).

The dosage requirements need to achieve the "therapeutically effective amount" vary with the particular compositions employed, the route of administration, the severity of the symptoms presented and the particular subject being treated. Based on the results obtained in standard pharmacological test procedures, projected daily dosages of active compound can be determined as is understood in the art.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like.

In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. Compounds of formula 1 can also be in the form of zwitterions.

Scheme 16: Additional Exemplary Compounds of Formula 1 where $R^1$ is methyl and $R^2$ is H.

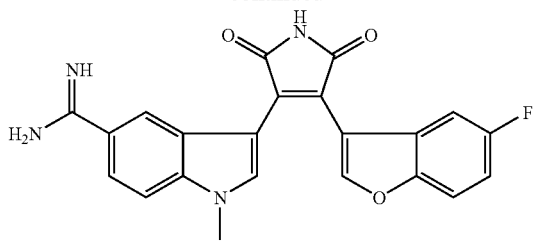
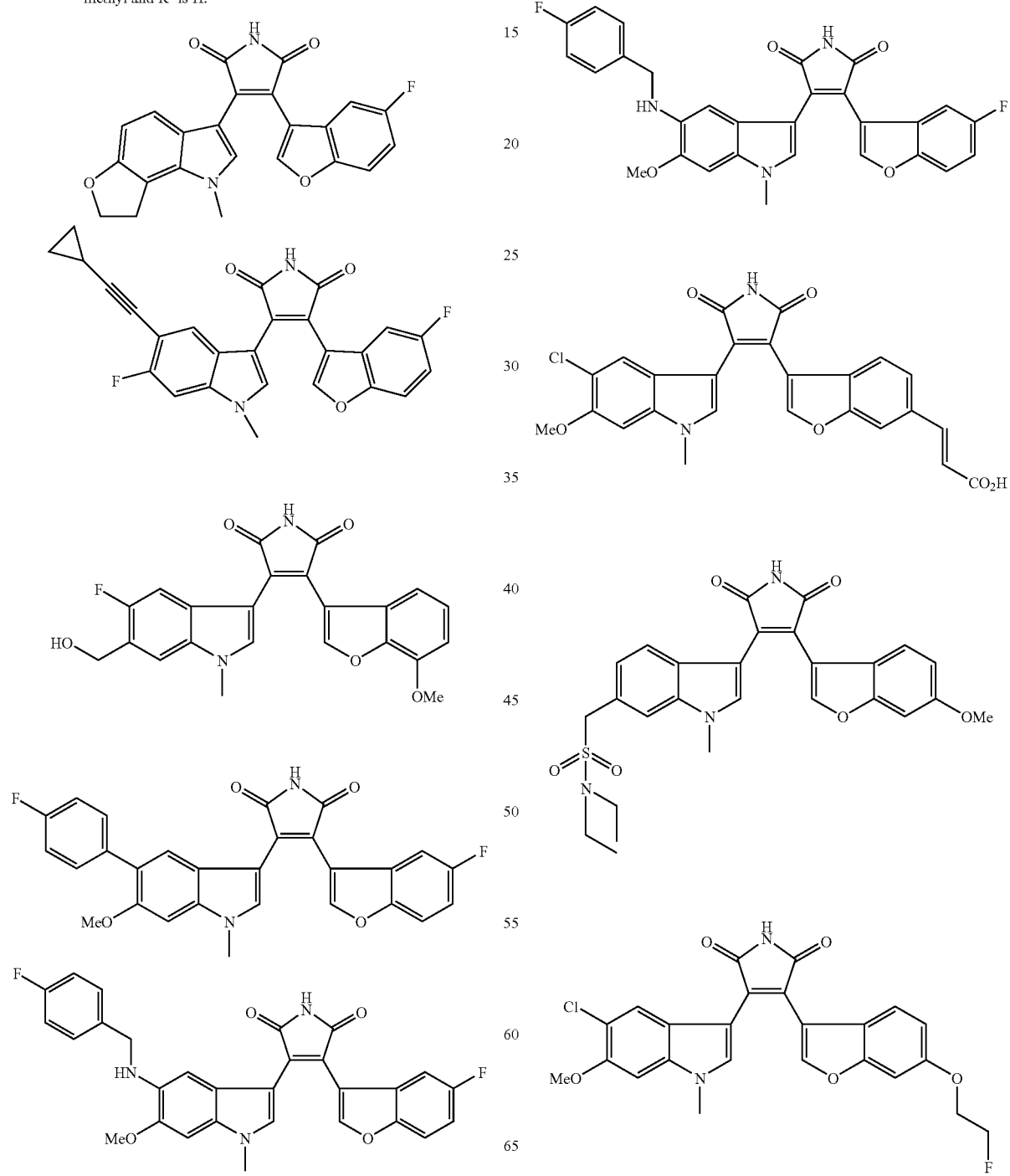

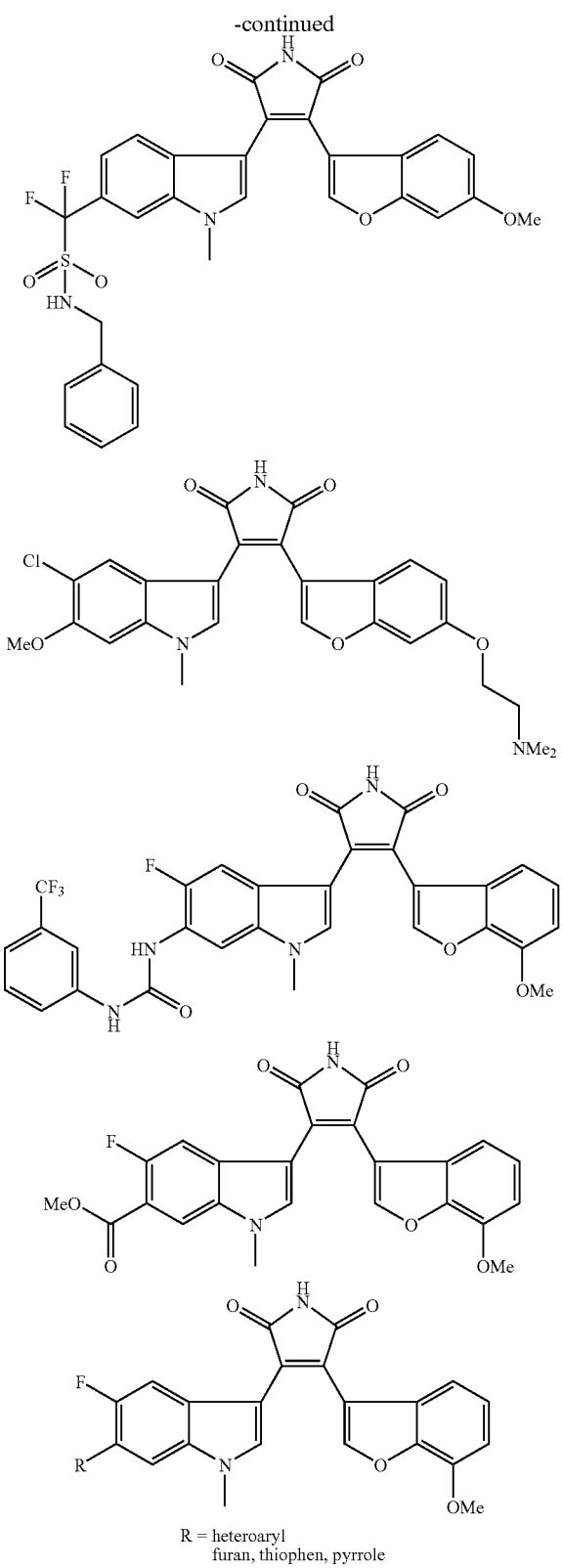

R = heteroaryl
furan, thiophen, pyrrole

The invention expressly includes pharmaceutically usable solvates of compounds according to formula I. The compounds of formula I can be solvated, e.g. hydrated. The solvation can occur in the course of the manufacturing process or can take place, e.g. as a consequence of hygroscopic properties of an initially anhydrous compound of formula I (hydration). A particular solvate form of a compound of this invention is a hydrate.

"Pharmaceutically acceptable esters" refers ester derivatives of compounds of Formula 1 or other formulas herein formed at certain functional groups which are capable of conversion back to the parent compounds in vivo. For example, the COOH groups of compounds can be esterified. Examples of such esters include physiologically acceptable and metabolically labile ester derivatives, such as methoxymethyl esters, methylthiomethyl esters and pivaloyloxymethyl esters. Additionally, any physiologically acceptable equivalents of the compounds of general formula 1, similar to the metabolically labile esters, which are capable of producing the compounds of general formula 1 in vivo are encompassed within this invention. Esters more specifically include methyl, ethyl, propyl, butyl and benzyl esters. Further examples of pharmaceutically useful esters are compounds of Formula 1, wherein hydroxy groups can be esterified, for example by formation of formate, acetate, propionate, butyrate, isobutyrate, valerate, 2-methylbutyrate, isovalerate and N, N-dimethylaminoacetate esters.

In certain embodiments, the present invention is directed to prodrugs of compounds of Formula 1 and other formulas herein. The term "prodrug," as used herein, means a compound that is convertible in vivo by metabolic means (e.g. by hydrolysis) to a compound of Formula 1. Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al. (ed.), "Design and Application of Prodrugs, Textbook of Drug Design and Development, Chapter 5, 113-191 (1991), Bundgaard, et al., Journal of Drug Delivery Reviews, 8:1-38 (1992), Bundgaard, J. of Pharmaceutical Sciences, 77:285 et seq. (19SS); and Higuchi and Stella (eds.) Prodrugs as Novel Drug Delivery Systems, American Chemical Society (1975), each of which is hereby incorporated by reference in its entirety.

The compounds of this invention can be administered in general in any appropriate dosage form, including, among others, forms suitable for administration orally, intravenously, sublingually, ocularly, transdermally, rectally, vaginally, topically, intramuscularly, subcutaneously, bucally, or nasally.

The compounds of this invention can be administered in oral dosage forms including tablets, capsules, pills, powders, granules, elixirs, tinctures, suspensions, syrups and emulsions. Oral dosage forms may include sustained release or timed release formulations. The compounds of this invention may also be administered intravenously, intraperitoneally, subcutaneously, or intramuscularly, all using dosage forms well known to those of ordinary skill in the pharmaceutical arts. Compounds of the invention can further be administered topically employing appropriate carriers.

Compounds of this invention can also be administered in intranasal form by topical use of suitable intranasal vehicles. For intranasal or intrabronchial inhalation or insulation, the compounds of this invention may be formulated into an aqueous or partially aqueous solution, which can then be utilized in the form of an aerosol.

The compounds of this invention can also be administered to the eye (ocularly), preferably as a topical opthalmic formulation. The compounds of this invention can also be combined with a preservative and an appropriate vehicle such as mineral oil or liquid lanolin to provide an opthalmic ointment.

The compounds of this invention may be administered rectally or vaginally in the form of a conventional suppository.

The compounds of this invention may also be administered transdermally through the use of a transdermal patch containing the active compound and a carrier that is inert to the active compound, is non toxic to the skin, and allows delivery of the agent for systemic absorption into the blood stream via the skin.

The compounds of the invention may be administered employing an occlusive device. A variety of occlusive devices can be used to release an ingredient into the blood stream such as a semipermeable membrane covering a reservoir containing the active ingredient with or without a carrier, or a matrix containing the active ingredient. Other occlusive devices are known in the literature.

The therapeutically active compounds of the invention can be administered alone, but generally will be administered with a pharmaceutical carrier selected upon the basis of the chosen route of administration and standard pharmaceutical practice.

Pharmaceutical compositions of this invention comprise one or more compounds, pharmaceutically acceptable salts, esters or solvates thereof or a prodrug thereof in combination with a pharmaceutically acceptable carrier, excipient, or diluent. Such compositions are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety.

Pharmaceutically acceptable carriers are those carriers that are compatible with the other ingredients in the formulation and are biologically acceptable. Carriers can be solid or liquid.

Solid carriers can include one or more substances that can also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers can be used in preparing solutions, suspensions, emulsions, syrups and elixirs. The active ingredient can be dissolved or suspended in a pharmaceutically acceptable liquid carrier such as water (of appropriate purity, e.g., pyrogen-free, sterile, etc.), an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water of appropriate purity, aqueous solutions (particularly containing additives as above, e.g. cellulose derivatives, sodium carboxymethyl cellulose solution), alcohols (including monohydric alcohols and polyhydric alcohols e.g. glycols) and their derivatives, and oils. For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant. Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form.

The carrier can also be in the form of creams and ointments, pastes, and gels. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packaged powders, vials, ampules, pre-filled syringes or sachets containing liquids. The unit dosage form can be, for example, a capsule or tablet itself, or it can be the appropriate number of any such compositions in package form.

The dosage can vary within wide limits and as is understood in the art will have to be adjusted to the individual requirements in each particular case as discussed above. By way of general guidance, the daily oral dosage can vary from about 0.01 mg to 1000 mg, 0.1 mg to 100 mg, or 10 mg to 500 mg per day of a compound of Formula 1 or of the corresponding amount of a pharmaceutically acceptable salt thereof. The daily dose may be administered as single dose or in divided doses and, in addition, the upper limit can also be exceeded when this is found to be indicated.

Dependent upon the particular protein kinase-related disease, disorder or condition to be treated employing the compounds of this invention, additional therapeutic agents, which are normally administered to treat or prevent that disease, disorder or condition, may be administered together with an inhibitor of this invention. For example, in the treatment of diabetes other anti-diabetic agents may be combined with a GSK-3 inhibitor of this invention to treat diabetes. For example, such anti-diabetic agents include, without limitation, insulin or insulin analogues, glitazones, alpha glucosidase inhibitors, biguanides, insulin sensitizers and sulfonyl ureas.

Other examples of agents that can be combined with the inhibitors of this invention in methods of treatment include, without limitation, chemotherapeutic agents, anti-proliferative agents, anti-inflammatory agents, This invention also provides kits for conveniently and effectively implementing the therapeutic and treatment methods of this invention. Kits of this invention comprise one or more compounds of this invention (compounds of Formula 1 and pharmaceutically acceptable salts, esters and solvates thereof) and a means for facilitating compliance with methods of this invention. Kits typically comprise container means or packaging for holding a selected amount of the active compound of this invention or a pharmaceutical composition comprising the active compound of this invention. The kit provides convenient and effective means for assuring that an individual to be treated takes the appropriate active ingredient in the correct dosage in the correct manner to achieve the desired therapeutic benefit. The compliance means of such kits comprises any means which facilitates administration of the active compounds according to the method of this invention. Kits can be provided which are suitable for facilitating administration to the individual to be treated by a health care professional to, for example, assist in providing the proper dosage at proper intervals to a given patient. Alternatively kits can be provided which are suitable for facilitating self-administration by the individual being treated or by a non-health care profession who may be assisting the individual. Compliance means include, for example, instructions, packaging and dispensing means or combinations thereof suitable for the particular application of the kit. Kit components may be packaged for manual, automated or partially automated practice of the methods herein.

The invention provides medicaments for therapeutic application, in particular for the treatment of protein kinase-related diseases, disorders or conditions. In specific embodiments, the invention provides medicaments for treatment of GSK-3-related diseases, disorders or conditions. Medicaments herein contain one or more than one of the compounds of formula 1 or salts, esters, solvates or prodrugs thereof, optionally in combination with a pharmaceutically acceptable carrier and in a dosage form appropriate for the intended administration of the medicament. The invention provides methods of making a medicament employing one or more compounds of formula 1 or salts, esters, solvates or prodrugs thereof. Medicaments are made using methods that are well known in the art. In a specific embodiment, medicaments of this invention are made by combining one or more compounds, salts, esters or solvates of formula 1, or prodrugs thereof with a pharmaceutically acceptable carrier suitable for administration by an appropriate means for administration to an individual in need of treatment.

The invention further extends to the use of one or more compounds of formula 1, salts, esters, solvates or prodrugs thereof for the treatment of one or more protein kinase-related diseases, disorders or conditions as defined above. The invention additionally extends to the use of one or more compounds of formula 1, salts, esters, solvates or prodrugs thereof for the treatment of one or more GSK-3-related diseases, disorders or conditions as defined above. The invention additionally extends to the use of one or more compounds of formula 2, salts, esters, solvates or prodrugs thereof for the treatment cancer, particularly pancreatic cancer.

Certain compounds of this invention also have utility as starting materials for the preparation of compounds that are in turn useful in various therapeutic applications, for example, for the preparation of additional inhibitors of protein kinases and particularly for preparation of inhibitors of GSK-3.

In cases in which the compounds of this invention have carbon-carbon double bonds, unless otherwise specified, both the cis (Z) and trans (E) isomers are encompassed in this invention. More generally, unless otherwise specified, all structural isomers of the compounds of this invention are encompassed in the invention.

Compounds of the invention can include those which may exist in tautomeric forms, such as keto-enol tautomers. Each tautomeric form is encompassed in the invention, whether the forms exist in equilibrium with each other or if the tautomer is locked in one form by appropriate substitution, as is understood in the art.

The scope of the invention as described and claimed encompasses the racemic forms of the compounds as well as the individual enantiomers and non-racemic mixtures thereof. The compounds of the invention may contain one or more asymmetric carbon atoms, so that the compounds can exist in different stereoisomeric forms. The compounds can be, for example, racemates or optically active forms. The optically active forms can be obtained by resolution of the racemates or by asymmetric synthesis. In a preferred embodiment of the invention, enantiomers of the invention exhibit specific rotation $[\alpha]$ that is + (positive). Preferably, the (+) enantiomers are substantially free of the corresponding (−) enantiomer. Thus, an enantiomer substantially free of the corresponding enantiomer refers to a compound which is isolated or separated via separation techniques or prepared free of the corresponding enantiomer. "Substantially free," means that the compound is made up of a significantly greater proportion of one enantiomer. In preferred embodiments the compound is made up of at least about 90% by weight of a preferred enantiomer. In other embodiments of the invention, the compound is made up of at least about 99% by weight of a preferred enantiomer. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, N.Y., 1962); Wilen, S. H. Tables of Resolving Agents and Optical Resolutions p. 268 (E. L. Eliel, Ed., Univ. of Notre Dame Press, Notre Dame, Ind. 1972).

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. A number of specific groups of variable definitions have been described herein. It is intended that all combinations and subcombinations of the specific groups of variable definitions are individually included in this disclosure. When a compound is described herein such that a particular isomer, enantiomer or diastereomer of the compound is not specified, for example, in a formula or in a chemical name, that description is intended to include each isomers and enantiomer of the compound described individual or in any combination.

Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of compounds herein which are enriched in one or more isotopes such that an isotope distribution in the compound is different from the naturally-occurring isotope distribution are encompassed within this invention. More specifically, isotopic variants include those which contain isotopic variants of hydrogen, carbon, nitrogen and halogens. Isotopic variants of a molecule are generally useful as standards in assays for the molecule and in chemical and biological research related to the molecule or its use. Isotopic variants may also be useful in diagnostic assays and in therapeutics. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

Any one or more of the compounds specifically disclosed in this specification can be excluded from any of the embodiments of the invention. Any one or more disorder, conditions or disease, specifically disclosed in this specification can be excluded from any of the embodiments of the invention.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, can be excluded from the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. The term "comprising" is intended to be broader than the terms "consisting essentially of" and "consisting of", however, the term "comprising" as used herein in its broadest sense is intended to encompass the narrower terms "consisting essentially of" and "consisting of", thus the term "comprising" can be replaced with "consisting essentially of" to exclude steps that do not materially affect the basic and novel characteristics of the claims and "comprising" can be replaced with "consisting of" to exclude not recited claim elements.

The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All references cited herein are hereby incorporated by reference to the extent that there is no inconsistency with the disclosure of this specification. Some references provided herein are incorporated by reference to provide details concerning sources of starting materials, additional starting materials, additional reagents, additional methods of synthesis of the compounds herein, additional methods of analysis and assessment of the biological functions of the compounds herein, additional biological materials, methods for assessing biological function of the compounds herein and additional therapeutic and prophylactic uses of the protein kinase inhibitors, particularly the GSK-3 inhibitors of this invention.

THE EXAMPLES

Example 1

Synthesis of 3-(benzofuran-3-yl)-4-(indol-3-yl)-maleimides

Schemes 1-13 illustrate synthetic methods employed to prepare compounds of this invention. Additional details of synthetic methods are provided below.
General Procedures for the Preparation of Maleimides:
The following methods represent the typical procedures for the synthesis of the 3-benzofuranyl-4-indolylmalemide-based ligands.

Method A: 3-Benzofuran-3-yl-4-(5-bromo-1-methyl-1H-indol-3-yl)-pyrrole-2,5-dione (19). (See Scheme 1 and Scheme 3)

To a solution of 5-bromo-indole (3.30 g, 11.73 mmol) in dry DMF (15 mL) cooled with an ice bath was added NaH (55% suspension in mineral oil, 1.02 g, 23.46 mmol), followed by methyl iodide (2.50 g, 17.60 mmol) after which the reaction mixture was allowed to warm to room temperature. After 6 h the reaction mixture was poured into ice-water; 1N HCl was added to adjust the pH to about 4, and the solution was extracted with ethyl acetate. The ethyl acetate extract was washed with water and brine, then dried over anhydrous $Na_2SO_4$, and concentrated in vacuo. The residue was filtered through silica gel (ethyl acetate:hexane; 1:4). The product, 5-bromo-1-methyl-1H-indole, was subjected to further reaction without additional purification. To a solution of 5-bromo-1-methyl-1H-indole in $Et_2O$ (20 mL) cooled to 0° C. a 2.0 M solution of oxalyl chloride in THF (17.0 mL, 34.0 mmol) was added dropwise. The reaction was then stirred for 0.5 h at 0° C. and allowed to warm to room temperature and stirred overnight. It was then cooled to −60° C. and a 21% solution of NaOEt in EtOH (13.50 mL, 45.70 mmol) was added, after which the reaction mixture was allowed to warm to room temperature. The reaction was quenched by the addition of water and diluted with ethyl acetate. The organic layer was separated, dried over anhydrous $Na_2SO_4$ and concentrated. The residue was purified by column chromatography (ethyl acetate:hexane; 1:3) to give a product (2.92 g, 86%).

(5-Bromo-1-methyl-1H-indol-3-yl)-oxo-acetic acid ethyl ester. $^1$H NMR ($CDCl_3$, 400 MHz) 1.43 (t, J=7.1 Hz, 3H), 3.83 (s, 3H), 4.41 (q, J=7.1 Hz, 2H), 7.19 (d, J=8.6 Hz, 1H), 7.40 (dd, J=1.8, 8.6 Hz, 1H), 8.26 (s, 1H), 8.52 (d, J=1.8 Hz, 1H); $^{13}$C NMR (CDCl$_3$, 75 MHz) 14.0, 33.9, 62.1, 111.3, 112.2, 117.2, 125.1, 126.1, 127.0, 128.4, 135.9, 140.7, 162.6, 177.1.

Benzofuran-3-yl-acetic acid ethyl ester. To a solution of benzofuran-3-one (1.00 g, 7.45 mmol) in toluene (25 mL) was added (carboxymethylene)triphenyl phosphorane (3.92 g, 11.2 mmol), and the mixture was refluxed for 24 h. The reaction mixture was cooled to room temperature and concentrated. The residue was purified by column chromatography (hexane, then ethyl acetate:hexane; 1:3) to give a product (0.89 g, 58%). The spectral data for this compound are identical to that reported in the literature. (Deshpande, A. R.; Paradkar, M. V. Syn.Commun., 1990, 20, 809).

2-Benzofuran-3-yl-acetamide. Product obtained from the previous step was added to liquid ammonia at −78° C., the reaction flask was sealed and heated for 48 h at 50° C. The reaction mixture was cooled, the excess of ammonia was allowed to evaporate and residue was purified by column chromatography (ethyl acetate:hexane; 2:3) to give a product (0.69 g, 90%). $^1$H NMR (DMSO-d6, 400 MHz) 3.49 (s, 2H), 7.00 (bs, 1H), 7.23-7.31 (m, 2H), 7.55 (d, J=8.0 Hz, 1H), 7.60 (bs, 1H), 7.63 (d, J=7.5 Hz, 1H), 7.82 (s, 1H), $^{13}$C NMR (DMSO-d6, 75 MHz) 30.7, 111.6, 115.4, 120.5, 122.8, 124.6, 128.3, 143.5, 154.9, 171.7.

Scheme 2

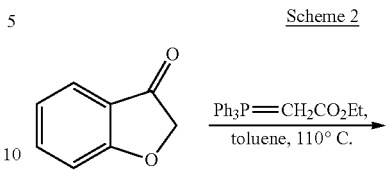

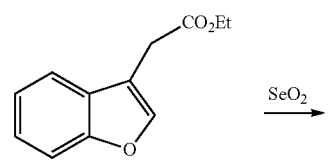

Scheme 1

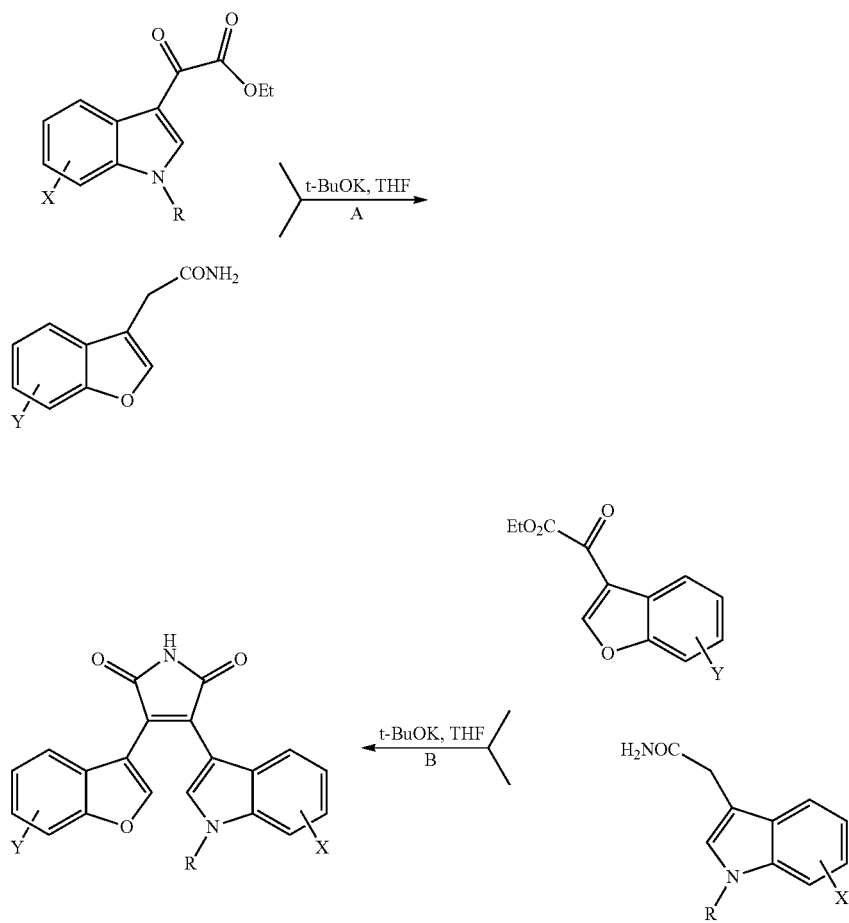

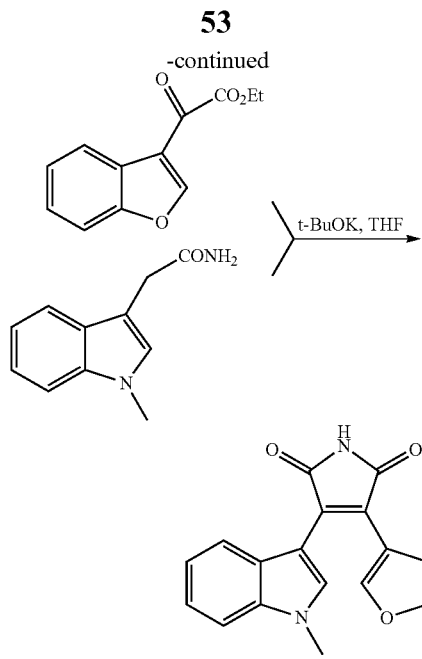
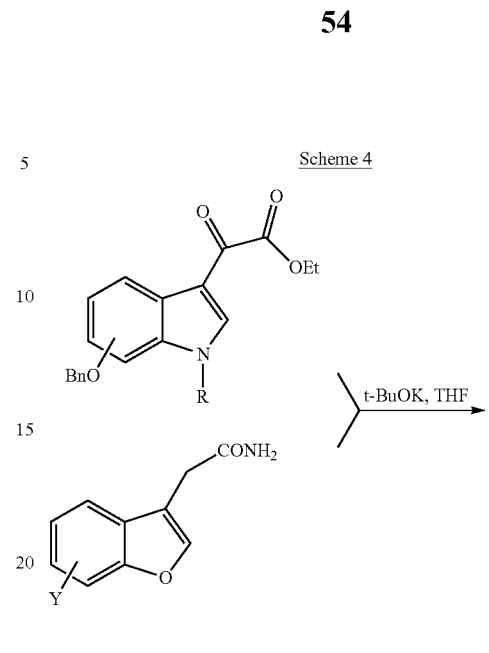
Scheme 4
Scheme 3
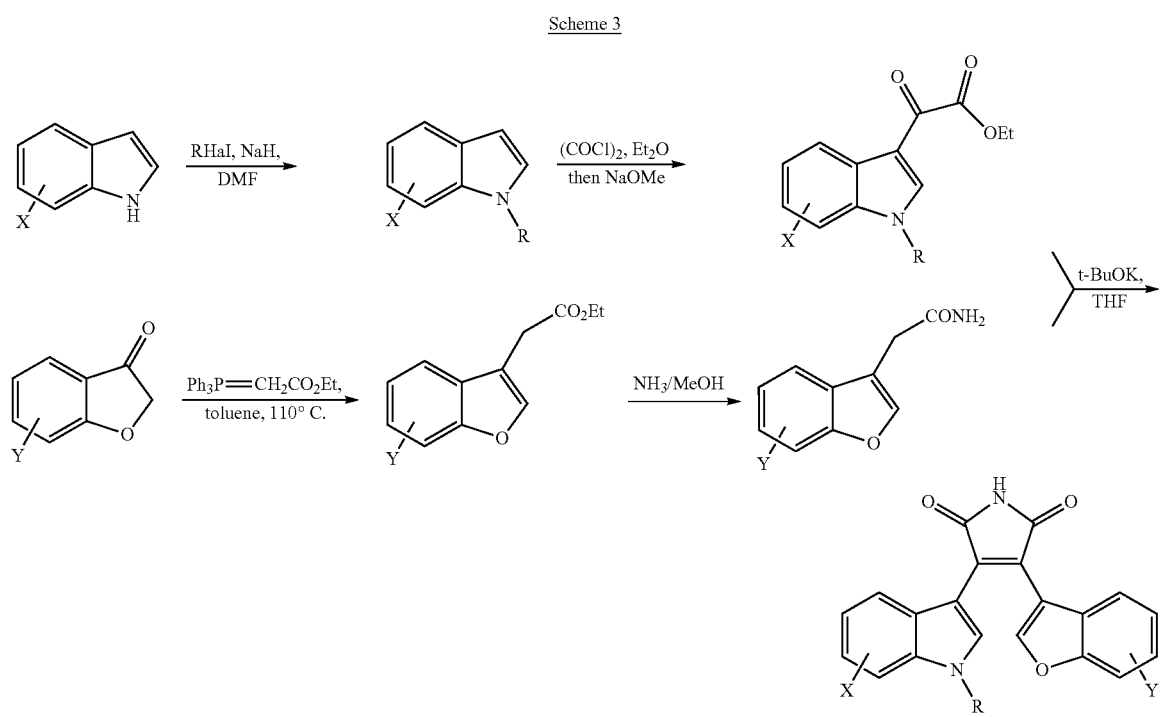
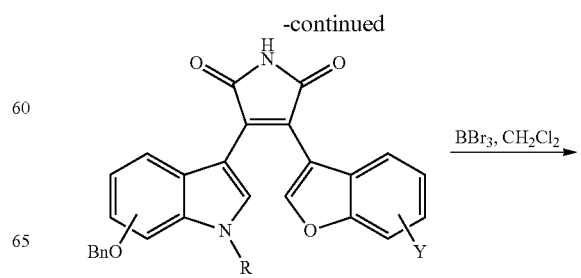

55
-continued
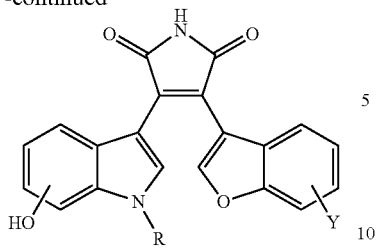
56
-continued
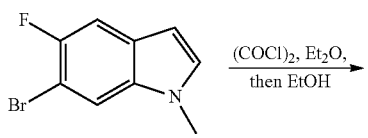
Scheme 5
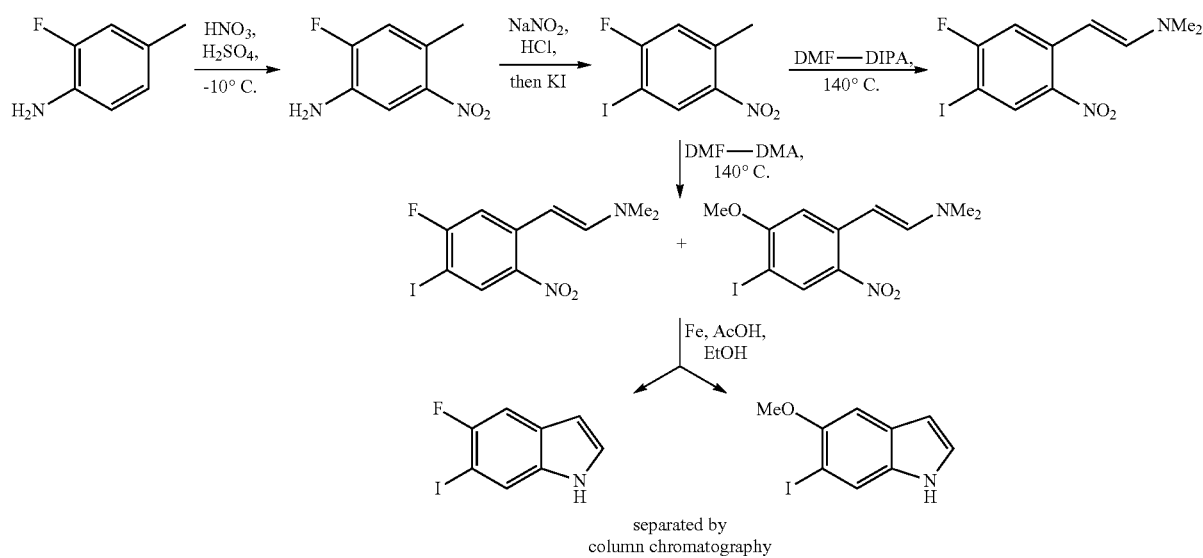
separated by column chromatography
Scheme 6
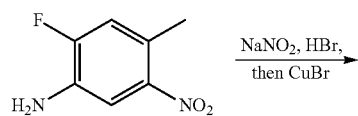
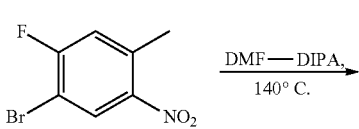
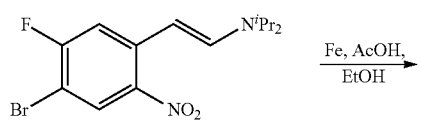
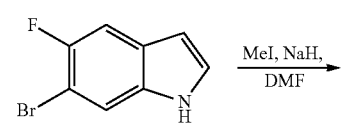
-continued
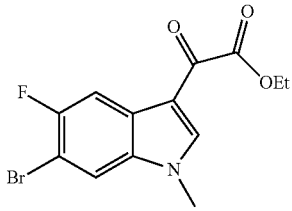
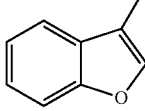
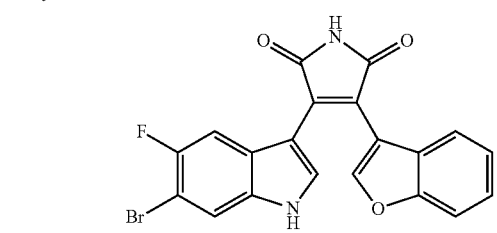

Scheme 7
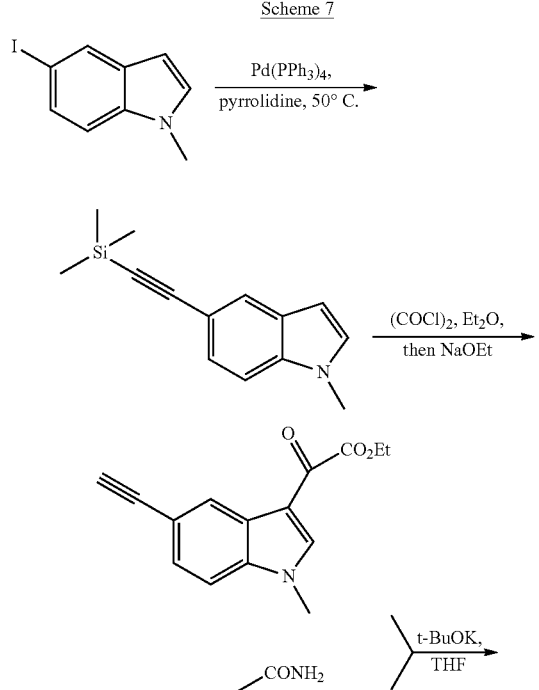
Scheme 8
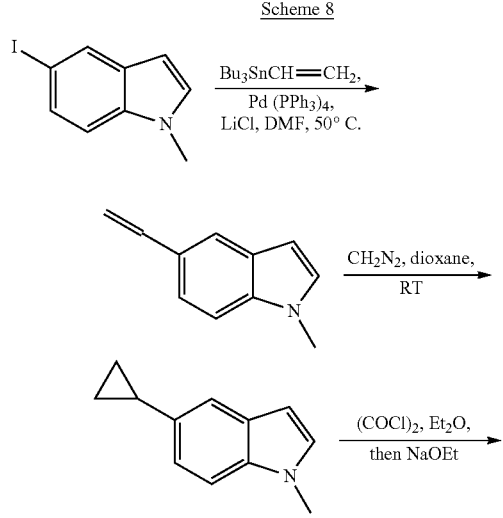
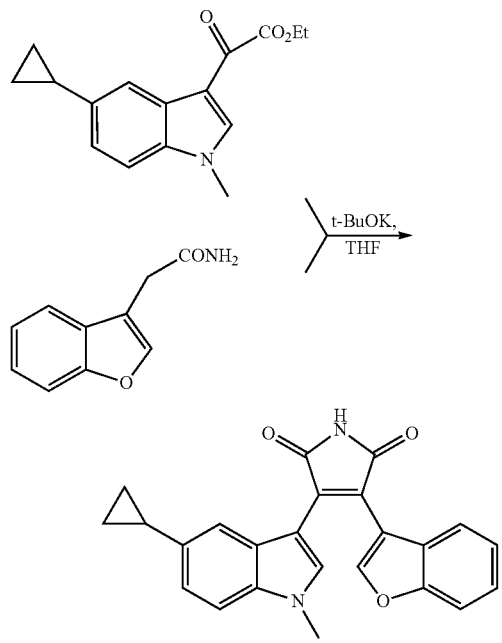
Scheme 9
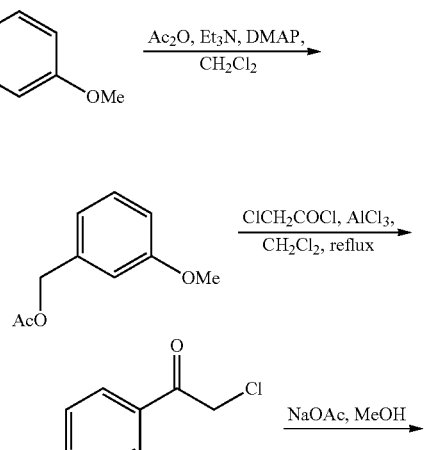
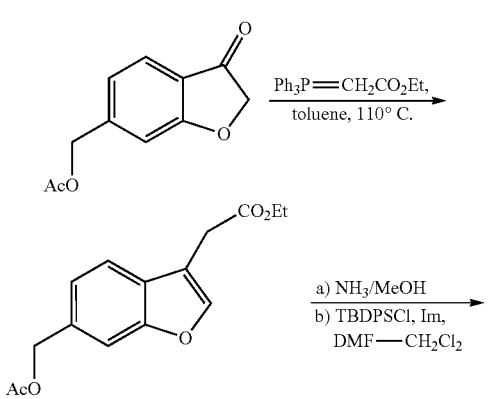

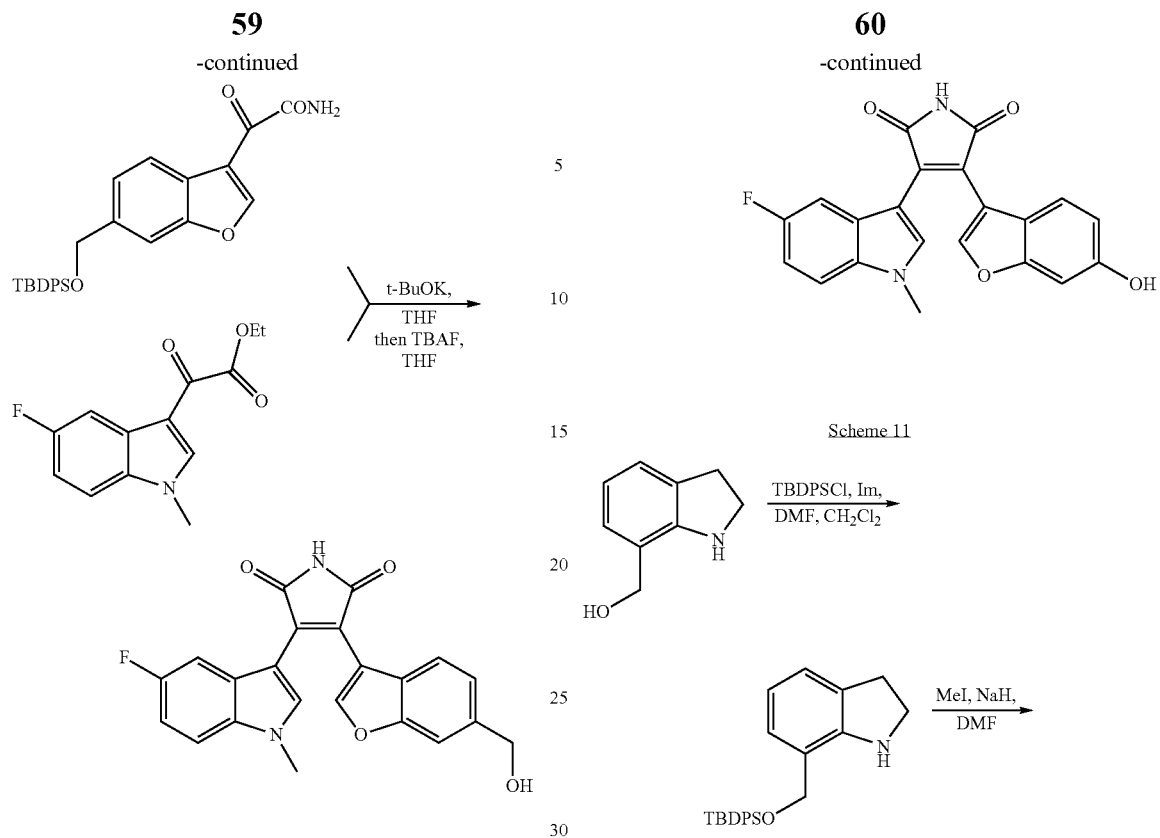
Scheme 10
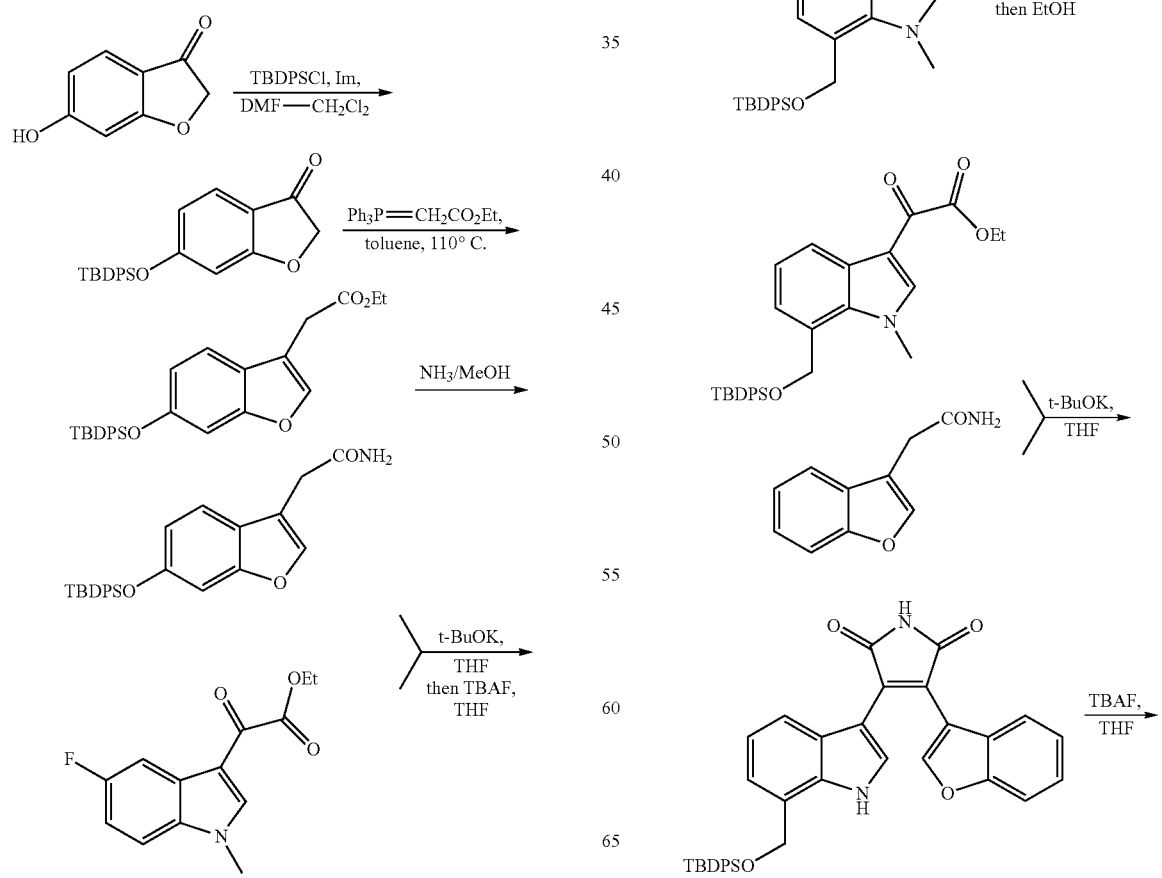
Scheme 11

-continued

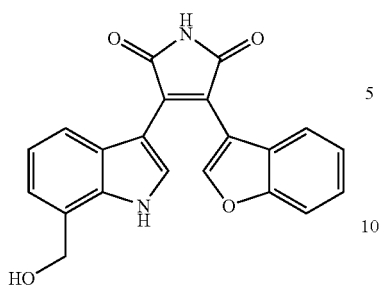

Scheme 12

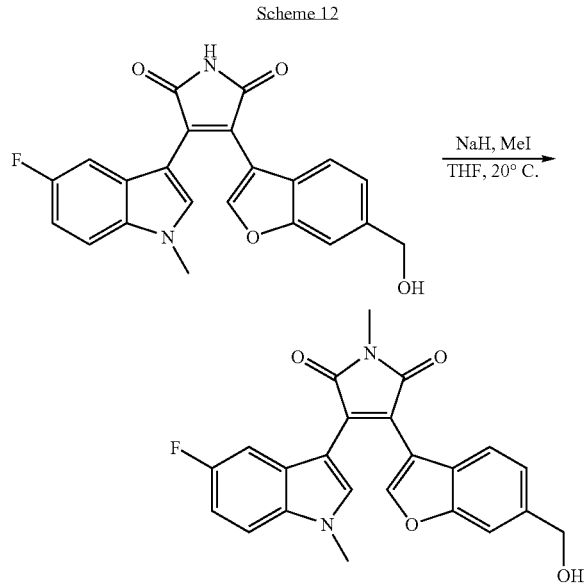

Scheme 13

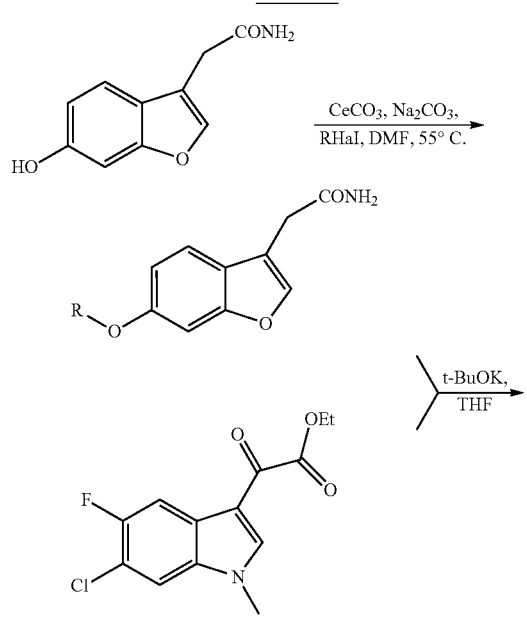

-continued

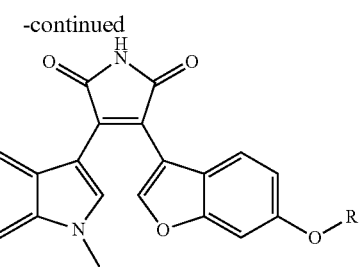

3To a suspension of 2-benzofuran-3-yl-acetamide (Y=H, 50 mg, 0.28 mmol) and indolyl-3-glyoxylate (X=5-Br, R=Me; 88 mg, 0.28 mmol) in dry THF (2.5 mL) at 0° C. was added dropwise a 1.0 M solution of tert-BuOK in THF (1.1 mL), and the reaction mixture was allowed to stir at room temperature overnight. The reaction mixture was quenched with 12 N HCl and diluted with EtOAc. The organic solution was washed with saturated NaHCO$_3$, brine, then dried over Na$_2$SO$_4$, evaporated in vacuo and purified by preparative TLC (ethyl acetate:hexane; 2:3) to afford product 3-Benzofuran-3-yl-4-(5-bromo-1-methyl-1H-indol-3-yl)-pyrrole-2,5-dione (19) (55 mg, 45%) as an orange solid. $^1$H NMR (DMSO-d6, 400 MHz) 3.87 (s, 3H), 6.87 (d, J=7.3 Hz, 1H), 6.94 (dt, J=0.8, 7.9 Hz, 1H), 6.98 (d, J=1.9 Hz, 1H), 7.18 (dd, J=1.9, 6.6 Hz, 1H), 7.25 (m, 1H), 7.45 (d, J=8.5 Hz, 1H), 7.64 (d, J=8.5 Hz, 1H), 11.22 (s, 1H); $^{13}$C NMR (DMSO-d6, 75 MHz) 33.6, 103.8, 111.7, 111.8, 112.8, 113.2, 121.8, 123.2, 124.9, 125.3, 125.7, 127.5, 135.9, 147.4, 154.7, 172.1, 172.4. FAB-HRMS calcd for C$_{21}$H$_{13}$BrN$_2$O$_4$+Na$^+$: 443.0002; found: 443.0001.

3-(5-Fluoro-benzofuran-3-yl)-4-(1H-indol-3-yl)-pyrrole-2,5-dione (2)

The general procedure of Method A was followed using 5-fluoro-benzofuran-3-one for synthesis of 2-(5-fluoro-benzofuran-3-yl)-acetamide. $^1$H NMR (DMSO-d6, 400 MHz) 6.52 (dd, J=2.5, 8.9 Hz, 1H), 6.81 (t, J=7.4 Hz, 1H), 6.89 (dt, J=2.6, 8.9 Hz, 1H), 6.59 (d, J=8.0 Hz, 1H), 7.12 (m, 1H), 7.84 (s, 1H), 7.89 (d, J=2.7 Hz, 1H), 8.16 (s, 1H), 8.81 (s, 1H); 3.88 (s, 3H), 6.21 (d, J=8.1 Hz, 1H), 6.62 (t, J=8.1 Hz, 1H), 7.02-7.08 (m, 2H), 7.34 (t, J=8.1 Hz, 1H), 7.43 (d, J=8.1 Hz, 1H), 7.54-7.59 (m, 2H), 8.45 (s, 1H), 11.14 (s, 1H), 13.38 (s, 1H). $^{13}$C NMR (DMSO-d6, 75 MHz) 33.2, 104.3, 110.6, 120.3, 120.9, 121.5, 122.2, 125.3, 126.4, 135.3, 137.1, 172.2, 172.4. FAB-HRMS calcd for C$_{20}$H$_{11}$FN$_2$O$_3$+Na$^+$: 369.0646; found: 369.0644.

3-(5-Bromo-benzofuran-3-yl)-4-(1-methyl-1H-indol-3-yl)-pyrrole-2,5-dione (3)

The general procedure of Method A was followed using 5-bromo-benzofuran-3-one for synthesis of 2-(5-bromo-benzofuran-3-yl)-acetamide. $^1$H NMR (DMSO-d6, 400 MHz) 3.87 (s, 3H), 6.63 (t, J=7.0 Hz, 1H), 6.79 (d, J=8.0 Hz, 1H), 6.98 (m, 2H), 7.21 (dd, J=1.9, 8.8 Hz, 1H), 7.35 (m, 2H), 7.2 (s, 1H), 8.07 (s, 1H), 9.81 (s, 1H); $^{13}$C NMR (DMSO-d6, 75 MHz) 32.6, 104.4, 110.1, 111.7, 112.9, 115.1, 120.2, 120.9, 122.2, 122.3, 125.0, 125.8, 127.4, 127.8, 133.1, 134.1, 137.2, 148.2, 153.5, 171.0, 171.3. FAB-HRMS calcd for C$_{21}$H$_{13}$BrN$_2$O$_3$+Na$^+$: 443.0002; found: 442.9998.

3-(7-Methoxy-benzofuran-3-yl)-4-(1-methyl-1H-indol-3-yl)-pyrrole-2,5-dione (4)

The general procedure of Method A was followed using 7-methoxy-benzofuran-3-one for synthesis of 2-(7-methoxybenzofuran-3-yl)-acetamide. $^1$H NMR (DMSO-d6, 400 MHz) 3.88 (s, 3H), 3.91 (s, 3H), 6.47 (dd, J=3.8, 8.8 Hz, 1H), 6.75 (t, J=7.5 Hz, 1H), 6.85 (m, 2H), 7.09 (t, J=7.5 Hz, 1H), 7.46 (d, J=7.5 Hz, 1H), 7.97 (s 1H), 8.22 9s, 1H), 11.17 (s, 1H); $^{13}$C NMR (DMSO-d6, 75 MHz) 333.4, 56.1, 104.2, 107.3, 110.9, 112.2, 114.0, 120.6, 121.1, 122.2, 122.5, 123.9, 125.9, 127.6, 133.1, 134.7, 137.1, 143.8, 145.3, 147.2. FAB-HRMS calcd for $C_{22}H_{16}N_2O_4$+Na$^+$: 395.1002; found: 395.1001.

3-Benzofuran-3-yl-4-(5-fluoro-1H-indol-3-yl)-pyrrole-2,5-dione (5)

The general procedure of Method A was followed using 2-benzofuran-3-yl-acetamide and (5-fluoro-1H-indol-3-yl)-oxo-acetic acid ethyl ester. $^1$H NMR (DMSO-d6, 400 MHz) 6.59 (dd, J=2.3, 10.4 Hz, 1H), 6.83-6.94 (m, 3H), 7.23 (t, J=7.4 hz, 1H), 7.41 (dd, J=4.7, 8.8 Hz, 1H), 7.62 (d, J=8.3 Hz, 1H), 7.93 (s, 1H), 8.30 (s, 1H), 11.2 (s, 1H), 11.97 (s, 1H); $^{13}$C NMR (DMSO-d6, 100 MHz) 105.42, 105.46, 105.8, 106.0, 220.5, 110.7, 111.6, 111.8, 113.5, 113.6, 121.9, 123.0, 123.2, 125.2, 125.7, 126.0, 126.1, 132.6, 133.1, 133.2, 147.5, 154.6, 156.2, 158.5, 172.2, 172.5. FAB-HRMS calcd for $C_{20}H_{11}FN_2O_3$+Na$^+$: 369.0646; found: 369.0641.

3-Benzofuran-3-yl-4-(5-fluoro-1-methyl-1H-indol-3-yl)-pyrrole-2,5-dione (6)

The general procedure of Method A was followed using 2-benzofuran-3-yl-acetamide and (5-fluoro-1-methyl-1H-indol-3-yl)-oxo-acetic acid ethyl ester. $^1$H NMR (DMSO-d6, 400 MHz) 3.88 (s, 3H), 6.51 (dd, J=2.3, 10.0 Hz, 1H), 6.93 (m, 3H), 7.24 (t, J=7.1 hz, 1H), 7.48 (dd, J=4.5, 9.0 Hz, 1H), 7.63 (d, J=8.2 Hz, 1H), 8.03 (s, 1H), 8.8 (s, 1H), 11.21 (s, 1H); $^{13}$C NMR (DMSO-d6, 100 MHz) 33.7, 104.2, 1104.3, 106.0, 106.3, 110.4, 110.7, 111.7 111.8, 112.1, 112.2, 121.9, 122.6, 123.2, 125.3, 125.8, 126.3, 126.4, 132.7, 133.9, 136.2, 147.5, 154.6, 156.4, 158.7, 172.1, 172.5. FAB-HRMS calcd for $C_{21}H_{13}FN_2O_3$+Na$^+$: 383.0802; found: 383.0802.

3-(5-Fluoro-1-methyl-1H-indol-3-yl)-4-(6-hydroxymethyl-benzofuran-3-yl)-pyrrole-2,5-dione (7). See Scheme 9

Acetic acid 3-methoxy-benzyl ester. To a solution of (3-methoxy-phenyl)-methanol (14.15 g, 102.4 mmol) and triethylamine (32.8 mL, 235.6 mmol) in dry dichloromethane (45 mL) dimethylaminopyridine (1.3 g, 10.2 mmol) and acetic anhydride (11.1 mL, 118.0 mmol) was added at 0° C. and the reaction mixture was allowed to warm to room temperature and stirred overnight. The reaction mixture was diluted with EtOAc and washed with 1N HCl solution. The organic solution was dried over Na$_2$SO$_4$, evaporated in vacuo and purified by column chromatography (ethyl acetate:hexane; 5:95) to give the acetic acid 3-methoxy-benzyl ester as a slightly yellow oil (17.84 g, 96%). $^1$H NMR (CDCl$_3$, 400 MHz) 2.08 (s, 3H), 3.78 (s, 3H), 5.06 (s, 2H), 6.85 (d, J=8.0 Hz, 1H), 6.89 (s, 1H), 6.92 (d, J=8.0 Hz, 1H), 7.25 (t, J=8.0 Hz, 1H), $^{13}$C NMR (CDCl$_3$, 100 MHz) 20.6, 54.8, 65.7, 113.30, 113.32, 120.0, 129.2, 137.1, 159.4, 170.4.

Acetic acid 4-(2-chloro-acetyl)-3-hydroxy-benzyl ester. To a solution of acetic acid 3-methoxy-benzyl ester (4.85 g, 26.9 mmol) in anhydrous dichloromethane (38 mL) chloroacetyl chloride (6.4 mL, 80.7 mmol) was added dropwise at 20° C. Subsequently, aluminum chloride (11.8 g, 88.8 mmol) was added in several portions while maintaining the temperature below 30° C. The resulting solution was heated to reflux for 16 h. The solution was cooled to room temperature and poured into ice water (300 mL). The resulting mixture was extracted with dichloromethane and the organic phase was washed with diluted NaHCO$_3$, dried over Na$_2$SO$_4$, and evaporated in vacuo. The residue was purified by column chromatography (ethylacetate:hexane; 1:9 to 1:1) to give the acetic acid 4-(2-chloro-acetyl)-3-hydroxy-benzyl ester as yellow oil (1.31 g, 20%). $^1$H NMR (CDCl$_3$, 400 MHz) 2.14 (s, 3H), 4.69 (s, 2H), 5.09 (s, 2H), 6.88 (d, J=8.0 Hz, 1H), 6.97 (s, 1H), 7.67 (d, J=8.0 Hz, 1H), 11.67 (s, 1H), $^{13}$C NMR (CDCl$_3$, 100 MHz) 20.8, 45.2, 64.8, 116.6, 117.1, 118.0, 129.9, 146.2, 162.9, 170.5, 196.2.

Acetic acid 3-oxo-2,3-dihydro-benzofuran-6-ylmethyl ester. A solution of acetic acid 4-(2-chloro-acetyl)-3-hydroxy-benzyl ester (2.20 g, 9.07 mmol) and sodium acetate (1.49 g, 18.13 mmol) in anhydrous methanol (40 mL) was heated to reflux for 2 h. The reaction mixture was allowed to cool to RT, and concentrated. The residue was dissolved in dichloromethane and washed with water. The aqueous phase was extracted with dichloromethane. The combined organic layers were dried over Na$_2$SO$_4$, evaporated in vacuo, and the residue was purified by column chromatography (ethylacetate:hexane; 2:8) to give the acetic acid 3-oxo-2,3-dihydro-benzofuran-6-ylmethyl ester as an off white solid (1.29 g, 59%). $^1$H NMR (CDCl$_3$, 400 MHz) 2.17 (s, 3H), 4.65 (s, 2H), 5.17 (s, 2H), 7.06 (d, J=8.0 Hz, 1H), 7.13 (s, 1H), 7.67 (d, J=8.0 Hz, 1H), 11.67 (s, 1H), $^{13}$C NMR (CDCl$_3$, 100 MHz) 20.8, 65.3, 75.1, 112.3, 120.8, 121.2, 124.2, 146.9, 170.5, 174.2, 199.2.

(6-Acetoxymethyl-benzofuran-3-yl)-acetic acid ethyl ester. To a solution of acetic acid 3-oxo-2,3-dihydro-benzofuran-6-ylmethyl ester (1.50 g, 7.27 mmol) in toluene (260 mL) was added (caboxymethylene)triphenyl phosphorane (12.67 g, 36.37 mmol) and the mixture was refluxed for 24 h. The reaction mixture was allowed to cool to room temperature and concentrated. The residue was purified by column chromatography (ethylacetate:hexane; 5:95) to give the (6-acetoxymethyl-benzofuran-3-yl)-acetic acid ethyl ester as a off white solid (1.15 g, 57%). $^1$H NMR (CDCl$_3$, 400 MHz) 1.27 (t, J=7.1 Hz, 3H), 2.11 (s, 3H), 3.69 (s, 2H), 4.19 (q, J=7.1 Hz, 2H), 5.21 (s, 2H), 7.26 (d, J=8.0 Hz, 1H), 7.50 (s, 1H), 7.56 (d, J=8.0 Hz, 1H), 7.65 (s, 1H), $^{13}$C NMR (CDCl$_3$, 100 MHz) 14.2, 21.0, 29.9, 61.1, 66.4, 111.6, 113.1, 119.8, 123.1, 127.7, 132.6, 143.5, 155.2, 170.5, 170.9.

2-(6-Hydroxymethyl-benzofuran-3-yl)-acetamide. (6-Acetoxymethyl-benzofuran-3-yl)-acetic acid ethyl ester (0.80 g, 2.90 mmol) was added to liquid ammonia at −78° C., the reaction flask was sealed and heated at 60° C. for 6 days. The reaction mixture was cooled, the excess of ammonia was allowed to evaporate and the residue was washed with in hexane and precipitated to give the 2-(6-hydroxymethyl-benzofuran-3-yl)-acetamide as an off white solid (0.54 g, 90%). $^1$H NMR (DMSO-d6, 400 MHz) 3.46 (s, 2H), 4.60 (d, J=5.6 Hz, 1H), 5.25 (t, J=5.6 Hz, 1H), 6.98 (brs, 1H), 7.20 (d, J=8.0 Hz, 1H), 7.47 (s, 1H), 7.53 (brs, 1H), 7.56 (d, J=8.0 Hz, 1H), 7.77 (s, 1H), $^{13}$C NMR (DMSO-d6, 400 MHz) 30.8, 63.4, 109.4, 115.4, 120.0, 121.6, 127.0, 139.9, 143.4, 155.2, 171.7.

2-[6-(tert-Butyl-diphenyl-silanyloxymethyl)-benzofuran-3-yl]-acetamide. To a solution of 2-(6-hydroxymethyl-benzofuran-3-yl)-acetamide (0.90 g, 4.39 mmol) in a mixture of dichloromethane (30 mL) and dimethylformamide (8 mL) was added imidazole (0.36 g, 5.26 mmol) and tert-butyl-diphenylchlorosilane (1.37 mL, 5.26 mmol), and the mixture was stirred for 5 h at room temperature. The reaction was quenched with methanol and stirred for 10 minutes. The reaction mixture was concentrated in vacuo and the residue was purified by column chromatography (methanol:dichloromethane; 5:95) to give the 2-[6-(tert-butyl-diphenyl-silanyloxymethyl)-benzofuran-3-yl]-acetamide as an off white solid (1.61 g, 82%). $^1$H NMR (DMSO-d6, 400 MHz) 1.04 (s, 9H), 3.47 (s, 2H), 4.88 (s, 2H), 6.98 (brs, 1H), 7.22 (d, J=8.0 Hz, 1H), 7.40-7.55 (m, 9H), 7.65 (d, J=7.2 Hz, 1H), 7.80 (s, 1H).

To a solution of the 2-[6-(tert-butyl-diphenyl-silanyloxymethyl)-benzofuran-3-yl]-acetamide (0.36 g, 0.81 mmol) and (5-fluoro-1-methyl-1H-indol-3-yl)-oxo-acetic acid ethyl ester (0.20 g, 0.81 mmol) in dry THF (8 mL) was added a 1.0 M solution of potassium tert-butoxide in THF (6.49 mL) at 0° C. The reaction was stirred for 30 min, allowed to warm to room temperature and stirred for additional 30 min. The reaction was quenched with water, and diluted with EtOAc. The organic solution was washed with brine, then dried over $Na_2SO_4$ and concentrated. The residue was dissolved in THF and a 1.0 M solution of TBAF in THF (1.22 mL) was added at room temperature. The mixture was stirred for 2 h. The solution was quenched with $NH_4Cl$ and stirred for 5 min. The solvent was removed and the residue was dissolved in dichloromethane and washed twice with water and brine. The organic phase was dried over $Na_2SO_4$ and concentrated. The residue was purified by column chromatography (methanol:dichloromethane; 5:95 to 1:9) to give the 3-(5-fluoro-1-methyl-1H-indol-3-yl)-4-(6-hydroxymethyl-benzofuran-3-yl)-pyrrole-2,5-dione as an orange solid (0.23 g, 72%). $^1$H NMR (DMSO-d6, 400 MHz) 3.88 (s, 3H), 4.52 (d, J=5.7 Hz, 2H), 5.24 (t, J=5.7 Hz, 1H), 6.53 (dd, J=2.3, 10.3 Hz, 1H), 6.84 (d, J=8.1 Hz, 1H), 6.89 (d, J=8.2 Hz, 1H), 6.95 (dt, J=2.4, 9.1 Hz, 1H), 7.49 (dd, J=4.5, 9.5 Hz, 1H), 7.54 (s, 1H), 8.02 (s, 1H), 8.24 (s, 1H), 11.19 (s, 1H). $^{13}$C NMR (DMSO-d6, 100 MHz) 33.7, 63.1, 104.27, 104.31, 103.1, 106.3, 109.4, 110.5, 110.8, 111.7, 112.2, 112.3, 121.5, 121.9, 122.9, 124.5, 126.4, 126.5, 132.6, 133.9, 136.2, 140.6, 147.4, 154.9, 156.5, 172.2, 172.5.

3-(5-Fluoro-1-methyl-1H-indol-3-yl)-4-(6-methoxymethyl-benzofuran-3-yl)-pyrrole-2,5-dione (8). 2-(6-Methoxymethyl-benzofuran-3-yl)-acetamide To a solution of 2-(6-hydroxymethyl-benzofuran-3-yl)-acetamide (0.10 g, 0.49 mmol) in DMF (6 mL) was added sodium hydride (0.023 g, 0.053 mmol) and methyl iodide (0.033 mL, 0.053 mmol) at 0° C. The reaction mixture was allowed to warm to room temperature, stirred for 45 min and quenched with addition of water. The mixture was diluted with EtOAc and washed with brine. The aqueous phase was extracted with EtOAc. The combined organic layers were dried over $Na_2SO_4$ and evaporated in vacuo. The residue was purified by preparative TLC (diethyl ether) to afford product (0.030 g, 28%) as a white solid. $^1$H NMR (DMSO-d6, 400 MHz) 3.29 (s, 3H), 3.46 (s, 2H), 4.50 (s, 2H), 6.97 (brs, 1H), 7.21 (d, J=8.0 Hz, 1H), 7.48 (s, 1H), 7.53 (brs, 1H), 7.59 (d, J=8.0 Hz, 1H), 7.80 (s, 1H). $^{13}$C NMR (DMSO-d6, 400 MHz) 30.7, 57.8, 74.1, 110.7, 115.4, 120.3, 122.7, 127.7, 135.3, 143.8, 155.0, 171.7.

3-(5-Fluoro-1-methyl-1H-indol-3-yl)-4-(6-methoxymethyl-benzofuran-3-yl)-pyrrole-2,5-dione The general procedure was followed. $^1$H NMR (CDCl$_3$, 400 MHz) 3.33 (s, 3H), 3.86 (s, 3H), 4.48 (s, 2H), 6.64 (dd, J=2.2, 9.8 Hz, 1H), 6.81-6.90 (m, 3H), 7.21 (dd, J=4.5, 8.9 Hz, 1H), 7.39 (brs, 1H), 7.49 (s, 1H), 7.79 (s, 1H), 8.12 (s, 1H). $^{13}$C NMR (CDCl$_3$, 100 MHz) 33.7, 57.9, 74.4, 104.9, 107.0, 107.2, 110.4, 110.5, 110.8, 111.0, 111.3, 111.4, 121.8, 122.6, 123.3, 124.7, 126.3, 131.9, 133.6, 135.0, 135.5, 147.5, 155.1, 157.0, 170.5, 171.1.

3-(5-Fluoro-1-methyl-1H-indol-3-yl)-4-(6-hydroxybenzofuran-3-yl)-pyrrole-2,5-dione (9). 6-(tert-Butyl-diphenyl-silanyloxy)-benzofuran-3-one To a solution of 6-hydroxy-benzofuran-3-one (1.01 g, 6.73 mmol) in dry dichloromethane (18 mL) was added imidazole (0.458 g, 6.727 mmol) followed by tert-butyldiphenylchlorosilane (1.72 mL, 6.73 mmol) at room temperature. The mixture was stirred overnight and poured into brine. The aqueous phase was extracted with dichloromethane. The combined organic layers were dried over $Na_2SO_4$, evaporated in vacuo and the residue was purified by column chromatography (ethylacetate:hexane; 1:9) to give the 6-(tert-butyl-diphenyl-silanyloxy)-benzofuran-3-one as slightly yellow oil (1.34 g, 52%). $^1$H NMR (CDCl$_3$, 400 MHz) 1.21 (s, 9H), 4.54 (s, 2H), 6.40 (s, 1H), 6.55 (dd, J=1.6, 8.0 Hz, 1H), 7.38-7.50 (m, 7H), 7.67 (m, 4H).

[6-(tert-Butyl-diphenyl-silanyloxy)-benzofuran-3-yl]-acetic acid ethyl ester. Using the standard procedure the mixture was refluxed until reaction completion (3 days) to give the [6-(tert-butyl-diphenyl-silanyloxy)-benzofuran-3-yl]-acetic acid ethyl ester as yellow oil with 45% yield. $^1$H NMR (CDCl$_3$, 300 MHz) 1.12 (s, 9H), 1.26 (t, J=7.2 Hz, 3H), 3.61 (s, 2H), 4.18 (q, J=7.2 Hz, 2H), 6.40 (s, 1H), 6.55 (dd, J=1.6, 8.0 Hz, 1H), 7.38-7.50 (m, 7H), 7.67 (m, 4H).

2-(6-Hydroxy-benzofuran-3-yl)-acetamide. Using the standard procedure the 2-(6-hydroxy-benzofuran-3-yl)-acetamide was obtained as an off white solid with 88% yield. During the reaction the silyl protective group was cleaved. $^1$H NMR (CD$_3$OD, 400 MHz) 3.56 (s, 2H), 6.76 (dd, J=1.8, 8.0 Hz, 1H), 6.86 (d, J=2.0 Hz, 1H), 7.39 (d, J=8.0 Hz, 1H), 7.52 (s, 1H).

2-[6-(tert-Butyl-diphenyl-silanyloxy)-benzofuran-3-yl]-acetamide. To a solution of 2-(6-hydroxy-benzofuran-3-yl)-acetamide (0.23 g, 1.20 mmol) in a mixture of dry dichloromethane (20 mL) and DMF (6 mL) was added imidazole (0.34 g, 5.05 mmol), followed by tert-butyldiphenylchlorosilane (1.31 mL, 5.05 mmol) at room temperature and the mixture was stirred for two days. The solution was quenched with methanol and stirred for 10 min. The solvent was evaporated in vacuo and the residue was purified by column chromatography (methanol:dichloromethane; 5:95) to give the 2-[6-(tert-butyl-diphenyl-silanyloxy)-benzofuran-3-yl]-acetamide as a white solid (0.40 g, 78%). $^1$H NMR (DMSO-d6, 400 MHz) 1.06 (s, 9H), 3.38 (s, 2H), 6.74 (dd, J=1.8, 8.4 Hz, 1H), 6.80 (d, J=1.8 Hz, 1H), 7.40 (d, J=8.4 Hz, 1H), 7.42-7.54 (m, 7H), 7.64 (s, 1H), 7.70 (m, 4H), 7.80 (s, 1H).

3-(5-Fluoro-1-methyl-1H-indol-3-yl)-4-(6-hydroxy-benzofuran-3-yl)-pyrrole-2,5-dione The procedure used to synthesize FG1-059 (7) was followed. $^1$H NMR (DMSO-d6, 400 MHz) 3.88 (s, 3H), 6.39 (dd, J=2.0, 8.5 Hz, 1H), 6.54 (dd, J=2.2, 10.5 Hz, 1H), 6.61 (d, J=8.5 Hz, 1H), 6.92 (d, J=1.8 Hz, 1H), 6.95 (dt, J=2.0, 8.5 Hz, 1H), 7.49 (dd, J=4.5, 9.0 Hz, 1H), 7.98 (s, 1H), 8.09 (s, 1H), 9.58 (s, 1H), 11.16 (s, 1H). $^{13}$C NMR (DMSO-d6, 100 MHz) 33.8, 98.0, 104.3, 104.4, 106.2, 106.4, 110.5, 110.7, 111.7, 112.1, 112.2, 112.7, 117.8, 122.1, 123.1, 126.5, 126.6, 132.2, 133.9, 136.1, 145.9, 155.9, 156.1, 156.5, 158.8, 172.2, 172.6.

3-(5-Fluoro-6-iodo-1-methyl-1H-indol-3-yl)-4-(7-methoxy-benzofuran-3-yl)-pyrrole-2,5-dione. (10) 2-Fluoro-4-methyl-5-nitro-phenylamine To a concentrated sulfuric acid (15.0 mL) 2-fluoro-4-methylaniline (1.80 mL, 16.0 mmol) was added dropwise at 0° C. The mixture was stirred until a clear solution formed. To the obtained solution concentrated nitric acid (68-70%) (5.14 mL) was added dropwise while maintaining the bath temperature at −10° C. The mixture was stirred at −10° C. for 30 min and poured into ice water. The resulting mixture was extracted with EtOAc. The combined EtOAc extracts were washed with NaHCO$_3$, brine, dried over MgSO$_4$, filtered and concentrated. The residue was purified by column chromatography (ethyl acetate:hexane; 1:9) to afford 2-fluoro-4-methyl-5-nitro-aniline as a yellow solid (2.30 g, 85%). $^1$H NMR (CDCl$_3$, 400 MHz,): 2.50 (s, 3H), 3.92 (br. s, 2H), 6.93 (d, J=11.2 Hz, 1H), 7.51 (d, J=8.2 Hz, 1H). $^{13}$C NMR (CDCl$_3$, 100 MHz): 20.0, 113.0, 118.7, 124.9, 133.3, 153.3.

1-Fluoro-2-iodo-5-methyl-4-nitro-benzene. 2-Fluoro-4-methyl-5-nitro-aniline (1.30 g, 7.64 mmol) was suspended in concentrated hydrochloric acid (4 mL) and cooled to 0° C. Solution of sodium nitrite (0.58 g, 8.40 mmol) in water (2.6 mL) was added dropwise while maintaining the temperature at 0-5° C. After stirring for 15 min, the mixture was filtered through a cotton pad and slowly poured into a solution of potassium iodide (4.44 g, 26.7 mmol) in water (16 mL). After standing overnight, the reaction mixture was diluted with EtOAc, washed with 10% aq NaOH and 5% aq Na$_2$S$_2$O$_5$ successively, dried over MgSO$_4$, filtered, and concentrated. The residue was purified by column chromatography (ethyl acetate:hexane; 2:98) to afford 1-iodo-2-fluoro-4-methyl-5-nitro-benzene as a colorless oil (1.60 g, 74%). $^1$H NMR (CDCl$_3$, 400 MHz,): 2.61 (s, 3H), 7.05 (d, J=8.0 Hz, 1H), 8.44 (d, J=5.8 Hz, 1H). $^{13}$C NMR (CDCl$_3$, 100 MHz,): 20.7, 119.1, 136.2, 137.3, 145.7, 163.9.

[2-(5-Fluoro-4-iodo-2-nitro-phenyl)-vinyl]-dimethyl-amine. A mixture of N,N-dimethylformamide dimethyl acetal (0.30 mL, 2.31 mmol) and 1-iodo-2-fluoro-4-methyl-5-nitro-benzene (0.50 g, 1.78 mmol) in dry DMF (3.0 mL) was stirred at 125° C. for 3 h. The resulting mixture was partitioned between EtOAc and water. The organic layer was washed with brine, dried over MgSO$_4$, filtered, and concentrated. The residue was washed with hexane to give [2-(4-iodo-5-fluoro-2-nitro-phenyl)-vinyl]-dimethyl-amine as dark red solid (0.37 mg, 62%). $^1$H NMR (CDCl$_3$, 400 MHz): 2.97 (s, 6H), 5.92 (d, J=13.3 Hz, 1H), 7.02 (d, J=13.3 Hz, 1H), 7.09 (d, J=10.2 Hz, 1H), 8.30 (d, J=6.2 Hz, 1H). $^{13}$C NMR (CDCl$_3$, 100 MHz,): 40.8, 108.9, 109.1, 137.0, 139.3, 146.0.

5-Fluoro-6-iodo-1H-indole. The enamine (0.37 g, 1.10 mmol) was dissolved in EtOH (8.0 mL). To this solution Fe (0.73 g, 13.20 mmol) and acetic acid (8.0 mL) were added and the mixture was stirred at 90° C. for 2 h. The resulting mixture was filtered through Celite pad and concentrated. The residue was purified by column chromatography (ethyl acetate-hexane; 1:9) to afford 5-fluoro-6-iodo-1H-indole as a yellow solid (0.10 g, 35%). $^1$H NMR (CDCl$_3$, 400 MHz): 6.52 (m, 1H), 7.24 (m, 1H), 7.35 (d, J=8.6 Hz, 1H), 7.76 (d, J=5.0 Hz, 1H), 8.14 (br. s, 1H). $^{13}$C NMR (CDCl$_3$, 100 MHz): 74.1, 102.9, 105.6, 120.6, 126.4, 128.6, 133.7, 156.0.

5-Fluoro-6-iodo-1-methyl-1H-indole. To a solution of 6-iodo-5-fluoro-1H-indole (0.495 g, 1.890 mmol) in dry DMF (7.0 mL) was added sodium hydride (55% suspension in oil) (0.124 g, 2.840 mmol) at 0° C. The mixture was stirred at 0° C. for 30 min, and then iodomethane (0.15 mL, 2.47 mmol) was added. The mixture was stirred for 1 hour at room temperature, and then quenched with ice and extracted with EtOAc (50 mL). The organic layer was washed with water, brine, dried over MgSO$_4$, filtered, and concentrated. The residue was purified by column chromatography (EtOAc-hexane, 1:9) to afford 5-fluoro-6-iodo-1-methyl-1H-indole as a colorless solid (0.50 g, 96%).

(5-Fluoro-6-iodo-1-methyl-1H-indol-3-yl)-oxo-acetic acid methyl ester. To a solution of 5-fluoro-6-iodo-1-methyl-1H-indole (0.25 g, 0.91 mmol) in Et$_2$O (7.0 mL) cooled to 0° C. a 2.0 M solution of oxalyl chloride in dichloromethane (1.14 mL, 2.28 mmol) was added dropwise. The reaction was stirred for 0.5 h at 0° C. and allowed to warm to room temperature and stirred overnight. The mixture was cooled to −20° C. and MeOH was added. The reaction was quenched with water and diluted with EtOAc. The organic layer was separated, dried over Na$_2$SO$_4$ and concentrated. The residue was purified by column chromatography (ethyl acetate-hexane, 1:3) to give the product (0.27 g, 82%). $^1$H NMR (CDCl$_3$, 300 MHz,): 3.85 (s, 3H), 3.96 (s, 3H), 7.70 (d, J=4.9 Hz, 1H), 8.09 (d, J=8.5 Hz, 1H), 8.34 (s, 1H), $^{13}$C NMR (CDCl$_3$, 75 MHz): 34.6, 53.3, 108.6, 113.0, 120.5, 128.5, 135.3, 141.9, 158.9, 163.2, 176.8.

To a solution of (5-Fluoro-6-iodo-1-methyl-1H-indol-3-yl)-oxo-acetic acid methyl ester (0.200 g, 0.554 mmol) and 7-O-methyl-bezofuran-3-acetamide (0.114 g, 0.554 mmol) in dry THF (5.0 mL) a 1.0 M solution of t-BuOK in THF (2.22 mL) was added dropwise at 0° C. After 1.5 h the obtained mixture was diluted with EtOAc, and washed with brine, dried over Mg MgSO$_4$, filtered, and concentrated. The residue was purified by column chromatography (ethyl acetate-hexane, 1:2) to give the product (0.15 g, 52%). $^1$H NMR (CDCl$_3$, 400 MHz,): 3.83 (s, 3H), 4.02 (s, 3H), 6.42 (d, J=7.9 Hz, 1H), 6.73 (d, J=7.5 Hz, 1H), 6.76 (d, J=9.0 Hz, 1H), 6.83 (t, J=7.9 Hz, 1H), 7.67 (m, 2H), 7.73 (s, 1H), 8.16 (s, 1H). $^{13}$C NMR (CDCl$_3$, 100 MHz,): 33.8, 56.1, 104.9, 107.0, 107.1, 111.5, 114.0, 119.7, 123.7, 123.9, 126.7, 126.9, 131.4, 134.8, 135.3, 144.5, 145.4, 147.3, 156.3, 170.3, 170.9. FAB-HRMS calcd for C$_{22}$H$_{14}$N$_2$O$_4$Fl+Na$^+$: 538.98748; found: 538.98659.

3-(6-Bromo-5-fluoro-1-methyl-1H-indol-3-yl)-4-(7-methoxy-benzofuran-3-yl)-pyrrole-2,5-dione (11). 1-Bromo-2-fluoro-4-methyl-5-nitro-benzene 2-Fluoro-4-methyl-5-nitro-aniline (1.85 g, 10.90 mmol) was suspended in concentrated hydrobromic acid (22 mL) and cooled to 0° C. Solution of sodium nitrite (0.83 g, 12.00 mmol) in water (3.6 mL) was added dropwise while maintaining the temperature at 0~5° C. After stirring for 15 min, the mixture was filtered through a cotton pad and slowly poured into a solution of cuprous oxide (2.60 g, 17.5 mmol) and concentrated hydrobromic acid (20 mL) at 0° C. After stirring overnight, the reaction mixture was diluted with EtOAc, washed with 10% aq NaOH and 5% aq Na$_2$S$_2$O$_5$ successively, dried over MgSO$_4$, filtered and concentrated. The residue was purified by column chromatography (ethyl acetate:hexane; 2:98) to afford 1-Bromo-2-fluoro-4-methyl-5-nitro-benzene as a colorless oil (2.30 g, 91%). $^1$H NMR (CDCl$_3$, 400 MHz,): 2.59 (s, 3H), 7.11 (d, J=8.4 Hz, 1H), 8.24 (d, J=6.3 Hz, 1H).

[2-(4-Bromo-5-fluoro-2-nitro-phenyl)-vinyl]-dimethyl-amine. A mixture of N,N-dimethylformamide diisopropyl acetal (1.32 mL, 6.31 mmol) and 1-bromo-2-fluoro-4-methyl-5-nitro-benzene (1.23 g, 5.26 mmol) in dry DMF (15.0 mL) was stirred at 125° C. for 3 h. The resulting mixture was partitioned between EtOAc and water. The organic layer was washed with brine, dried over MgSO$_4$, filtered, and concentrated. The residue was washed with hexane to give [2-(4-bromo-5-fluoro-2-nitro-phenyl)-vinyl]-dimethyl-amine as dark red solid (1.89 mg, 83%). $^1$H NMR (CDCl$_3$, 400 MHz): 2.92 (s, 6H), 5.88 (d, J=12.3 Hz, 1H), 6.98 (d, J=13.2 Hz, 1H), 7.11 (d, J=10.8 Hz, 1H), 8.10 (d, J=6.9 Hz, 1H).

6-Bromo-5-fluoro-1H-indole. The enamine (1.89 g, 4.38 mmol) was dissolved in EtOH (35.0 mL). To this solution Fe (4.42 g, 79.0 mmol) and acetic acid (35.0 mL) were added and the mixture was stirred at 90° C. for overnight. The resulting mixture was filtered and concentrated. The residue was purified by column chromatography (ethyl acetate-hexane; 1:9) to afford 6-bromo-5-fluoro-1H-indole as a yellow solid (0.83 g, 89%). ¹H NMR (CDCl₃, 400 MHz): 6.52 (m, 1H), 7.27 (m, 1H), 7.38 (d, J=9.3 Hz, 1H), 7.57 (d, J=5.7 Hz, 1H), 8.18 (br. s, 1H).

6-Bromo-5-fluoro-1-methyl-1H-indole. To the solution of 6-bromo-5-fluoro-1H-indole (0.92 g, 4.28 mmol) in dry DMF (10 mL) was added sodium hydride as 60% in oil (0.26 g, 6.41 mmol) at 0° C. The mixture was stirred at 0° C. for 30 min, and then iodomethane (0.32 mL, 5.14 mmol) was added. The mixture was stirred for 1 hour at room temperature, and then quenched with ice and extracted with EtOAc (50 mL). The organic layer was washed with water, brine, dried over MgSO₄, filtered, and concentrated. The residue was purified by column chromatography (EtOAc-hexane, 1:9) give 6-bromo-5-fluoro-1-methyl-1H-indole as a colorless solid (0.97 g, 99%). ¹H NMR (CDCl₃, 400 MHz): 3.66 (s, 3H), 6.43 (d, J=2.7 Hz, 1H), 7.05 (d, J=2.7 Hz, 1H), 7.34 (d, J=9.3 Hz, 1H), 7.44 (d, J=5.4 Hz, 1H).

(6-Bromo-5-fluoro-1-methyl-1H-indol-3-yl)-oxo-acetic acid ethyl ester. To a solution of 6-bromo-5-fluoro-1-methyl-1H-indol (0.23 g, 1.00 mmol) in Et₂O (15.0 mL) cooled to 0° C. a 2.0 M solution of oxalyl chloride in dichloromethane (0.56 mL, 5.00 mmol) was added dropwise. The reaction was stirred for 0.5 h at 0° C. and allowed to warm to room temperature and stirred overnight. The mixture was cooled to −20° C. and dry EtOH (2 mL) was added. The reaction mixture was diluted with EtOAc, washed with water and brine, dried over Na₂SO₄ and concentrated. The residue was purified by column chromatography (ethyl acetate-hexane, 1:3) to give the product (0.21 g, 59%). ¹H NMR (CDCl₃, 300 MHz,): 1.43 (t, J=7.2 Hz, 3H), 3.82 (s, 3H), 4.40 (t, J=7.2 Hz, 2H), 7.47 (d, J=5.4 Hz, 1H), 8.08 (d, J=9.0 Hz, 1H), 8.30 (s, 1H).

3-(6-Bromo-5-fluoro-1-methyl-1H-indol-3-yl)-4-(7-methoxy-benzofuran-3-yl)-pyrrole-2,5-dione. To a solution of (6-bromo-5-fluoro-1-methyl-1H-indol-3-yl)-oxo-acetic acid ethyl ester (0.127 g, 0.387 mmol) and 7-O-methyl-bezofuran-3-acetamide (0.095 g, 0.465 mmol) in dry THF (5.0 mL) a 1.0 M solution of t-BuOK in THF (1.55 mL) was added dropwise at 0° C. After 1.5 h the obtained mixture was diluted with EtOAc, washed with brine, dried over Mg MgSO₄, filtered, and concentrated. The residue was purified by column chromatography (ethyl acetate-hexane, 1:2) to give the product (0.089 g, 49%). ¹H NMR (CDCl₃, 400 MHz,): ¹H NMR (CDCl₃, 400 MHz) 3.83 (s, 3H), 4.01 (s, 3H), 6.39 (d, J=8.3 Hz, 1H), 6.71-6.84 (m, 3H), 7.48 (d, J=6.0 Hz, 1H), 7.52 (s, 1H), 7.75 (s, 1H), 8.16 (s, 1H). ¹³C NMR (CDCl₃, 100 MHz) 33.8, 56.1, 96.1, 104.3, 104.5, 105.0, 105.1, 107.1, 107.8, 108.0, 111.5, 113.966, 114.0, 123.5, 123.9, 125.8, 125.9, 126.6, 131.4, 133.9, 135.2, 144.5, 145.5, 147.3, 152.9, 155.2, 170.2, 170.8.

3-Benzofuran-3-yl-4-(6-chloro-5-fluoro-1-methyl-1H-indol-3-yl)-pyrrole-2,5-dione (12)

¹H NMR (CDCl₃, 400 MHz) 3.81 (s, 3H), 6.75-6.80 (m, 2H), 6.87 (t, J=4.7 Hz, 1H), 7.20 (t, J=4.5 Hz, 1H), 7.31 (m, 2H), 7.50 (d, J=5.0 Hz, 1H), 7.73 (s, 1H), 8.14 (s, 1H). ¹³C NMR (CDCl₃, 100 MHz) 28.8, 105.0, 105.1, 107.8, 108.0, 111.0, 111.2, 111.5, 116.4, 116.6, 121.7, 122.7, 123.9, 124.9, 125.0, 128.9, 130.9, 131.2, 133.3, 135.1, 147.1, 152.0, 154.3, 154.8, 171.5, 171.9.

3-(6-Chloro-5-fluoro-1-methyl-1H-indol-3-yl)-4-(6-hydroxymethyl-benzofuran-3-yl)-pyrrole-2,5-dione (13)

¹H NMR (CDCl₃, 400 MHz) 3.83 (s, 3H), 4.67 (s, 2H), 6.75 (d, J=10 Hz, 1H), 6.77 (d, J=8.0 Hz, 1H), 6.87 (d, J=8.0 Hz, 1H), 7.33 (d, J=6.0 Hz, 1H), 7.52 (s, 1H), 7.77 (s, 1H), 8.14 (s, 1H). ¹³C NMR (CDCl₃, 100 MHz) 33.7, 64.4, 104.9, 105.0, 107.7, 107.9, 109.9, 111.0, 111.2, 116.4, 116.6, 121.6, 121.8, 123.9, 124.3, 125.0, 125.1, 131.2, 133.3, 135.0, 138.6, 147.3, 151.9, 154.3, 155.1, 11771.4, 171.8.

3-(6-Chloro-5-methoxy-1-methyl-1H-indol-3-yl)-4-(6-methoxy-benzofuran-3-yl)-pyrrole-2,5-dione (14)

¹H NMR (CD₃CN, 400 MHz) 4.33 (s, 3H), 4.39 (s, 3H), 7.07 (dd, J=1.2, 5.2 Hz, 1H), 7.21 (d, J=5.2 Hz, 1H), 7.34 (d, J=6.5 Hz, 1H), 7.67 (d, J=1.2 Hz, 1H), 8.12 (d, J=3.7 Hz, 1H), 8.37 (s, 1H), 8.64 (s, 1H), 9.25 (s, 1H). ¹³C NMR (CD₃CN, 100 MHz) 33.4, 55.48, 95.7, 104.8, 107.2, 107.5, 111.5, 111.9, 112.0, 115.2, 115.4, 118.5, 122.2, 124.5, 125.3, 131.8, 133.7, 135.9, 146.4, 153.9, 156.0, 158.5, 171.1, 171.5.

3-(6-Chloro-5-fluoro-1-methyl-1H-indol-3-yl)-4-(7-methoxy-benzofuran-3-yl)-pyrrole-2,5-dione (15)

¹H NMR (CDCl₃, 400 MHz) 3.82 (s, 3H), 4.00 (s, 3H), 6.38 (d, J=7.7 Hz, 1H), 6.71 (d, J=7.5 Hz, 1H), 6.80 (m, 2H), 7.31 (d, 1H), 7.52 (s, 1H), 7.74 (s, 1H), 8.16 (s, 1H). ¹³C NMR (CDCl₃, 100 MHz) 33.8, 56.0, 105.0, 107.0, 107.9, 108.2, 111.0, 111.5, 114.0, 123.6, 123.9, 126.6, 131.3, 133.3, 135.1, 144.4, 145.4, 147.2, 170.1, 170.8.

3-(6-Chloro-5-methoxy-1-methyl-1H-indol-3-yl)-4-(6-cyclobutylmethoxy-benzofuran-3-yl)-pyrrole-2,5-dione (16)

¹H NMR (CD₃CN, 400 MHz) 1.84-1.88 (m, 4H), 1.95-1.99 (m, 2H), 2.75 (m, 1H), 3.83 (s, 3H), 3.93 (d, J=7.1 Hz, 2H), 6.47 (dd, J=2.1, 8.8 Hz, 1H), 6.62 (d, J=8.8 Hz, 1H), 6.77 (d, J=10.6 Hz, 1H), 7.08 (d, J=2.1 Hz, 1H), 7.54 (d, J=7.3 Hz, 1H), 7.81 (s, 1H), 7.81 (s, 1H), 8.08 (s, 1H), 8.7 (s, 1H). ¹³C NMR (CD₃CN, 100 MHz) 18.1, 24.4, 33.2, 34.4, 72.3, 96.2, 107.0, 107.3, 111.4, 111.7, 112.3, 115.0, 115.2, 118.3, 122.0, 124.2, 125.1, 125.2, 131.5, 133.5, 135.7, 146.2, 153.7, 155.8, 157.8, 170.9, 171.3.

3-(6-Chloro-5-methoxy-1-methyl-1H-indol-3-yl)-4-(6-cyclopropylmethoxy-benzofuran-3-yl)-pyrrole-2, 5-dione (17)

¹H NMR (CD₃CN, 400 MHz) 0.32 (m, 2H), 0.60 (m, 2H), 1.21 (m, 1H), 3.80 (d, J=7.0 Hz, 2H), 3.84 (s, 3H), 6.48 (dd, J=2.2, 8.7 Hz, 1H), 6.63 (d, J=8.7 Hz, 1H), 6.70 (d, J=10.5 Hz, 1H), 7.07 (d, J=2.0 Hz, 1H), 7.56 (d, J=6.3 Hz, 1H), 7.82 (s, 1H), 8.08 (s, 1H), 8.70 (s, 1H). ¹³C NMR (CD₃CN, 100 MHz) 2.6, 10.0, 33.4, 73.1, 96.4, 99.6, 107.3, 107.5, 111.5, 111.9, 112.5, 122.2, 125.3, 134.0, 135.9, 146.4, 153.6, 156.0, 157.8, 158.9, 171.1, 171.8.

3-[6-(4-Chlorophenyl)-5-fluoro-1-methyl-1H-indol-3-yl]-4-(7-methoxy-benzofuran-3-yl)-pyrrole-2,5-dione (18)

3-(5-Fluoro-6-iodo-1-methyl-1H-indol-3-yl )-4-(7-methoxy benzofuran-3-yl)-pyrrole-2,5-dione (0.020 g, 0.039 mmol), Pd(PPh₃)₄ (4.5 mg, 0.004 mmol), and 4-chloro-phenylboronic acid (15.1 mg, 0.097 mmol) were dissolved in dimethoxy ethane (DME) (4 mL), and the mixture was degassed for 1 min and stirred for 10 min at room temperature. A solution of K₂CO₃ (2 M, 0.049 mL, 0.098 mmol) was added. The mixture was degassed again for 1 min, and stirred at 85° C. overnight. The resulting mixture was cooled to ambient temperature and poured into a mixture of 0.1 N HCl/EtOAc (15 mL/15 mL). After partition, the organic layer was washed with water, filtered, and concentrated. The residue was purified by preparative TLC using (ethyl acetate-hexane, 1:1) to afford the product as an orange solid (10 mg, 51%). The sample was purified by HPLC to give 3 mg of pure final compound.

$^1$H NMR (CDCl$_3$, 300 MHz,): 3.89 (s, 3H), 4.02 (s, 3H), 6.53 (d, 1H, J=7.8 Hz), 6.74 (d, 1H, J=7.8 Hz), 6.90-6.82 (m, 2H), 7.26 (m, 1H), 7.48-7.39 (m, 4H), 7.53 (s, 1H), 7.79 (s, 1H), 8.15 (s, 1H). $^{13}$C NMR (CDCl$_3$, 100 MHz,): 33.4, 55.7, 106.6, 113.9, 123.2, 126.4, 128.2, 130.1, 133.1, 135.2, 145.1, 146.8. FAB-HRMS calcd for C$_{28}$H$_{18}$N$_2$O$_4$FCl+Na$^+$: 523.08316; found: 523.08243.

3-Benzofuran-3-yl-4-[5-bromo-1-(3-hydroxy-propyl)-1H-indol-3-yl]-pyrrole-2,5-dione (20)

$^1$H NMR (DMSO-d6, 400 MHz) 0.82 (m, 2H), 1.81 (m, 2H), 4.00 (m, 1H), 4.28 (m, 2H), 6.76 (d, J=7.7 Hz, 1H), 6.90 (t, J=7.7 Hz, 1H), 7.13 (s, 1H), 7.19-7.34 (m, 4H), 7.50 (d, J=8.7 Hz, 1H), 7.56 (d, J=8.0 Hz, 1H), 7.63 (d, J=8.2 Hz, 1H), 7.89 (s, 1H), 8.32 (m, 3H), 10.38 (s, 1H), 11.22 (s, 1H). $^{13}$C NMR (DMSO-d6, 100 MHz) 33.5, 56.2, 104.5, 107.2, 110.9, 111.7, 114.1, 114.2, 123.4, 123.6, 124.6, 125.6, 126.8, 127.5, 131.9, 134.4, 135.5, 145.4, 147.0, 170.4, 170.9.

3-Benzofuran-3-yl-4-[5-bromo-1-(3-hydroxy-propyl)-1H-indol-3-yl]-pyrrole-2,5-dione (21)

$^1$H NMR (DMSO-d6, 400 MHz) 1.18 (m, 2H), 1.81 (m, 2H), 4.03 (q, J=7.0 Hz, 1H), 4.28 (m, 2H), 6.75 (d, J=7.5 Hz, 1H), 6.90 (t, J=7.5 Hz, 1H), 7.19-7.34 (m, 3H), 7.50 (d, J=8.7 Hz, 1H), 7.56 (d, J=8.0 Hz, 1H), 7.63 (d, J=8.0 Hz, 1H), 7.89 (s, 1H), 8.29 (s, 1H), 11.22 (s, 1H). $^{13}$C NMR (CD$_3$CN, 100 MHz) 32.4, 43.2, 57.9, 104.2, 111.2, 111.6, 112.1, 112.9, 121.7, 122.6, 123.7, 124.1, 124.8, 125.2, 127.7, 132.3, 134.0, 135.1, 147.0, 154.8, 171.0, 171.3.

3-(5-Bromo-1-methyl-1H-indol-3-yl)-4-(6-hydroxymethyl-benzofuran-3-yl)-pyrrole-2,5-dione (22)

$^1$H NMR (DMSO-d6, 400 MHz) 3.86 (s, 3H), 4.52 (d, J=5.6 Hz, 2H), 5.26 (t, J=6.0 Hz, 1H), 6.79 (d, J=8.0 Hz, 1H), 6.89 (d, J=8.0 Hz, 1H), 7.1 (d, J=2.0 Hz, 1H), 7.21 (dd, J=1.6, 8.8 Hz, 1H), 7.45 (d, J=8.8 Hz, 1H), 7.55 (s, 1H), 7.96 (s, 1H), 8.26 (s, 1H), 11.20 (s, 1H). $^{13}$C NMR (DMSO-d6, 100 MHz) 33.7, 63.0, 103.9, 109.4, 111.6, 113.0, 113.3, 121.4, 121.8, 123.5, 123.8, 124.3, 125.0, 127.6, 132.4, 135.7, 135.9, 140.6, 147.4, 155.1, 172.2, 172.5.

3-(5-Bromo-1-methyl-1H-indol-3-yl)-4-(6-prop-2-ynyloxy-benzofuran-3-yl)-pyrrole-2,5-dione (23)

$^1$H NMR (CDCl$_3$, 400 MHz) 3.83 (s, 3H), 4.67 (s, 1H), 5.42 (d, J=3.9 Hz, 1H), 6.53-6.69 (m, 3H), 6.81 (t, J=4.5 Hz, 1H), 7.22-7.12 (m, 6H), 7.71 (s, 1H), 8.08 (s, 1H).

3-(6-Allyloxy-benzofuran-3-yl)-4-(5-bromo-1-methyl-1H-indol-3-yl)-pyrrole-2,5-dione (24)

$^1$H NMR (DMSO-d6, 400 MHz) 3.84 (s, 3H), 4.99 (s, 2H), 6.59 (dd, J=1.8, 8.7 Hz, 1H), 6.69 (d, J=8.7 Hz, 1H), 6.92 (d, J=1.8 Hz, 1H), 7.20 (dd, J=1.5, 8.5 Hz, 1H), 7.31-7.34 (m, 2H), 7.44 (d, J=8.5 Hz, 1H), 7.94 (s, 1H), 8.17 (s, 1H), 11.20 (s, 1H). $^{13}$C NMR (DMSO-d6, 100 MHz) 33.6, 69.0, 97.2, 103.8, 111.8, 112.8, 112.9, 113.2, 118.0, 118.9, 122.1, 123.4, 123.8, 124.9, 127.5, 132.2, 133.8, 135.7, 135.9, 146.6, 155.8, 157.0, 172.1, 172.4.

3-(5-Bromo-1-methyl-1H-indol-3-yl)-4-[6-(4-methoxy-benzyloxy)-benzofuran-3-yl]-pyrrole-2,5-dione (25)

$^1$H NMR (DMSO-d6, 400 MHz) 3.75 (s, 3H), 3.84 (s, 3H), 4.99 (s, 2H), 6.61 (dd J=2.0, 8.7 Hz, 1H), 6.70 (d, J=8.7 Hz, 1H), 6.91 (d, J=8.5 Hz, 1H), 7.04 (d, J=1.5 Hz, 1H), 7.04 (dd, J=1.5, 8.6 Hz, 1H), 7.31-7.36 (m, 3H), 7.45 (d, J=8.6 Hz, 1H), 7.94 (1s, 1H), 8.17 (s, 1H). $^{13}$C NMR (DMSO-d6, 100 MHz) 33.6, 55.4, 60.2, 69.8, 97.4, 103.8, 111.6, 112.1, 112.9, 113.0, 113.2, 114.1, 118.9, 122.0, 123.4, 123.8, 124.9, 127.5, 129.0, 129.6, 130.0, 130.2, 131.5, 132.2, 135.7, 135.9, 146.6, 155.8, 157.2, 159.4, 172.1, 172.4.

3-(5,7-Dibromo-1-methyl-1H-indol-3-yl)-4-(7-methoxy-benzofuran-3-yl)-pyrrole-2,5-dione (26)

$^1$H NMR (CDCl$_3$, 400 MHz) 4.00 (s, 3H), 4.17 (s, 3H), 6.30 (d, J=7.8 Hz, 1H), 6.73 (d, J=7.8 Hz, 1H), 6.82 (t, J=7.8 Hz, 1H), 7.12 (d, J=1.7 Hz, 1H), 7.37 (d, J=1.7 Hz, 1H), 7.55 (s, 1H), 7.61 (s, 1H), 8.93 (s, 1H). $^{13}$C NMR (CDCl$_3$, 100 MHz) 37.8, 56.2, 104.2, 104.5, 107.2, 111.5, 113.6, 113.9, 123.7, 123.8, 125.0, 126.5, 129.8, 130.0, 130.7, 132.2, 136.8, 144.5, 145.5, 147.3, 170.0, 170.5.

3-(5-Chloro-1-methyl-1H-indol-3-yl)-4-(5-fluoro-benzofuran-3-yl)-pyrrole-2,5-dione (27)

The general procedure of Method A was followed using 5-fluoro-benzofuran-3-one for synthesis of 2-(5-fluoro-benzofuran-3-yl)-acetamide. $^1$H NMR (DMSO-d6, 400 MHz) 3.89 (s, 3H), 6.61 (dd, J=2.5, 9.0 Hz, 1H), 6.80 (d, J=1.6 Hz, 1H), 7.11 (m, 2H), 7.53 (d, J=8.7 Hz, 1H), 7.68 (dd, J=4.2, 9.0 Hz, 1H), 8.03 (s, 1H), 8.35 (s, 1H), 11.24 (s, 1H); $^{13}$C NMR (DMSO-d6, 75 MHz) 33.6, 103.7, 107.3, 107.6, 112.1, 112.6, 113.0, 113.1, 113.2, 120.5, 122.4, 122.6, 125.3, 126.8, 126.9, 132.7, 135.7, 136.1, 149.3, 151.0. FAB-HRMS calcd for C$_{21}$H$_{12}$ClFN$_4$O$_4$+Na$^+$: 417.0413; found: 417.0411.

3-Benzofuran-3-yl-4-(5-iodo-1-methyl-1H-indol-3-yl)-pyrrole-2,5-dione (28)

$^1$H NMR (DMSO-d6, 400 MHz) 3.87 (s, 3H), 6.88 (d, J=7.8 Hz, 1H), 6.94 (t, J=7.8 Hz, 1H), 7.14 (s, 1H), 7.25 (t, J=8.0 Hz, 1H), 7.63 (d, J=8.2 Hz, 1H), 7.95 (s, 1H), 8.26 (s, 1H), 11.20 (s, 1H). $^{13}$C NMR (DMSO-d6, 100 MHz) 33.5, 103.5, 111.8, 113.2, 121.8, 122.9, 123.2, 125.3, 125.8, 128.1, 129.6, 130.2, 130.3, 132.7, 135.0, 136.2, 147.3, 154.7, 172.1, 172.4.

3-(5-Fluoro-benzofuran-3-yl)-4-(5-iodo-1-methyl-1H-indol-3-yl)-pyrrole-2,5-dione (29)

$^1$H NMR (DMSO-d6, 400 MHz) 3.87 (s, 3H), 6.65 (dd, J=2.5, 9.0 Hz, 1H), 7.12 (m, 1H), 7.39 (m, 2H), 7.68 (dd, J=4.0, 9.0 Hz, 1H), 7.98 (s, 1H), 8.31 (s, 1H), 11.18 (s, 1H). HPLC purity: 99%. $^{13}$C NMR (DMSO-d6, 100 MHz) 22.4, 84.7, 103.3, 107.2, 112.2, 112.3, 112.9, 112.0, 112.3, 122.4, 127.1, 127.9, 130.1, 130.4, 132.9, 135.5, 136.2, 149.2, 151.1, 172.0, 172.3.

3-Benzofuran-3-yl-4-(5-benzyloxy-1-methyl-1H-indol-3-yl)-pyrrole-2,5-dione (31)

(See Scheme 4). $^1$H NMR (DMSO-d6, 400 MHz) 3.88 (s, 3H), 4.15 (s, 2H), 5.76 (s, 1H), 6.22 (d, J=2.3 hz, 1H), 6.75

(dd, J=2.3, 8.7 Hz, 1H), 7.04 (t, J=7.6 Hz, 1H), 7.14 (m, 3H), 7.28-1.38 (m, 5H), 7.65 (d, J=8.3 Hz, 1H), 8.05 (s, 1H), 8.18 (s, 1H), 11.16 (s, 1H); $^{13}$C NMR (DMSO-d6, 100 MHz) 33.6, 69.2, 104.0, 104.5, 111.8, 112.4, 113.2, 120.8, 122.2, 123.4, 125.3, 126.1, 126.6, 127.6, 128.1, 128.7, 132.4, 133.6, 135.4, 137.2, 147.1, 153.3, 154.6, 172.4, 172.7. FAB-HRMS calcd for $C_{28}H_{20}N_2O_4+Na^+$: 471.1315; found: 471.1311.

3-Benzofuran-3-yl-4-(5-hydroxy-1-methyl-1H-indol-3-yl)-pyrrole-2,5-dione (30) (See Scheme 4)

To a solution of 3-benzofuran-3-yl-4-(5-benzyloxy-1-methyl-1H-indol-3-yl)-pyrrole-2,5-dione (31) (22 mg, 0.044 mmol) in 2 ml of dry dichloromethane was added dropwise boron tribromide (44 mg, 0.178 mmol) at −10° C. After 45 min, the reaction was quenched with saturated NaHCO$_3$, and diluted with ethyl acetate. The organic layer was separated, dried over anhydrous Na$_2$SO$_4$ and concentrated. The residue was purified by preparative TLC (ethyl acetate:hexane; 2:3) to afford product (11 mg, 68%). $^1$H NMR (DMSO-d6, 400 MHz) 3.81 (s, 3H), 6.21 (d, J=2.1 Hz, 1H), 6.59 (dd, J=2.2, 8.5 Hz, 1H), 6.96 (m, 2H), 7.18 (m, 2H), 7.60 (d, J=8.5 Hz, 1H), 7.86 (s, 1H), 8.23 (s, 1H), 8.67 (s, 1H), 11.12 (s, 1H); $^{13}$C NMR (DMSO-d6, 100 MHz) 14.5, 103.6, 106.1, 111.2, 111.8, 111.9, 112.5, 121.1, 122.2, 123.0, 125.0, 126.1, 127.0, 131.6, 133.2, 134.9, 147.3, 152.1, 154.6, 172.4, 172.7. FAB-HRMS calcd for $C_{21}H_{14}N_2O_4+Na^+$: 381.0846; found: 381.0844.

3-Benzofuran-3-yl-4-[5-benzyloxy-1-(3-hydroxypropyl)-1H-indol-3-yl]-pyrrole-2,5-dione (32)

$^1$H NMR (DMSO-d6, 400 MHz) 1.89 (m, 2H), 3.39 (m, 2H), 4.21 (s, 2H), 4.31 (m, 2H), 4/65 (t, J=5.0 Hz, 1H, OH), 6.29 (d, J=2.2 Hz, 1H), 6.74 (dd, J=2.2, 9.0 Hz, 1H), 7.00 (t, J=7.6 Hz, 1H), 7.06 (d, J=7.6 Hz, 1H), 7.14 (d, J=7.0 hz, 1H), 7.22-7.30 (m, 4H), 7.41 (d, J=8.9 Hz, 1H), 7.64 (d, J=8.3 Hz, 1H), 8.00 (s, 1H), 8.22 (s, 1H), 11.17 (s, 1H); $^{13}$C NMR (DMSO-d6, 100 MHz) 33.2, 43.5, 57.9, 69.3, 104.2, 104.6, 111.7, 111.8, 112.3, 113.2, 121.2, 122.1, 123.3, 125.3, 126.3, 126.4, 127.7, 128.1, 128.7, 131.6, 133.5, 134.4, 137.3, 147.2, 153.3, 154.6172.3, 172.6. FAB-HRMS calcd for $C_{30}H_{24}N_4O_5+Na^+$: 515.1577; found: 515.1574.

3-(4-Benzofuran-3-yl-2,5-dioxo-2,5-dihydro-1H-pyrrol-3-yl)-1-methyl-1H-indole-5-carbonitrile (33)

The general procedure of Method A was followed. $^1$H NMR (DMSO-d6, 400 MHz) 3.90 (s, 3H), 6.74 (d, J=7.6 Hz, 1H), 6.89 (t, J=7.6 Hz, 1H), 7.22 (dt, J=0.8, 7.6 Hz, 1H), 7.31 (d, J=0.8 Hz, 1H), 7.44 (dd, J=1.2, 8.8 Hz, 1H), 7.63 (d, J=8.4 Hz, 1H), 7.67 (d, J=8.4 Hz, 1H), 8.06 (s, 1H), 8.36 (s, 1H), 11.28 (s, 1H). $^{13}$C NMR (DMSO-d6, 100 MHz) 33.3, 102.1, 104.7, 111.0, 111.6, 112.0, 119.9, 121.5, 122.9, 124.3, 124.7, 125.0, 125.1, 125.4, 126.2, 131.4, 136.2, 138.3, 147.5, 154.3, 171.6, 171.9.

3-[4-(6-Hydroxymethyl-benzofuran-3-yl)-2,5-dioxo-2,5-dihydro-1H-pyrrol-3-yl]-1-methyl-1H-indole-5-carbonitrile (34)

The procedure used to synthesize (7) was followed. $^1$H NMR (DMSO-d6, 400 MHz) 3.91 (s, 3H), 4.51 (d, J=5.7 Hz, 2H), 5.25 (t, J=5.8 Hz, 1H), 6.68 (d, J=8.1 Hz, 1H), 6.85 (d, J=8.2 Hz, 1H), 7.40 (s, 1H), 7.47 (dd, J=1.2, 8.5 Hz, 1H), 7.55 (s, 1H), 7.68 (d, J=8.6 Hz, 1H), 8.05 (s, 1H), 8.33 (s, 1H), 11.27 (s, 1H). $^{13}$C NMR (DMSO-d6, 100 MHz) 30.1, 62.8, 102.0, 111.5, 113.3, 115.9, 116.6, 117.0, 119.9, 120.1, 122.9, 123.2, 127.7, 129.4, 130.5, 130.8, 135.4, 144.2, 144.4, 145.0, 154.9, 169.0, 169.9.

1-Cyclopropylmethyl-3-[4-(5,6-difluoro-benzofuran-3-yl)-2,5-dioxo-2,5-dihydro-1H-pyrrol-3-yl]-1H-indole-5-carbonitrile. (35)

1-Cyclopropylmethyl-1H-indole-5-carbonitrile. To a solution of 5-cyano-indole (0.15 mg, 1.05 mmol) in dry DMF (3.5 mL) sodium hydride (55% in oil) (69 mg, 1.58 mmol) was added in one portion at 0° C. The mixture was stirred at 0° C. for 30 min and (bromomethyl)-cyclopropane (0.133 mL, 1.37 mmol) was added. The resulting mixture was allowed to warm to room temperature, and stirred for 30 min. After completion monitored by TLC, reaction mixture was quenched with ice and extracted with EtOAc. The organic layer was washed with water, dried over MgSO$_4$, filtered, and concentrated. The residue was purified by column chromatography (EtOAc:hexane, 1:9) to give the product as a colorless solid (180 mg, 87%). $^1$H NMR (CDCl$_3$, 400 MHz,): 0.40 (m, 1H), 0.68 (m, 1H), 0.89 (m, 1H), 4.02 (d, J=6.7 Hz, 2H), 6.60 (d, J=3.2 Hz, 7.98 (s, 1H), 7.36 (d, J=3.2 Hz, 2H), 1H), 7.42 (d, J=3.4 Hz, 2H). $^{13}$C NMR (CDCl$_3$, 100 MHz,): 4.14, 11.1, 50.9, 102.2, 110.2, 120.9, 124.3, 126.5, 128.2, 129.8, 137.6.

(5-Cyano-1-cyclopropylmethyl-1H-indol-3-yl)-oxo-acetic acid methyl ester. $^1$H NMR (CDCl$_3$, 400 MHz,): 0.48 (m, 1H), 0.80 (m, 2H), 1.36 (m, 1H), 3.98 (s, 3H), 4.08 (d, J=7.0 Hz, 1H), 7.49 (d, J=8.5 Hz, 1H), 7.57 (d, J=8.5 Hz, 1H), 8.67 (s, 1H), 8.77 (s, 1H). $^{13}$C NMR (CDCl$_3$, 100 MHz,): 4.50, 10.6, 52.0, 52.9, 106.8, 110.4, 111.1, 113.1, 119.7, 127.0, 127.1, 128.0, 138.3, 140.6, 162.6, 176.7.

1-Cyclopropylmethyl-3-[4-(5,6-difluoro-benzofuran-3-yl)-2,5-dioxo-2,5-dihydro-1H-pyrrol-3-yl]-1H-indole-5-carbonitrile. $^1$H NMR (DMSO-d6, 400 MHz): 0.29 (m, 2H), 0.43 (m, 2H), 1.19 (m, 1H), 4.18 (d, J=7.1 Hz, 1H), 6.59 (m, 1H), 7.51 (d, J=8.6 Hz, 1H), 7.82 (d, J=8.6 Hz, 1H), 7.96 (m, 1H), 8.01 (s, 1H), 8.48 (s, 1H), 11.3 (s, 1H). $^{13}$C NMR (DMSO-d6, 100 MHz,): 3.88, 11.7, 50.6, 102.7, 105.1, 112.7, 124.4, 125.2, 125.7, 127.0, 132.5, 135.6, 138.1, 150.0, 171.7, 172.1. FAB-HRMS calcd for $C_{25}H_{15}N_3O_3F_2+Na^+$: 466.09740; found: 466.09720.

3-Benzofuran-3-yl-4-(5-ethynyl-1-methyl-1H-indol-3-yl)-pyrrole-2,5-dione 36) (Scheme 7)

1-Methyl-5-trimethylsilanylethynyl-1H-indole. To a solution of 5-iodo-1-methyl-1H-indole (200 mg, 0.778 mmol) in pyrrolidine (5 mL) was added ethynyl-trimethyl-silane (92 mg, 0.932 mmol), followed by tetrakis-triphenyl-phosphine palladium (61 mg, 0.233 mmol) after which the reaction mixture was heated at 50° C. for 12 h. The reaction mixture was filtered and the filtrate evaporated in vacuo to obtain a residue, which was purified by column chromatography (ethyl acetate:hexane; 5:95) to give a product (150 g, 84%). $^1$H NMR (CDCl$_3$, 400 MHz) 0.25 (s, 9H), 3.76 (s, 3H), 6.44 (d, J=3.0 Hz, 1H), 7.04 (d, J=3.0 Hz, 1H), 7.23 (d, J=8.4 Hz, 1H), 7.30 (dd, J=1.4 Hz, 1H), 7.78 (d, J=1.4 Hz, 1H); $^{13}$C NMR (CDCl$_3$, 100 MHz) 0.18, 32.8, 90.9, 101.2, 107.0, 109.0, 113.6, 125.3, 125.4, 128.1, 129.6, 136.4.

(5-Ethynyl-1-methyl-1H-indol-3-yl)-oxo-acetic acid ethyl ester. To a solution of 1-methyl-5-trimethylsilanylethynyl-1H-indole (115 mg, 0.505 mmol) in Et$_2$O (5 mL) cooled to 0° C. a 2.0 M solution of oxalyl chloride in THF (0.40 mL, 0.80 mmol) was added dropwise. The reaction was then stirred for 0.5 h at 0° C. and allowed to warm to room temperature and stirred overnight. It was then cooled to −60° C. and a 21% solution of NaOEt in EtOH (0.75 mL, 2.02 mmol) was added, after which the reaction mixture was allowed to warm to room temperature. The reaction was quenched by the addition of water and diluted with ethyl acetate. The organic layer was separated, dried over anhydrous $Na_2SO_4$ and concentrated. The residue was purified by column chromatography (ethyl acetate:hexane; 1:5) to give a product (105 mg, 81%). $^1$H NMR ($CDCl_3$, 400 MHz) 1.43 (t, J=7.0 Hz, 3H), 3.07 (s, 1H), 3.83 (s, 3H), 4.42 (q, J=7.0 Hz, 2H), 7.06 (d, J=8.3 Hz, 1H), 7.46 (dd, J=1.4, 8.3 Hz, 1H), 8.35 (s, 1H), 8.60 (s, 1H); $^{13}$C NMR ($CDCl_3$, 100 MHz) 14.0, 33.8, 62.1, 76.2, 84.2, 109.9, 117.1, 126.8, 127.0, 128.0, 137.0, 140.9, 162.7, 177.2.

To a suspension of 2-benzofuran-3-yl-acetamide (Y=H, 28 mg, 0.164 mmol) and (5-ethynyl-1-methyl-1H-indol-3-yl)-oxo-acetic acid ethyl ester (35 mg, 0.137 mmol) in dry THF (2.5 mL) at 0° C. was added dropwise a 1.0 M solution of tert-BuOK in THF (0.54 mL), and the reaction mixture was allowed to stir at room temperature overnight. The reaction mixture was quenched with 12 N HCl and diluted with EtOAc. The organic solution was washed with saturated $NaHCO_3$, brine, then dried over $Na_2SO_4$, evaporated in vacuo and purified by preparative TLC (ethyl acetate:hexane; 2:3) to afford product (23 mg, 45%) as an orange solid. $^1$H NMR ($CDCl_3$, 400 MHz) 3.84 (s, 3H), 6.80 (d, J=7.5 Hz, 1H), 6.85 (t, J=7.5 Hz, 1H), 7.18-7.49 (m, 4H), 7.50 (m, 2H), 7.74 (s, 1H), 8.16 (s, 1H); $^{13}$C NMR ($CDCl_3$, 100 MHz) 33.5, 105.2, 109.6, 111.4, 111.5, 114.3, 121.9, 122.6, 124.9, 125.0, 126.3, 126.5, 134.4, 136.7, 147.2, 155.0, 170.4, 170.9. FAB-HRMS calcd for $C_{23}H_{14}N_2O_3+Na^+$: 389.0896; found: 389.0895.

3-Benzofuran-3-yl-4-(5-cyclopropyl-1-methyl-1H-indol-3-yl)-pyrrole-2,5-dione (37). (See Scheme 8)

1-Methyl-5-vinyl-1H-indole. To a solution of 1-methyl-5-trimethylsilanylethynyl-1H-indole (0.50 g, 1.95 mmol) in DMF (10 mL) were added lithium chloride (0.32 mg, 7.59 mmol), bis(triphenylphosphine)palladium (II) (0.225 g, 0.195 mmol) and tributylvinyltin (0.80 g, 2.52 mmol). The resulting suspension was heated at 80° C. for 2 h and cooled to room temperature. The reaction mixture was filtered through Celite pad washing with ethyl acetate, organic solvents were evaporated in vacuo. The residue was purified by column chromatography (ethyl acetate:hexane; 5:95) to give a product (290 mg, 94%). $^1$H NMR (DMSO-d6, 400 MHz) 3.77 (s, 1H), 5.10 (d, J=3.9 Hz, 1H), 5.70 (d, J=7.6 Hz, 1H), 6.40 (d, J=2.5 Hz, 1H), 6.80 (dd, J=11.0, 17.3 Hz, 1H), 7.30-7.41 (m, 3H), 7.58 (s, 1H); $^{13}$C NMR (DMSO-d6, 100 MHz) 32.9, 101.1, 110.2, 111.0, 119.2, 119.5, 128.5, 128.8, 130.6, 136.7, 138.3.

5-Cyclopropyl-1-methyl-1H-indole. To a solution of 1-Methyl-5-vinyl-1H-indole (290 mg, 1.84 mmol) in dioxane (5 mL) was cooled at 0° C. and solution of $CH_2N_2$ in diethyl ether was added. The reaction mixture was allowed to warm to room temperature and stirred for 12 h. The solvents were evaporated and the residue was purified by column chromatography (ethyl acetate:hexane; 5:95) to give a product (305 mg, 96%). $^1$H NMR ($CDCl_3$, 400 MHz) 0.68 (m, 2H), 0.88 (m, 2H), 2.00 (m, 1H), 3.71 (s, 1H), 6.37 (d, J=2.9 Hz, 1H), 6.97 (m, 2H), 7.18 (d, J=8.4 Hz, 1H), 7.34 (s, 1H); $^{13}$C NMR ($CDCl_3$, 100 MHz) 8.5, 13.6, 17.5, 32.8, 100.3, 108.9, 117.5, 120.4, 128.6, 128.9, 134.4, 135.3.

(5-Cyclopropyl-1-methyl-1H-indol-3-yl)-oxo-acetic acid ethyl ester. To a solution of 5-cyclopropyl-1-methyl-1H-indole (290 mg, 1.69 mmol) in $Et_2O$ (5 mL) cooled to 0° C. a 2.0 M solution of oxalyl chloride in THF (0.14 mL, 2.71 mmol) was added dropwise. The reaction was then stirred for 0.5 h at 0° C. and allowed to warm to room temperature and stirred overnight. It was then cooled to −60° C. and a 21% solution of NaOEt in EtOH (2.6 mL, 6.77 mmol) was added, after which the reaction mixture was allowed to warm to room temperature. The reaction was quenched by the addition of water and diluted with ethyl acetate. The organic layer was separated, dried over anhydrous $Na_2SO_4$ and concentrated. The residue was purified by column chromatography (ethyl acetate:hexane; 1:5) to give a product (200 mg, 43%). $^1$H NMR ($CDCl_3$, 400 MHz) 0.78 (m, 2H), 1.00 (m, 2H), 1.45 (t, J=7.1 Hz, 1H), 2.07 (m, 1H), 3.86 (s, 1H), 4.43 (q, J=7.1 Hz, 2H), 7.13 (d, J=8.2 Hz, 1H), 7.27 (d, J=8.2 Hz, 1H), 8.18 (s, 1H), 8.29 (s, 1H).

To a suspension of 2-benzofuran-3-yl-acetamide (Y=H, 32 mg, 0.184 mmol) and (5-cyclopropyl-1-methyl-1H-indol-3-yl)-oxo-acetic acid ethyl ester (50 mg, 0.184 mmol) in dry THF (2.5 mL) at 0° C. was added dropwise a 1.0 M solution of tert-BuOK in THF (0.73 mL), and the reaction mixture was allowed to stir at room temperature overnight. The reaction mixture was quenched with 12 N HCl and diluted with EtOAc. The organic solution was washed with saturated $NaHCO_3$, brine, then dried over $Na_2SO_4$, evaporated in vacuo and purified by preparative TLC (ethyl acetate:hexane; 2:3) to afford product (25 mg, 35%) as an orange solid. $^1$H NMR (DMSO-d6, 400 MHz) −0.21 (m, 2H), 0.54 (m, 2H), 1.55 (m, 1H), 3.85 (s, 3H), 6.22 (s, 1H), 6.91-7.00 (m, 3H), 7.22 (t, J=7.0 Hz, 1H), 7.29 (d, J=8.4 Hz, 1H), 7.60 (d, J=8.4 Hz, 1H), 8.01 (s, 1H), 8.17 (s, 1H), 11.13 (s, 1H); $^{13}$C NMR (DMSO-d6, 100 MHz) 8.8, 15.0, 33.5, 103.9, 110.3, 111.7, 112.3, 116.2, 122.0, 122.7, 123.2, 125.2, 126.0, 126.4, 133.4, 135.1, 135.7, 146.9, 154.6, 172.4, 172.7. FAB-HRMS calcd for $C_{24}H_{18}N_2O_3+Na^+$: 405.1209; found: 405.1214.

3-(5-Cyclopropylethynyl-1-methyl-1H-indol-3-yl)-4-(5-fluoro-benzofuran-3-yl)-pyrrole-2,5-dione (38). 5-Cyclopropylethynyl-1-methyl-1H-indole A mixture of the 5-iodo-1-methyl-indole (0.40 g, 1.56 mmol), $PdCl_2(PPh_3)_2$ (0.109 g, 0.156 mmol), CuI (0.059 g, 0.311 mmol), and $PPh_3$ (0.082 g, 0.311 mmol) in diisopropylamine (6.0 mL) was degassed for 1 min and stirred for 10 min at room temperature. Cyclopropylacetylene (0.16 mL, 3.11 mmol) was added. The mixture was degassed for 1 min, and stirred at 85° C. overnight. The resulting mixture was cooled to ambient temperature and poured into a mixture of 0.1 N HCl/EtOAc (15 mL/15 mL). After partition, the organic layer was washed with water, filtered, and concentrated. The residue was purified by preparative TLC (ethyl acetate-hexane, 1:19) to afford the product (0.27 g, 89%). $^1$H NMR ($CDCl_3$, 400 MHz,): 7.67 (s, 1H), 7.23 (d, J=8.5 Hz, 1H), 7.17 (d, J=8.5 Hz, 1H), 6.99 (d, J=3.0 Hz, 1H), 6.40 (d, J=2.6 Hz, 1H), 3.71 (s, 3H), 1.46 (m, 1H), 0.86-0.79 (m, 4H). $^{13}$C NMR ($CDCl_3$, 100 MHz,): 0.28, 8.5, 32.8, 77.1, 90.5, 101.0, 109.0, 114.4, 124.6, 125.3, 128.3, 129.5, 136.0.

(5-Cyclopropylethynyl-1-methyl-1H-indol-3-yl)-oxo-acetic acid ethyl ester. $^1$H NMR ($CDCl_3$, 400 MHz,): 0.92-0.84 (m, 4H), 1.53-1.43 (m, 4H), 3.85 (s, 3H), 4.41 (q, J=7.1 Hz, 1H), 7.25 (d, J=8.5 Hz, 1H), 7.37 (d, J=8.5 Hz, 1H), 8.47 (s, 1H), 8.30 (s, 1H). $^{13}$C NMR ($CDCl_3$, 100 MHz,): 0.22, 8.55, 14.1, 33.8, 62.1, 76.3, 92.5, 109.7, 112.7, 119.1, 126.2, 126.9, 127.7, 136.4, 140.7, 162.9, 177.2.

3-(5-Cyclopropylethynyl-1-methyl-1H-indol-3-yl)-4-(5-fluoro-benzofuran-3-yl)-pyrrole-2,5-dione. $^1$H NMR ($CDCl_3$, 400 MHz,): 0.67 (m, 2H), 0.82 (m, 2H), 1.34 (m, 1H), 3.87 (s, 3H), 6.59 (d, J=8.7 Hz, 1H), 6.97-6.93 (m, 2H), 7.17 (d, J=8.3 Hz, 1H), 7.22 (d, J=8.4 Hz, 1H), 7.46-7.43 (m, 1H), 7.53 (br. s, 1H), 7.81 (s, 1H), 8.10 (s, 1H). $^{13}$C NMR (CDCl₃, 100 MHz,): 0.05, 8.48, 33.6, 75.9, 91.5, 104.6, 107.6, 111.9, 112.1, 112.8, 116.4, 122.6, 125.5, 125.6, 126.4, 126.5, 132.4, 134.5, 136.2, 148.7, 151.2, 158.8, 170.7, 171.1. FAB-HRMS calcd for $C_{26}H_{16}N_2O_3F$: 423.11504; found: 423.11473.

3-Benzofuran-3-yl-4-(1-methyl-5-morpholin-4-yl-1H-indol-3-yl)-pyrrole-2,5-dione (39)

$^1$H NMR (CDCl₃, 400 MHz) 2.42 (m, 4H), 3/62 (m, 4H), 3.86 (s, 3H), 6.21 (s, 1H), 6.82 (d, J=7.8 Hz, 1H), 6.98 (t, J=7.8 Hz, 1H), 7.16-7.23 (m, 2H), 7.40 (s, 1H), 7.48 (d, J=8.5 Hz, 1H), 7.92 (d, J=3.4 Hz, 1H). $^{13}$C NMR (CDCl₃, 100 MHz) 33.6, 50.6, 66.8, 104.5, 108.7, 110.2, 111.3, 112.3, 115.1, 120.9, 122.2, 123.0, 124.8, 126.2, 132.4, 133.3, 134.4, 146.4, 146.5, 154.8, 170.7, 171.2.

3-(5-Fluoro-benzofuran-3-yl)-4-(5-methyl-5H-[1,3]dioxolo[4,5-f]indol-7-yl)-pyrrole-2,5-dione (40)

$^1$H NMR (CDCl₃, 400 MHz) 3.79 (s, 3H), 5.80 (m, 2H), 6.29 (s, 1H), 6.59 (dd J=2.4, 9.0 Hz, 1H), 6.74 (s, 1H), 6.91 (td, J=2.5, 9.0 Hz, 1H), 7.41 (dd, J=4.1, 8.0 Hz, 1H), 7.65 (s, 1H), 7.95 (s, 1H), 8.13 (s, 1H). $^{13}$C NMR (CDCl₃, 100 MHz) 33.8, 60.4, 90.7, 100.1, 100.8, 105.0, 107.7, 107.9, 112.0, 112.1, 112.5, 112.8, 120.0, 121.8, 126.3, 126.5, 132.2, 132.3, 132.6, 143.7, 145.4, 148.6, 151.0, 157.5, 159.9, 170.8, 171.3.

3-Benzofuran-3-yl-4-(5-methoxy-1-methyl-1H-indol-3-yl)-pyrrole-2,5-dione (41)

$^1$H NMR (DMSO-d6, 400 MHz) 3.00 (s, 3H), 3.87 (s, 3H), 6.14 (d, J=2.3 Hz, 1H), 6.66 (dd, J=2.3, 8.8 Hz, 1H), 6.99 (t, J=7.3 Hz, 1H), 7.09 (d, J=7.6 Hz, 1H), 7.26 (dt, J=1.1, 7.3 Hz, 1H), 7.40 (d, J=8.5 Hz, 1H), 7.62 (d, J=8.5 Hz, 1H), 7.98 (s, 1H), 8.20 (s, 1H), 11.15 (s, 1H); $^{13}$C NMR (DMSO-d6, 100 MHz) 33.6, 54.4, 102.8, 104.0, 111.7, 112.4, 112.8, 120.8, 122.0, 123.3, 125.3, 126.2, 126.6, 132.1, 133.6, 135.1, 147.0, 154.2, 154.5, 172.4, 172.7. FAB-HRMS calcd for $C_{22}H_{16}N_2O_4$+Na⁺: 395.1002; found: 395.0996.

3-Benzofuran-3-yl-4-(6-chloro-5-methoxy-1-methyl-1H-indol-3-yl)-pyrrole-2,5-dione (42)

$^1$H NMR (DMSO-d6, 400 MHz) 3.11 (s, 3H), 3.83 (s, 3H), 6.30 (s, 1H), 6.93 (t, J=4.7 Hz, 1H), 7.04 (d, J=4.7 Hz, 1H), 7.22 (t, J=5.2 Hz, 1H), 7.30 (d, J=1.7 Hz, 1H), 7.47 (d, J=5.2 Hz, 1H), 7.86 (s, 1H), 8.01 (s, 1H). $^{13}$C NMR (DMSO-d6, 100 MHz) 33.6, 55.3, 104.0, 104.6, 111.1, 111.3, 112.0, 118.9, 121.9, 123.0, 124.8, 125.0, 125.8, 131.5, 132.5, 134.4, 146.5, 149.7, 154.7, 171.7, 172.1.

3-Benzofuran-3-yl-4-(6-iodo-5-methoxy-1-methyl-1H-indol-3-yl)-pyrrole-2,5-dione (43)

Reaction of 2-fluoro-1-iodo-4-methyl-5-nitro-benzene with N,N-dimethylformamide dimethyl acetal. (See Scheme 5) A mixture of N,N-dimethylformamide dimethyl acetal (1.70 mL, 12.74 mmol) and 2-fluoro-1-iodo-4-methyl-5-nitro-benzene (2.78 g, 9.80 mmol) in dry DMF (10.0 mL) was stirred at 125° C. for 3 h. The resulting mixture was partitioned between EtOAc and water. The organic layer was washed with brine, dried over MgSO₄, filtered, and concentrated. The residue was washed with hexane to give a mixture of two products: [2-(5-fluoro-4-iodo-2-nitro-phenyl)-vinyl]- and [2-(4-iodo-5-methoxy-2-nitro-phenyl)-vinyl]-dimethyl-amines (1.16 g), which were directly used in next step.

The mixture of enamines (1.16 g, 3.50 mmol) was dissolved in EtOH (30.0 mL) To this solution Fe (2.33 g, 41.6 mmol) and acetic acid (30.0 mL) were added and the mixture was stirred at 90° C. for 2 h. The resulting mixture was filtered through Celite and concentrated. The residue was purified by column chromatography (ethyl acetate-hexane; 5:95) to afford 5-fluoro-6-iodo-1H-indole (0.23 g, 24%) and 6-iodo-5-methoxy-1-methyl-1H-indole (0.16 g, 16%).

5-fluoro-6-iodo-1H-indole. $^1$H NMR (CDCl₃, 400 MHz): 6.52 (m, 1H), 7.22 (m, 1H), 7.36 (d, J=8.4 Hz, 1H), 7.70 (d, J=5.1 Hz, 1H), 8.20 (br. s, 1H).

6-Iodo-5-methoxy-1H-indole. $^1$H NMR (CDCl₃, 400 MHz): 3.91 (s, 3H), 6.48 (s, 1H), 7.11-7.14 (m, 2H), 7.77 (s, 1H), 8.21 (br. s, 1H).

3-Benzofuran-3-yl-4-(6-iodo-5-methoxy-1-methyl-1H-indol-3-yl)-pyrrole-2,5-dione $^1$H NMR (CDCl₃, 400 MHz) 3.09 (s, 3H), 3.83 (s, 3H), 6.29 (s, 1H), 6.96 (t, J=4.7 Hz, 1H), 7.08 (d, J=4.7 Hz, 1H), 7.21 (m, 2H), 7.47 (m, 2H), 7.69 (s, 1H), 7.86 (s, 1H), 8.00 (s, 1H). $^{13}$C NMR (DMSO-d6, 75 MHz) 33.7, 55.4, 81.0, 102.4, 103.9, 111.8, 112.2, 121.1, 121.5, 121.9, 123.4, 125.4, 126.4, 133.2, 133.4, 135.6, 147.2, 151.9, 154.5, 172.2, 172.5.

3-Benzofuran-3-yl-4-(5-benzyloxy-1H-indol-3-yl)-pyrrole-2,5-dione (44)

$^1$H NMR (DMSO-d6, 400 MHz) 4.18 (s, 2H), 6.26 (d, J=2.2 Hz, 1H), 6.68 (dd, J=2.3, 8.8 Hz, 1H), 7.04 (t, J=7.5 Hz, 1H), 7.14 (d, J=6.8 Hz, 1H), 7.29 (m, 5H), 7.64 (d, J=8.3 Hz, 1H), 7.98 (d, J=2.2 Hz, 1H), 8.19 (s, 1H), 11.16 (s, 1H), 11.85 (s, 1H); $^{13}$C NMR (DMSO-d6, 100 MHz) 69.3, 104.2, 105.1, 111.7, 112.3, 113.2, 122.1, 123.3, 125.3, 125.7, 126.5, 127.7, 128.1, 128.7, 131.6, 134.0, 137.3, 147.2, 153.1, 154.6, 172.4, 172.7. FAB-HRMS calcd for $C_{27}H_{18}N_2O_4$+Na⁺: 457.1159; found: 457.1156.

3-Benzofuran-3-yl-4-(6-hydroxy-1-methyl-1H-indol-3-yl)-pyrrole-2,5-dione (45)

The same procedure was followed using 3-benzofuran-3-yl-4-(6-benzyloxy-1-methyl-1H-indol-3-yl)-pyrrole-2,5-dione (47). $^1$H NMR (DMSO-d6, 400 MHz) 3.76 (s, 3H), 6.19 (dd, J=2.0, 8.6 Hz, 1H), 6.53 (d, J=8.6 Hz, 1H), 6.72 (s, J=2.0 Hz, 1H), 6.95 (d, J=4.0 Hz, 1H), 7.23 (m, 1H), 7.60 (d, J=8.6 Hz, 1H), 7.82 (s, 1H), 8.21 (s, 1H), 9.16 (s, 1H), 11.09 (s, 1H); $^{13}$C NMR (DMSO-d6, 100 MHz) 33.3, 96.0, 104.5, 110.8, 111.7, 112.0, 118.8, 121.2, 121.8, 122.2, 123.1, 125.1, 126.1, 133.2, 133.6, 138.4, 147.1, 154.1, 154.5, 172.3, 172.6. FAB-HRMS calcd for $C_{21}H_{14}N_2O_4$+Na⁺: 381.0846; found: 381.0841.

3-(5-Fluoro-benzofuran-3-yl)-4-(6-hydroxy-1-methyl-1H-indol-3-yl)-pyrrole-2,5-dione (46)

The general procedure of Method A was followed using 5-fluoro-benzofuran-3-one for synthesis of 2-(5-fluoro-benzofuran-3-yl)-acetamide.

The same procedure was followed as described using 3-(6-benzyloxy-1-methyl-1H-indol-3-yl)-4-(5-fluoro-benzofuran-3-yl)-pyrrole-2,5-dione (1p). $^1$H NMR (DMSO-d6, 400 MHz) 3.78 (s, 3H), 6.23 (dd, J=1.9, 8.6 Hz, 1H), 6.51 (d, J=8.6 Hz, 1H), 6.67 (dd, J=2.5, 9.0 Hz, 1H), 6.76 (d, J=1.9 Hz, 1H), 7.09 (dt, J=2.5 Hz, 1H), 7.65 (dd, J=4.1, 9.0 Hz, 1H), 7.84 (s, 1H), 8.27 (s, 1H), 9.20 (s, 1H), 11.13 (s, 1H); $^{13}$C NMR (DMSO-d6, 100 MHz) 33.3, 96.1, 104.3, 107.6, 107.8, 110.9, 112.3, 112.7, 112.9, 113.0, 118.7, 120.7, 121.7, 127.2, 127.3, 128.3, 128.5, 133.4, 133.7, 138.5, 149.0, 150.9, 154.2, 157.3, 159.6, 172.2, 172.5. FAB-HRMS calcd for $C_{21}H_{13}N_2O_4F_1+Na^+$: 399.0751; found: 399.0749.

3-Benzofuran-3-yl-4-(6-benzyloxy-1-methyl-1H-indol-3-yl)-pyrrole-2,5-dione (47)

$^1$H NMR (DMSO-d6, 400 MHz) 3.83 (s, 3H), 5.05 (s, 2H), 6.43 (dd, J=2.0, 8.9 Hz, 1H), 6.68 (d, J=8.9 Hz, 1H), 6.95 (d, J=4.0 Hz, 1H), 7.13 (d, J=2.0 Hz, 1H), 7.24 (m, 1H), 7.26-7.59 (m, 5H), 7.61 (d, J=8.3 Hz, 1H), 7.87 (s, 1H), 8.23 (s, 1H), 11.15 (s, 1H); $^{13}$C NMR (DMSO-d6, 100 MHz) 33.4, 69.9, 95.5, 104.4, 110.8, 111.8, 111.9, 120.0, 121.8, 121.9, 122.1, 123.2, 125.2, 126.0, 128.2, 128.8, 133.1, 134.0, 138.1, 147.3, 154.5, 155.4, 172.3, 172.6. FAB-HRMS calcd for $C_{28}H_{20}N_2O_4+Na^+$: 471.1315; found: 471.1312.

3-(6-Benzyloxy-1-methyl-1H-indol-3-yl)-4-(5-fluoro-benzofuran-3-yl)-pyrrole-2,5-dione (48)

The general procedure of Method A was followed using 5-fluoro-benzofuran-3-one for synthesis of 2-(5-fluoro-benzofuran-3-yl)-acetamide. $^1$H NMR (DMSO-d6, 400 MHz) 3.84 (s, 3H), 5.06 (s, 2H), 6.54 (dd, J=2.2, 8.8 Hz, 1H), 6.64 (dd, J=2.6, 9.0 Hz, 1H), 6.80 (d, J=8.8 HZ, 1H), 6.85 (d, J=2.6 Hz, 1H), 6.95 (dt, J=2.6, 9.0 Hz, 1H), 7.33-7.43 (m, 8H), 7.47 (s, 1H), 7.79 (s, 1H), 8.10 (s, 1H), 11.15 (s 1H); $^{13}$C NMR (DMSO-d6, 100 MHz) 33.1, 70.1, 94.5, 104.4, 107.4, 107.6, 110.6, 111.6, 111.7, 112.1, 112.4, 119.7, 121.2, 121.9, 127.1, 127.5, 128.1, 132.2, 133.0, 136.5, 137.6, 148.1, 150.6, 155.5, 170.1, 170.6. FAB-HRMS calcd for $C_{28}H_{19}FN_2O_4+Na^+$: 489.1221; found: 429.1221.

3-(7-Methoxy-benzofuran-3-yl)-4-(1-methyl-6-trifluoromethyl-1H-indol-3-yl)-pyrrole-2,5-dione (49)

$^1$H NMR (CDCl$_3$, 400 MHz) 3.94 (s, 3H), 4.02 (s, 3H), 6.43 (d, J=7.8 Hz, 1H), 6.71 (d, J=8.0 Hz, 1H), 6.81 (t, J=8.0 Hz, 1H)<7.12 (m, 2H), 7.62 (s, 1H), 7.70 (s, 1H), 7.88 (s, 1H), 8.14 (s, 1H). $^{13}$C NMR (CDCl$_3$, 100 MHz) 33.6, 56.0, 105.0, 106.9, 107.2, 107.3, 111.7, 114.1, 117.5, 122.1, 123.6, 124.2, 124.6, 124.9, 126.7, 128.3, 131.5, 135.7, 135.9, 144.4, 145.4, 147.2, 170.3, 170.9.

3-Benzofuran-3-yl-4-(7-hydroxymethyl-1-methyl-1H-indol-3-yl)-pyrrole-2,5-dione (50). (Scheme 11)

7-(tert-Butyldiphenyl-silanyloxymethyl)-1H-indole. To a solution of (1H-indol-7-yl)-methanol (0.95 g, 6.45 mmol) in dichloromethane (36 mL) was added imidazole (0.75 g, 10.97 mmol) and tert-butyldiphenylchlorosilane (2.81 mL, 10.97 mmol) at room temperature and the mixture was stirred for 4 days. The reaction was quenched by addition of methanol. Water was added after 5 min and the mixture was extracted with EtOAc. The organic phase was dried over Na$_2$SO$_4$, evaporated in vacuo and the residue was purified by column chromatography (ethylacetate:hexane; 2:98) to afford the product (2.40 g, 96%) as slightly yellow oil.

7-(tert-Butyldiphenyl-silanyloxymethyl)-1-methyl-1H-indole. The general procedure was followed.

[7-(tert-Butyldiphenyl-silanyloxymethyl)-1-methyl-1H-indol-3-yl]-oxo-acetic acid ethyl ester: The general procedure was followed.

3-Benzofuran-3-yl-4-(7-hydroxymethyl-1-methyl-1H-indol-3-yl)-pyrrole-2,5-dione. $^1$H NMR (CDCl$_3$, 400 MHz) 1.77 (t, J=6.0 Hz, 1H), 4.22 (s, 3H), 4.98 (d, J=6.0 Hz, 2H), 6.72 (t, J=7.6 Hz, 1H), 6.86-6.95 (m, 2H), 6.98 (t, J=7.2 Hz, 2H), 7.19 (dt, J=1.4, 7.5 Hz, 1H), 7.47 (t, J=8.3 Hz, 1H), 7.56 (brs, 1H), 7.72 (s, 1H), 8.09 (s, 1H). $^{13}$C NMR (CDCl$_3$, 100 MHz) 36.7, 63.5, 104.9, 111.4, 111.8, 120.5, 122.3, 122.6, 122.7, 123.5, 124.2, 124.8, 125.1, 125.3, 127.6, 132.0, 135.0, 135.4, 147.2, 154.9, 170.7, 171.2.

3-(6-Hydroxymethyl-benzofuran-3-yl)-4-(7-hydroxymethyl-1-methyl-1H-indol-3-yl)-pyrrole-2,5-dione (51)

$^1$H NMR (DMSO-d6, 400 MHz) 4.18 (s, 3H), 4.52 (d, J=5.6 Hz, 2H), 4.84 (d, J=5.6 Hz, 2H), 5.25 (t, J=6.0 Hz, 1H), 5.36 (t, J=6.0 Hz, 1H), 6.66 (t, J=7.2 Hz, 1H), 6.80 (d, J=8.0 Hz, 1H), 6.90 (s, 2H), 6.97 (d, J=6.8 Hz, 1H), 7.51 (s, 1H), 7.89 (s, 1H), 8.18 (s, 1H), 11.18 (s, 1H). $^{13}$C NMR (DMSO-d6, 100 MHz) 36.6, 61.4, 63.1, 104.1, 109.4, 111.9, 120.2, 120.9, 121.6, 122.0, 122.9, 124.2, 124.6, 126.6, 127.3, 132.8, 135.2, 135.9, 140.4, 147.3, 154.9, 172.3, 172.6.

3-Benzofuran-3-yl-4-(7-methoxymethyl-1-methyl-1H-indol-3-yl)-pyrrole-2,5-dione (52). 7-Methoxymethyl-1-methyl-1H-indole To a solution of (1H-indol-7-yl)-methanol (0.50 g, 3.40 mmol) in dry DMF (6 mL) cooled at 0° C. was added NaH (0.41 g, 10.19 mmol, 55% suspension in mineral oil), followed by methyl iodide (0.50 mL, 8.15 mmol). The reaction mixture was allowed to warm to room temperature and stirred for 1 h. The reaction mixture was poured into ice-water and the solution was extracted with ethyl acetate. The ethyl acetate extract was dried over anhydrous Na$_2$SO$_4$, concentrated in vacuo and purified by column chromatography (ethylacetate:hexane; 1:9) to afford the product (0.53 g, 89%) as slightly yellow oil.

$^1$H NMR (CDCl$_3$, 400 MHz) 3.36 (s, 3H), 4.04 (s, 3H), 4.77 (s, 2H), 6.46 (d, J=4.0 Hz, 1H), 6.95-7.08 (m, 3H), 7.59 (dd, J=2.0, 8.0 Hz, 1H), $^{13}$C NMR (CDCl$_3$, 100 MHz) 35.4, 56.7, 72.7, 100.7, 118.4, 120.2, 121.5, 124.7, 129.9, 130.2, 134.6.

(7-Methoxymethyl-1-methyl-1H-indol-3-yl)-oxo-acetic acid ethyl ester The general procedure was followed.

3-Benzofuran-3-yl-4-(7-methoxymethyl-1-methyl-1H-indol-3-yl)-pyrrole-2,5-dione The general procedure was followed. $^1$H NMR (DMSO-d6, 400 MHz) 3.26 (s, 3H), 4.10 (s, 3H), 4.73 (s, 2H), 6.63 (t, J=7.6 Hz, 1H), 6.83 (d, J=7.6 Hz, 1H), 6.86-6.93 (m, 2H), 6.96 (d, J=7.2 Hz, 1H), 7.20 (dt, J=1.4, 7.2 Hz, 1H), 7.57 (d, J=8.4 Hz, 1H), 7.88 (s, 1H), 8.25 (s, 1H), 11.19 (brs, 1H), $^{13}$C NMR (DMSO-d6, 400 MHz) 35.9, 56.8, 71.6, 103.8, 111.4, 111.6, 119.6, 121.3, 121.7, 121.9, 122.7, 122.8, 124.8, 125.4, 125.5, 127.1, 132.3, 134.9, 135.6, 147.1, 154.2, 171.9, 172.2.

3-Benzofuran-3-yl-4-(7-hydroxy-1-methyl-1H-indol-3-yl)-pyrrole-2,5-dione (53)

The same procedure was followed as described for (30) using 3-benzofuran-3-yl-4-(7-benzyloxy-1-methyl-1H-indol-3-yl)-pyrrole-2,5-dione (6-ing-56). $^1$H NMR (CDCl$_3$, 400 MHz) 4.09 (s, 3H), 6.19 (dd, J=1.1, 7.5 Hz, 1H), 6.4 (m, 2H), 6.98 (m, 2H), 7.22 (m, 1H), 7.59 (d, J=8.2 Hz, 1H), 7.81 (s, 1H), 8.20 (s, 1H); $^{13}$C NMR (CDCl$_3$, 100 MHz) 36.7, 103.9, 107.4, 111.3, 111.6, 112.0, 121.0, 121.5, 121.8, 122.8, 124.7, 125.7, 125.8, 128.1, 132.7, 134.8, 145.0, 146.9, 154.1172.0, 172.3. FAB-HRMS calcd for $C_{21}H_{14}N_2O_4+Na^+$: 381.0846, found: 381.0844.

3-Benzofuran-3-yl-4-(7-benzyloxy-1-methyl-1H-indol-3-yl)-pyrrole-2,5-dione (54)

$^1$H NMR (CDCl$_3$, 400 MHz) 4.09 (s, 3H), 5.15 (s, 2H), 6.52 (d, J=7.8 Hz, 1H), 6.60 (d, J=7.4 Hz, 1H), 6.65 (d, J=7.8

Hz, 1H), 6.92 (t, J=7.6 Hz, 1H), 6.99 (d, J=7.6 Hz, 1H), 7.19 (t, J=7.4 Hz, 1H), 7.33-7.48 (m, 6H), 7.53 (bs, 1H), 7.64 (s, 1H), 8.05 (s, 1H); $^{13}$C NMR (CDCl$_3$, 100 MHz) 37.7, 70.5, 104.7, 104.8, 111.3, 111.8, 114.8, 122.3, 122.7, 124.6, 125.5, 126.7, 127.5, 128.0, 128.3, 128.6, 132.3, 134.7, 136.7, 146.8, 147.0, 154.8, 170.7, 171.2. FAB-HRMS calcd for C$_{28}$H$_{20}$N$_2$O$_4$+Na$^+$: 471.1315; found: 471.1312.

3-(5,6-Difluoro-benzofuran-3-yl)-4-(1-methyl-1H-benzo[g]indol-3-yl)-pyrrole-2,5-dione (55)

$^1$H NMR (CDCl$_3$, 400 MHz) 4.41 (s, 3H), 6.66 (dd, J=7.8, 10.2 Hz, 1H), 6.96 (d, J=8.7 Hz, 1H), 7.18 (d, J=8.7 Hz, 1H), 7.27 (m, 2H), 7.44 (t, J=7.8 Hz, 1H), 7.56 (t, J=7.0 Hz, 1H), 7.70 (s, 1H), 7.82 (d, J=7.8 hz, 1H), 8.17 (s, 1H), 8.47 (d, J=8.4 Hz, 1H). $^{13}$C NMR (CDCl$_3$, 100 MHz) 39.4, 100.4, 100.6, 105.1, 108.9, 109.2, 111.9, 119.9, 120.4, 120.9, 122.3, 122.9, 123.1, 123.5, 124.2, 125.9, 129.2, 130.7, 131.4, 132.5, 133.2, 148.6, 170.4, 170.9.

3-(5-Fluoro-1-methyl-1H-indol-3-yl)-4-(6-hydroxymethyl-benzofuran-3-yl)-1-methyl-pyrrole-2,5-dione (56). (See Scheme 12)

To a solution of 3-(5-fluoro-1-methyl-1H-indol-3-yl)-4-(6-hydroxymethyl-benzofuran-3-yl)-pyrrole-2,5-dione (0.035 g, 0.090 mmol) in dry THF was added sodium hydride (0.005 g, 0.011 mmol, 55% in mineral oil) and methyliodide (0.006 mL, 0.090 mmol) at 0° C. The reaction mixture was allowed to warm to room temperature and stirred for 2 h. The reaction was quenched with ice water, and extracted with EtOAc. The combined organic layers were dried over Na$_2$SO$_4$, evaporated in vacuo and purified by preparative TLC (methanol:dichloromethane; 5:95) to afford the product (0.012 g, 34%) as an orange solid. $^1$H NMR (CDCl$_3$, 400 MHz) 3.19 (s, 3H), 3.86 (s, 3H), 4.71 (s, 2H), 6.62 (dd, J=2.3, 10.0 Hz, 1H), 6.83-6.90 (m, 3H), 7.21 (dd, J=4.3, 8.9 Hz, 1H), 7.51 (s, 1H), 7.81 (s, 1H), 8.11 (s, 1H), $^{13}$C NMR (CDCl$_3$, 100 MHz) 23.9, 33.4, 64.8, 104.7, 106.5, 106.8, 109.6, 110.0, 110.1, 110.6, 110.8, 111.3, 121.4, 121.7, 122.1, 124.5, 126.1, 126.2, 130.8, 133.2, 134.4, 137.8, 147.0, 154.8, 156.6, 158.9, 170.9, 171.3.

Method B: 3-Benzofuran-3-yl-4-(1-methyl-1H-indol-3-yl)-pyrrole-2,5-dione (1)

Benzofuran-3-yl-acetic acid ethyl ester (See, Scheme 1 and Scheme 2)

To a solution of benzofuran-3-one (1.00 g, 7.45 mmol) in toluene (25 mL) was added (carboxymethylene)triphenyl phosphorane (3.92 g, 11.2 mmol), and the mixture was refluxed for 24 h. The reaction mixture was cooled to room temperature and concentrated. The residue was purified by column chromatography (hexane, then ethyl acetate:hexane; 1:3) to give a product (0.89 g, 58%). The spectral data for this compound are identical to that reported in the literature for benzofuran-3-yl-acetic acid ethyl ester (Deshpande, A. R.; Paradkar, M. V. Syn. Commun., 1990, 20, 809).

Benzofuran-3-yl-oxo-acetic acid ethyl ester. To a solution of benzofuran-3-yl-acetic acid ethyl ester (0.79 g, 3.86 mmol) in dioxane (10 mL) was added selenium dioxide (0.85 g, 7.73 mmol). After refluxing for 8 h the mixture was filtered and the filtrate evaporated in vacuo to obtain a residue, which was purified by column chromatography (ethyl acetate:hexane; 1:4) to give a product (0.65 g, 77%). $^1$H NMR (DMSO-d$_6$, 400 MHz) 1.35 (t, J=7.1 Hz, 3H), 4.39 (q, J=7.1 Hz, 2H), 7.43-7.51 (m, 2H), 7.77 (dd, J=1.1, 6.9 Hz, 1H), 8.14 (dd, J=1.1, 6.1 Hz, 1H), 9.15 (s, 1H).

To a suspension of commercially available 2-(1-Methyl-1H-indol-3-yl)-acetamide (54 mg, 0.28 mmol) and benzofuran-3-yl-oxo-acetic acid ethyl ester (63 mg, 0.28 mmol) in dry THF (2.5 mL) at 0° C. was added dropwise a 1.0 M solution of tert-BuOK in THF (1.15 mL), and the reaction mixture was allowed to stir at room temperature overnight. The reaction mixture was quenched with 12 N HCl and diluted with EtOAc. The organic solution was washed with saturated NaHCO$_3$, brine, then dried over Na$_2$SO$_4$, evaporated in vacuo and purified by preparative TLC (ethyl acetate:hexane; 2:3) to afford product 3-benzofuran-3-yl-4-(1-methyl-1H-indol-3-yl)-pyrrole-2,5-dione (1) (44 mg, 44%) as an orange solid.

$^1$H NMR (CDCl$_3$, 400 MHz) 3.89 (s, 3H), 6.17 (t, J=7.3 Hz, 1H), 6.82 (d, J=7.9 Hz, 1H), 6.90 (d, J=4.1 Hz, 2H), 7.08 (t, J=7.1 Hz, 1H), 7.21 (m, 1H), 7.47 (d, J=8.3 Hz, 1H), 7.60 (d, J=8.3 Hz, 1H), 7.99 (s, 1H), 8.27 (s, 1H), 11.19 (s, 1H); $^{13}$C NMR (CDCl$_3$, 75 MHz) 106.2, 107.7, 107.9, 111.5, 111.92, 111.96, 112.0, 112.5, 112.8, 121.1, 121.2, 123.3, 123.7, 125.0, 126.2, 126.4, 129.3, 132.4, 135.8, 148.8, 151.0, 157.5, 159.9, 170.4, 170.8. FAB-HRMS calcd for C$_{21}$H$_{14}$N$_2$O$_3$+Na$^+$: 365.0896; found: 365.0895.

Synthesis of Additional Compounds of this Invention

Compounds of formulas 4A and B are prepared by reduction of the corresponding compounds of formula 3. For example, a two step reduction employing lithium aluminum hydride and hydrogen over Pd/C can be used. See for example Harris, W., Hill, C. H., Keech, E., Malsher, P. Oxidative Cyclisations with Palladium Acetate. A Short Synthesis of Staurosporine Aglycone. Tetrahedron Lett., 34, 8361-8364, (1993). Reduction of a compound of formula 3 will result in a mixture of the corresponding compounds of formula 4a and 4b. The regioisomeric reduction products will be separated using conventional methods.

Certain compounds of formulas 5A and 5B are prepared by O-alkylation of the reduction products of formula 3 (those of formula 4a and 4b, respectively) under basic conditions. See: Bossio, R., Marcaccini, S., Pepino, R., Torroba, T. Studies on isocyanides and related compounds. A facile synthesis of 1-substituted 3-cyano-2-methoxy-3-phenylpyrroles. Heterocycles, 50, 463-467, (1999). For example O-alkylation with diazomethane can be used to obtain compounds of formula 5a and b where R$^4$ is a methyl group.

Certain compounds of formula 6A are prepared, for example by the method of Scheme 14 in which the acid chloride of an appropriately substituted benzofuranylcarboxylic acid is reacted with the anion generated (using, for example, LHMDS, lithium hexamethyl disilazide) from the indole-3-acetic acid ester to form a beta-keto ester. The beta-keto ester is then reacted with hydrazine to form the pyrazolone. The pyrazolone is then treated to protect the oxygen by initial O-alkylation under basic condition to give an alkoxypyrazole, for example using PMBBr (p-methoxybenzyl bromide). A second alkylating agent is used to introduce R$^5$ on the nitrogen at ring position 1, as indicated. The oxygen protecting group is then removed as indicated. Exemplary R$^5$ groups that can be introduced by this method are alkyl (C1-6), hydroxyalkyl, ether (e.g., —CH$_2$—CH$_2$OCH$_3$) and fluoroalkyl groups. Analogous methods will be useful in preparation of the compounds of formula 6B.

Certain compounds of formulas 7A and 7B can be synthesized by methods illustrated in Scheme 15. This reaction scheme makes use of a ring closing metathesis reaction to produce the target compound. For example, the 4-allylated benzofuran is reacted with an indole-3-acetic acid ester. After the formation of the pyrazole ring a terminally unsaturated substituent is introduced on the ring nitrogen, as illustrated. Ring closing methathesis (RMC) followed by double bond reduction give the desired product having an alkenylene linker between the two rings as indicated. Compounds of formula 7B will be prepared by an analogous scheme in which the 4-allylated indole is employed. See: Seganish, W. M., DeShong, P. Preparation and palladium-catalyzed cross-coupling of aryl triethylammonium bis(catechol) silicates with aryl triflates. *J Org Chem,* 69, 1137-1143, (2004); Chen, Q. Y., He, Y., Yang, Z. Y. Palladium-catalyzed cross-coupling reaction of phenyl fluoroalkanesulfonates with allyltributyl-tin. *Youji Huaxue,* 6, 474-476, (1987); Patel, M. V., Bell, R., Majest, S., Henry, R., Kolasa, T. Synthesis of 4,5-Diaryl-1H-pyrazole-3-ol Derivatives as Potential COX-2 Inhibitors. *J. Org. Chem.,* 69, 7058-7065, (2004); and Felpin, F. X., Lebreton, J. Recent Advances in the Total Synthesis of Piperidine and Pyrrolidine Natural Alkaloids with Ring-Closing Metathesis as a Key Step. *Euro. J. Org. Chem.,* 3693-3712, (2003).

Scheme 14

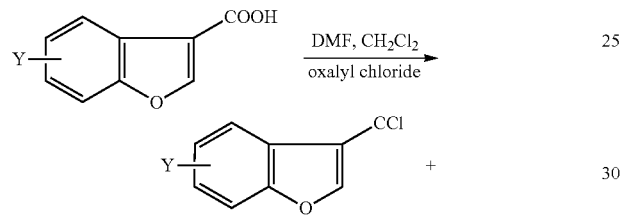

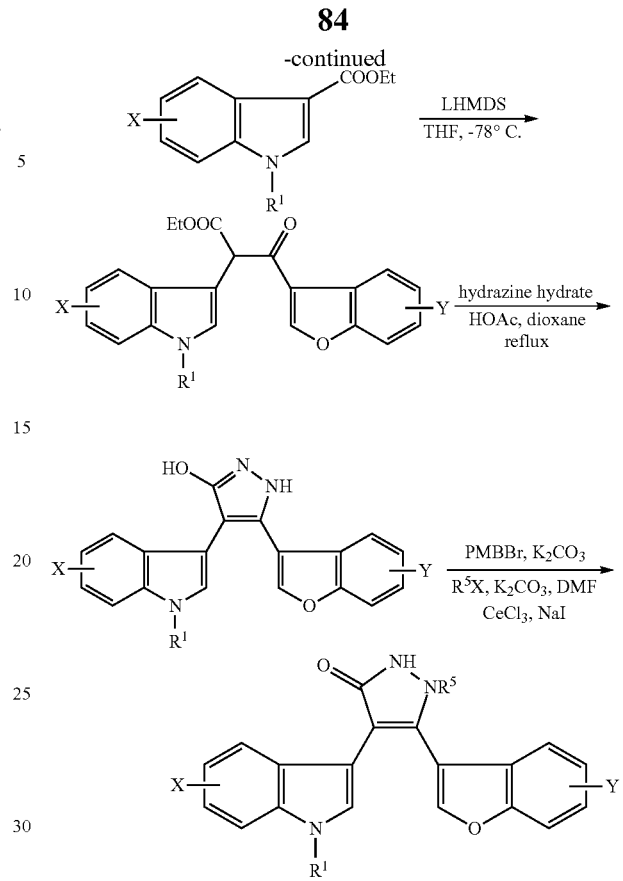

Scheme 15

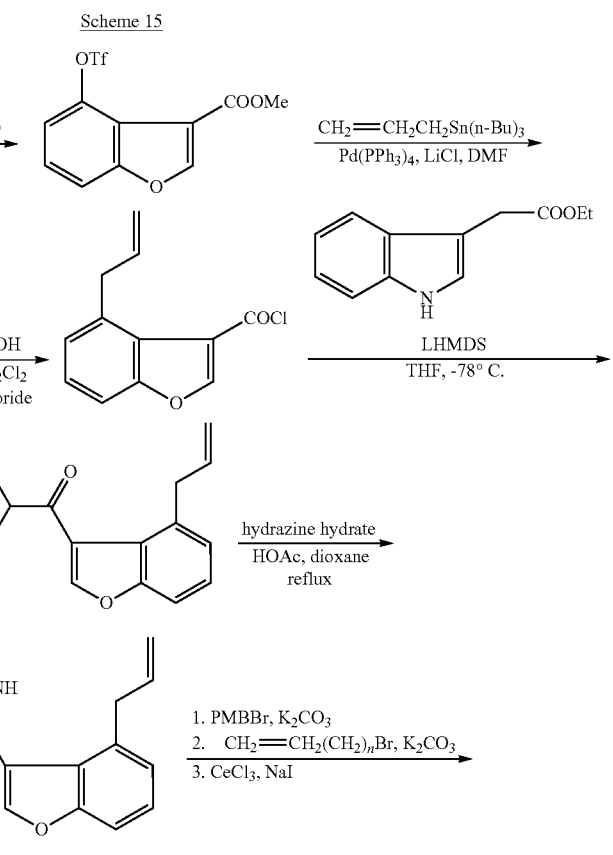

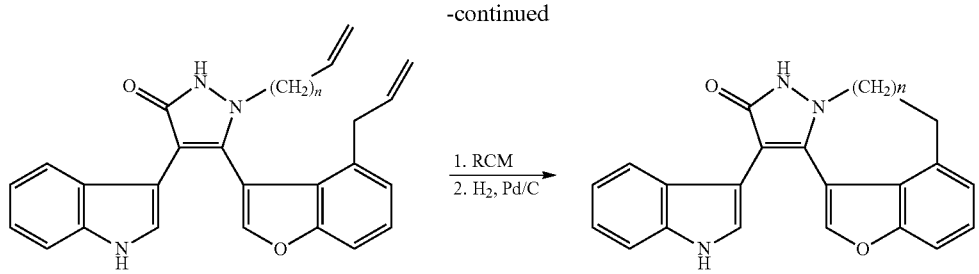

Example 2

Kinase Assays

Kinase assays were performed essentially as described by Welsh and coworkers. (Welsh G. I., Patel J. C., Proud C. G. Anal. Biochem. 1997, 244, 16.) GSK-3 activity was measured as the ability to transfer [$\gamma^{32}$P] from [$\gamma^{32}$P]-ATP to the primed Glycogen Synthase peptide substrate (RRRPAS-VPPSPSLSRHSSHQRR, where the S is the designated primed phosphoserine). The ability of recombinant human $His_6$-GSK-3β ($His_6$-GSK-3β/pET29b, 4-53 nM, or 21 nM, EMD Biosciences) to phosphorylate the pGSM peptide substrate (RRRPASVPPSPSLSRHSSHQRR with the priming phosphoserine underlined, 10 μM final concentration) was assayed in the presence of 10 μM ATP (specific activity 1.3 μCi of [$\gamma$-$^{32}$P] ATP/nM). After incubation for 30 minutes at 30° C., 25 μl of the samples were spotted on 2.5 cm P81 Whatman filters, dried for 5 min and immediately transferred into a beaker containing 0.75% phosphoric acid. The filters were dried and counted in 3 mL ScintiSafe (FisherScientific, Hanover Park, Ill.) cocktail in a Beckman LS6000IC scintillation counter (Beckman Coulter, Fullerton, Calif.).

TABLE 2

GSK-3β inhibition by substituted maleimides[a]

| Compound[b] | $IC_{50}$ (nM) | $K_i$ (nM) | CLogP |
|---|---|---|---|
| 1 | 35.0 ± 9.0 | 23.3 | 4.56 |
| 2 | 670 ± 40 | 446 | 4.21 |
| 3 | 550 ± 20 | 366 | 5.45 |
| 4 | 180 ± 15 | 120 | 4.64 |
| 5 | 360 ± 40 | 240 | 4.21 |
| 6 | 26.0 ± 6.0 | 17.3 | 4.76 |
| 7 | 0.35 ± 0.06 | 0.23 | 3.84 |
| 8 | 23.8 ± 1.7 | 15.8 | 4.26 |
| 9 | 3.5 ± 1.3 | 2.3 | 4.28 |
| 10 | 247 ± 28 | 165 | 6.01 |
| 11 | 59.7 ± 6.57 | 39.8 | 5.73 |
| 12 | 184 ± 31 | 123 | 5.40 |
| 13 | 0.95 ± 0.19 | 0.63 | 4.49 |
| 14 | 870 ± 160 | 580 | 5.07 |
| 15 | 260 ± 32 | 173 | 5.48 |
| 18 | 7162 ± 1196 | 4774 | 7.25 |
| 19 | 7.0 ± 3.0 | 4.6 | 5.45 |
| 20 | 7.5 ± 1.1 | 5.0 | 5.53 |
| 21 | 1.61 ± 0.09 | 1.1 | 4.97 |
| 23 | 25.3 ± 2.4 | 16.9 | 5.74 |
| 24 | 48.3 ± 7.0 | 32.2 | 5.79 |
| 25 | 335 ± 37 | 223 | 7.32 |
| 26 | 88.7 ± 5.6 | 59.1 | 6.24 |
| 27 | 34.5 ± 3.8 | 23 | 5.40 |
| 28 | 15.5 ± 3.5 | 10.3 | 5.73 |
| 29 | 180 ± 11 | 120 | 5.93 |
| 30 | 690 ± 100 | 460 | 4.08 |
| 31 | 500 ± 60 | 333 | 6.35 |
| 32 | 220 ± 30 | 146 | 5.86 |
| 34 | 13.2 ± 3.2 | 8.8 | 3.60 |

TABLE 2-continued

GSK-3β inhibition by substituted maleimides[a]

| Compound[b] | $IC_{50}$ (nM) | $K_i$ (nM) | CLogP |
|---|---|---|---|
| 35 | 131 ± 22 | 87.3 | 5.79 |
| 36 | 9.6 ± 4 | 6.4 | 4.83 |
| 37 | 235 ± 15 | 156 | 5.90 |
| 38 | 16.2 ± 3.9 | 10.7 | 6.37 |
| 39 | 1304 ± 146 | 869 | 4.35 |
| 40 | 708 ± 156 | 472 | 4.82 |
| 41 | 125 ± 35 | 83 | 4.64 |
| 42 | 440 ± 22 | 293 | 5.28 |
| 43 | 223 ± 22 | 148 | 5.81 |
| 44 | 1650 ± 200 | 1100 | 5.80 |
| 45 | 15 ± 3 | 10.0 | 3.79 |
| 46 | 14 ± 3 | 9.3 | 4.28 |
| 47 | 900 ± 80 | 600 | 6.35 |
| 48 | 160 ± 35 | 107 | 6.06 |
| 49 | 831 ± 77 | 554 | 5.60 |
| 50 | 5.4 ± 0.7 | 3.6 | 3.64 |
| 51 | 5.1 ± 1.2 | 3.4 | 3.03 |
| 52 | 0.23 ± 0.04 | 0.15 | 4.07 |
| 53 | 55 ± 8 | 36 | 3.79 |
| 54 | 220 ± 45 | 146 | 6.35 |
| 55 | 314 ± 19 | 209 | 6.14 |
| 56 | 0.35 ± 0.06 | 0.23 | 3.30 |
| 86 | 1.2 ± 0.2 | 0.8 | 3.91 |
| 91 | 23.8 ± 1.7 | 15.8 | 4.26 |
| 92 | 0.73 ± 0.10 | 0.49 | 3.03 |
| 93 | 10.2 ± 3.6 | 6.8 | 4.82 |

[a]The concentration of the inhibitor producing a 50% inhibition of the enzyme ($IC_{50}$) was determined experimentally and used to calculate the apparent equilibrium dissociation constant $K_i$, by using the Chen-Prusoff equation shown here in its simplified form: $K_i = IC_{50}/1 + (S/K_m)$, where S is the substrate (ATP) concentration used in the assays (10 μM) and $K_m$ is the Michaelis constant of the substrate for the enzyme (20 μM for ATP). Partition coefficients (ClogP) were calculated according to the fragment-based program KOWWIN 1.63;
[b]Numbered compounds are identified in Table 1.

Example 3

Kinase Selectivity

Inhibitor 19 (structure in Table 1) shows excellent potency against GSK-3β. This compound was tested against a panel of 20 kinases (Novartis Inc., Switzerland); results are summarized in Table 3 (Note for comparison to Table 2 that $IC_{50}$ are listed in micromolar in Table 3 and nanomolar in Table 2.) Compound 19 (5-ING-135) shows a very significant improvement in selectivity against all the off-target kinases.

TABLE 3

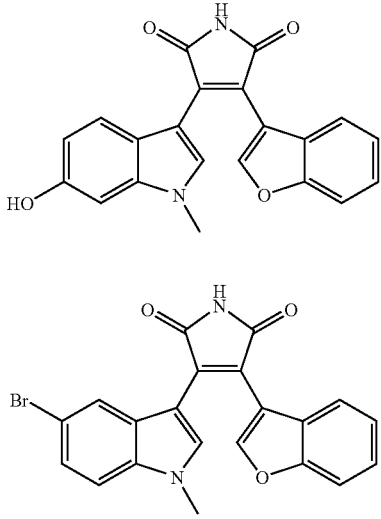

| | 45 IC$_{50}$ (μM) | 19 IC$_{50}$ (μM) | Kinase | 45 IC$_{50}$ (μM) | 19 IC$_{50}$ (μM) | 19 K$_i$ (nM) |
|---|---|---|---|---|---|---|
| Kinase | | | | | | |
| HER-1 | 6.3 | >10 | Axl | >10 | >10 | |
| KDR | 2.2 | >10 | FAK | >10 | >10 | |
| Flt-3 | >10 | >10 | c-Abl | >10 | >10 | |
| IGF-1R | >10 | >10 | c-Abl-T3151 | >10 | >10 | |
| Tek | >10 | >10 | PKA | >10 | >10 | |
| c-src | 4.5 | >10 | CDK2/A | >10 | 3.98 | 189 |
| c-Met | >10 | >10 | PKB | >10 | >10 | |
| Ret | 5.0 | >10 | PDK1 | 0.73 | >10 | |
| JAK-2 | >10 | >10 | b-Raf-V599E | >10 | >10 | |
| EphB4 | >10 | >10 | PKCα | | 61.4 | |
| JNK1 | | >10 | GSK3β Novartis | | 0.200 | 33 |
| FGFR-3-K650E | 7.0 | >10 | GSK3β UIC | | 0.007 (10 μM ATP) | 4.6 ± 2.0 |

Inhibition of Various Kinases by Compound 19

Additional examples of selectivity are illustrated in Table 4.

TABLE 4

Inhibition of Various Kinases (% Inhibition)[a]

| Kinase | Compd 20 10 μM | Compd 20 1 μM | Compd 36 10 μM | Compd 36 1 μM | Compd 10 10 μM | Compd 10 1 μM | Compd 21 10 μM | Compd 21 1 μM | Compd 23 10 μM | Compd 23 1 μM |
|---|---|---|---|---|---|---|---|---|---|---|
| CDK2 | 90 | 76 | 100 | 68 | 35 | 9 | 95 | 62 | 66 | 22 |
| GSK3α | 100 | 58 | 100 | 89 | 95 | 60 | 99 | 62 | 99 | 84 |
| PDK1 | −1 | 7 | 27 | 14 | 6 | −1 | 92 | 80 | 45 | 12 |
| PKCβ2 | 62 | 8 | 74 | 24 | 15 | 2 | 83 | 62 | 25 | 3 |

[a]Compounds are identified in Table 1.

Many GSK-3β inhibitors are also quite potent toward CDK-2 since the ATP binding pockets of these two kinases are very similar. To assess selectivity several compounds of the invention with different structural features were tested against CDK-2/CyclinE. The compounds 13, 15, 22 and 52 were found to be selective toward GSK-3β based on the ratios of IC$_{50}$ measured for these two kinases (Table 5). Compounds 13, 15, 22 and 52 were selected for more extensive evaluation against a panel of CDKs. IC$_{50}$ were determined for inhibition by selected compounds of certain CDKs in Table 6A. The ratio of IC$_{50}$ values for CDK and GSK-3β are provided in Table 6B and illustrate that certain compounds of the invention can exhibit significant selectivity of inhibition of GSK-3β

TABLE 5

CDK-2/CyclinE Inhibition by Substituted Maleimides[a]

| Compound[b] | IC$_{50}$ (nM) CDK-2/cyclinE | IC$_{50}$ Ratio CDK-2/cyclinE GSK-3β |
|---|---|---|
| Staurosporine | 3.8 | 0.8 |
| 1 | 1410 | 40 |
| 7 | 237 | 670 |
| 13 | 11700 | 12300 |
| 15 | 99000 | 410 |
| 20 | 1160 | 150 |
| 22 | 337 | 660 |
| 27 | 1840 | 2.6 |
| 28 | 1070 | 30 |
| 37 | 32000 | 130 |
| 52 | 3880 | 32300 |
| 82 | 149 | 27 |
| 83 | 27 | 5 |

[a]These compounds were tested at Reaction Biology, Inc. (http://www.reactionbiology.com).
[b]Compounds are identified in Table 1.

TABLE 6A

CDK Inhibition by Selected Benzofuran-3-yl-(indol-3-yl)maleimides and Staurosporine[a]

| | IC$_{50}$ (μM) | | | | |
|---|---|---|---|---|---|
| CDK | Staurosporine | 13 | 15 | 22 | 52 |
| CDK-1/cyclinB | 0.0033 | 13.4 | 46.2 | 0.93 | 8.53 |
| CDK-2/cyclinA | 0.0014 | 10.6 | 27.2 | 0.55 | 4.09 |
| CDK-3/cyclinE | 0.0069 | 25.1 | >100 | 1.22 | 17.7 |
| CDK-4/cyclinD1 | 0.0183 | 18.3 | 59.5 | 1.08 | 8.62 |
| CDK-5/P25 | 0.004 | 18.9 | 108 | 1.16 | 12.9 |
| CDK-5/P35 | 0.0038 | 16.1 | 61.6 | 1.13 | 12.7 |
| CDK-6/cyclinD3 | 0.116 | 11.6 | 165 | 0.51 | 8.33 |
| CDK-9/cyclinT1 | 0.0033 | 5.4 | >100 | 1.22 | 16.0 |

[a]These compounds were tested at Reaction Biology, Inc. (http://www.reactionbiology.com).
[b]Compounds identified in Table 1.

TABLE 6B

Ratios of IC$_{50}$ (CDK/GSK-3β) for Selected Compounds[a,b]

| | IC$_{50}$ Ratio (CDK/GSK-3β) | | | |
|---|---|---|---|---|
| Staurosporine | 13 | 15 | 22 | 52 |
| 1.0 | 14000 | 400 | 1800 | 71000 |
| 0.4 | 11100 | 230 | 1000 | 33400 |
| 2.0 | 26400 | >800 | 2300 | 14700 |

TABLE 6B-continued

Ratios of IC$_{50}$ (CDK/GSK-3β) for Selected Compounds[a,b]

| Staurosporine | IC$_{50}$ Ratio (CDK/GSK-3β) | | | |
|---|---|---|---|---|
| | 13 | 15 | 22 | 52 |
| 5.4 | 19200 | 520 | 2100 | 71800 |
| 1.2 | 19800 | 940 | 2200 | 107000 |
| 1.1 | 16900 | 540 | 2200 | 106000 |
| 30 | 12200 | 1400 | 1000 | 69400 |
| 1.0 | 5600 | >800 | 2300 | 13300 |

[a]These compounds were tested at Reaction Biology, Inc. (http://www.reactionbiology.com).
[b]Compounds identified in Table 1.

Example 4

Hyperactivity Animal Model Testing

Hyperactivity models are often used to mimic the mania associated with bipolar disorder. It has been confirmed that the combination of chlorodiazepoxide (CDP) and amphetamine (AMPH) produces an increase in locomotor activity that is greater than the increase produced by amphetamine alone and this hyperactivity can be blocked by the putative mood-stabilizers lithium and lamotrigine (Hanania, T.; Dillon, G. M.; Malekiani, S. A.; Manzano, M. L.; Leahy, E., Soc. Neurosci. Abstr. 2005.) It has also been shown that patients suffering from acute mania have deficits in sensorimotor gating (Perry, W.; Minassian, A.; Feifel, D.; Braff, D. L., Biol Psychiatry 2001, 50, 418-424). Prepulse inhibition is used as a test for sensorimotor gating in mice and it has been shown that LiCl, lamotrigine and valporate also improve sensorimotor gating in mice (Hanania, T.; Dillon, G. M.; Malekiani, S. A.; Manzano, M. L.; Leahy, E., Soc. Neurosci. Abstr. 2005; Brody, S. A.; Geyer, M. A.; Large, C. H., Psychopharmacology 2003, 169, 240-246.)

Certain benzofuran-based ligands of this invention were studied in a novel mouse model of mania that has recently been validated with several clinically effective mood stabilizers. In this study, male 6-week old C57BL/6J mice (received in the male-only colony two weeks prior to the beginning of treatment and housed in groups of 4 per cage) were pretreated with 5-ING-135 (compound 19, Table 1) (50 mg/kg) for 5 min. Mice were then injected with amphetamine (4 mg/kg) or amphetamine (4 mg/kg) and chlordiazepoxide (2.5 mg/kg) and locomotor activity was monitored for 60 min. The open field is a square box surrounded by an array of infra-red beams and their behavior is automatically recorded for 60 minutes in the open field test chamber (10.75"×10.75"×8"H with infra-red (I/R) array, model ENV 510, MED Associates). After this period the animals were returned to their home cages and then to the main colony.

Figure 1B:
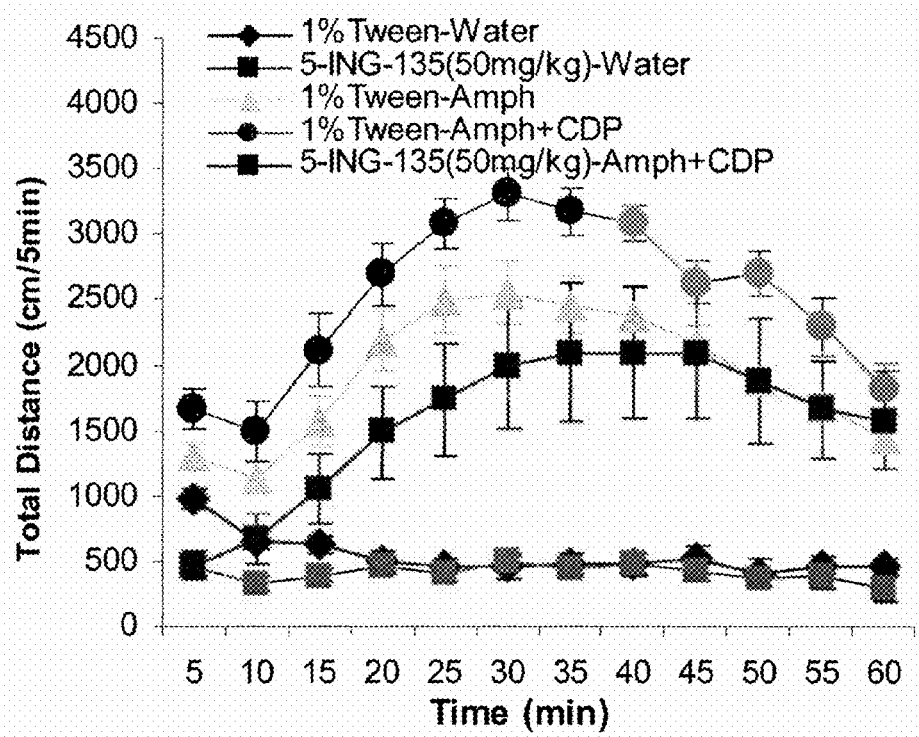
FIG. 1B is a graph illustrating locomotion data of treated mice from FIG. 1A measured in cm over 5 minute intervals for 60 minutes.

FIG. 1A is a graph illustrating inhibition of CDP and amphetamine-induced hyperactivity in C57BL/6J mice by GSK-3β inhibitor 19 (5-ING-135) as assessed by locomotor activity which is measured by total distance from 0 to 60 minutes. Control treatments are as indicated. FIG. 1B illustrates similar locomotion activity data of treated mice measured in cm over 5 minute intervals for 60 minutes.

Pretreatment with 5-ING-135 (19) inhibited the hyperactivity produced by the combination of amphetamine/chlordiazepoxide, with minimal effects on baseline activity. These results indicate that GSK-3 inhibitors have a profile similar to known mood stabilizers like valproate (at 400 mg/kg) in the amphetamine/chlordiazepoxide mania model. In addition, compounds 36 and 46 exhibited inhibition of the hyperactivity produced by the combination of amphetamine/chlordiazepoxide in similar assays.

Example 5

Antiproliferation Assays

The pancreatic cancer cell lines BxPc-3, HupT3, MiaPaCa-2, Panc 04.03, and SU86.86 were obtained from ATCC (Rockville, Md.) and were grown in medium (DMEM or RPMI) containing 10% fetal calf serum and L-glutamine. Pancreatic cancer cells were plated out in duplicate into 6-wells of a 96-well microtiter plate at 2.5–4×10³ cells per well. Four-hours post plating, individual wells were treated with diluent (DMSO) or varying concentrations of commercial compounds, AR-A014418 and SB216763, or the indicated GSK inhibitors of this invention from a concentration of 1 nM to 50 microM. Cytotoxicity was measured at time '0' and 72 hrs post treatment using the colorimetric MTS (3-(4, 5-dimethylthiazol-2-yl )-5-(3-carboxymethoxyphenyl)-2-(4-sulfophenyl)-2H-tetrazolium) assay according to the manufacturer's suggestions (Promega, Madison, Wis.). The IC50s were calculated using XLfit (IDBS Limited, Guildford, UK). Table 5 provides illustrative data for certain compounds of this invention.

TABLE 5

Exemplary Results of Growth Inhibition of Pancreatic Cancer Cells[a,b]

| Compound | MIAPaCa-2 IC$_{50}$ (μM) | BXPC-3 IC$_{50}$ (μM) | HupT3 IC$_{50}$ (μM) |
|---|---|---|---|
| AR-A014418[b] | 25 | | |
| | 29.0 ± 1.7 | 14.0 ± 0.6 | 22.0 ± 2.1 |
| SB216763[c] | 25 | | |
| | 25.0 ± 0.9 | | |
| 1 | 3 | | |
| 5 | 21 | | |
| 19 | 30 | | |
| | 30.0 ± 2.2 | | 43.0 ± 6.3 |
| 36 | >50 | | |
| 4.4 | 21 | | |
| 48 | 80 | | |
| 29 | 28 | 42 | 42 |
| | 28.0 ± 4.1 | 42.0 ± 7.6 | 42.0 ± 8.3 |
| 28 | 8 | 33 | >50 |
| | 8.0 ± 0.6 | 33 ± 4 | >50 |
| 40 | 5 | 1 | 0.6 |
| | 5.0 ± 0.9 | 1.0 ± 0.2 | 0.6 ± 0.5 |
| 55 | 17 | 7 | 6 |
| | 17.0 ± 3.2 | | 6.0 ± 0.7 |
| 49 | 8 | 6 | 6 |
| | 8.0 ± 1.2 | 6.0 ± 0.8 | 6.0 ± 0.5 |
| 26 | 2 | 0.9 | 2 |
| | 2.0 ± 0.2 | 0.9 ± 0.1 | 2.0 ± 0.1 |
| 38 | 34 | >50 | >50 |
| | 34.0 ± 2.2 | >50 | >50 |
| 10 | 0.6 | 0.9 | 0.6 |
| | 0.6 ± 0.1 | 0.9 ± 0.2 | 0.6 ± 0.3 |
| 35 | 14 | >50 | >50 |
| 42 | >50 | | |
| 12 | <1 | | |
| | 3.0 ± 0.4 | 2.0 ± 0.2 | 2.0 ± 0.3 |
| 15 | <1 | | |
| | 3.0 ± 0.2 | 1.0 ± 0.2 | 1.0 ± 0.1 |

[a]Numbered Compounds are identified in Table 1;
[b]Where a second data row is listed, the data does not necessarily represent independent measurements, but provides the data as reported in Gaisina, I.N. et al. (2009) J. Med. Chem. 52(7), 1853-1863;

TABLE 5-continued

Exemplary Results of Growth Inhibition of Pancreatic Cancer Cells[a,b]

| Compound | MIAPaCa-2 IC$_{50}$ (μM) | BXPC-3 IC$_{50}$ (μM) | HupT3 IC$_{50}$ (μM) |
|---|---|---|---|

[c] The structure of compound AR-A014418 is:

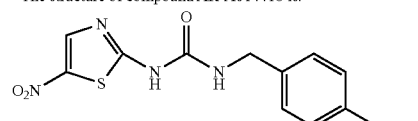

[d] The structure of compound SB216768 is:

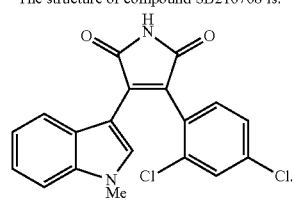

Treatment of pancreatic cell lines BXPC3, HupT3 and MiaPaCa-2 with reference compounds AR-A014418 and SB216768 has been reported to provide a significant decrease in pancreatic cancer cell proliferation [Ougolkov, A. V. et al. (2007) Blood 110: 735-742]. As illustrated in the data of Table 5, certain compounds of this invention, including compounds 1, 40, 55, 49, 26, 38, 10, 12 and 15 show more effective inhibition of pancreatic cancer cell proliferation than these reference compounds. Potent compounds 10, 40 and relatively inactive compound 42 were tested for their ability to inhibit GSK-3β in cell lines by monitoring the level of phosphorylation of glycogen synthase, a substrate of GSK-3β using Western immunoblotting to estimate GSK-3β activity [Gaisina, I. N., et al. 2009) J. Med. Chem. 52(7) 1853-1863.] Compounds 10 and 40 effectively inhibited GSK-3β activity in pancreatic cancer cells leading to decreased proliferation and survival of the cells. In contrast, compound 42 did not affect GSK-3β activity, proliferation or survival of such cells. Treatment with compounds 10 and 40 also resulted in a pronounced decrease in NFκB-mediated expression of XIAP, the most potent antiapoptotic protein, leading to subsequent apoptosis in pancreatic cancer cells.

Similar antiproliferation assays were performed using ovarian cancer cells. Illustrative results of these assays are provided in Table 6. Compound 40 is of particular interest for inhibition of ovarian cancer cell proliferation.

TABLE 6

GSK inhibitors slow ovarian cancer cell proliferation

| Compound | OVCA432 IC$_{50}$ (uM) | SKOV3 IC$_{50}$ (uM) |
|---|---|---|
| 19 | 33.6 | 74.5 |
| 28 | 20.0 | 26.7 |
| 40 | 11.2 | 10.5 |
| 15 | 10.7 | 42.7 |
| 22 | 14.2 | 51.5 |

[a] Compounds are identifed in Table 1

Example 6

Neuroprotection

Tau is a microtubule (MT) binding protein, and its hyperphosphorylation is known to result in MT destabilization, leading to disruption of axonal functions, cytoarchitecture and eventual degeneration of nerve terminals, a condition seen particularly in PD. α-Syn also binds to MTs, where it may be involved in axonal transport, and is causal in the genesis of PD. Published studies in PD cell models (Duka, T.; Sidhu, A. Neurotoxicity Research 2006, 10, 1-10) and MPTP-treated mice (Duka, et al. The FASEB journal 2006, 20, 2302-2312) have established a clear link between α-Syn and p-Tau formation, nigral degeneration and PD.

Figure 2:
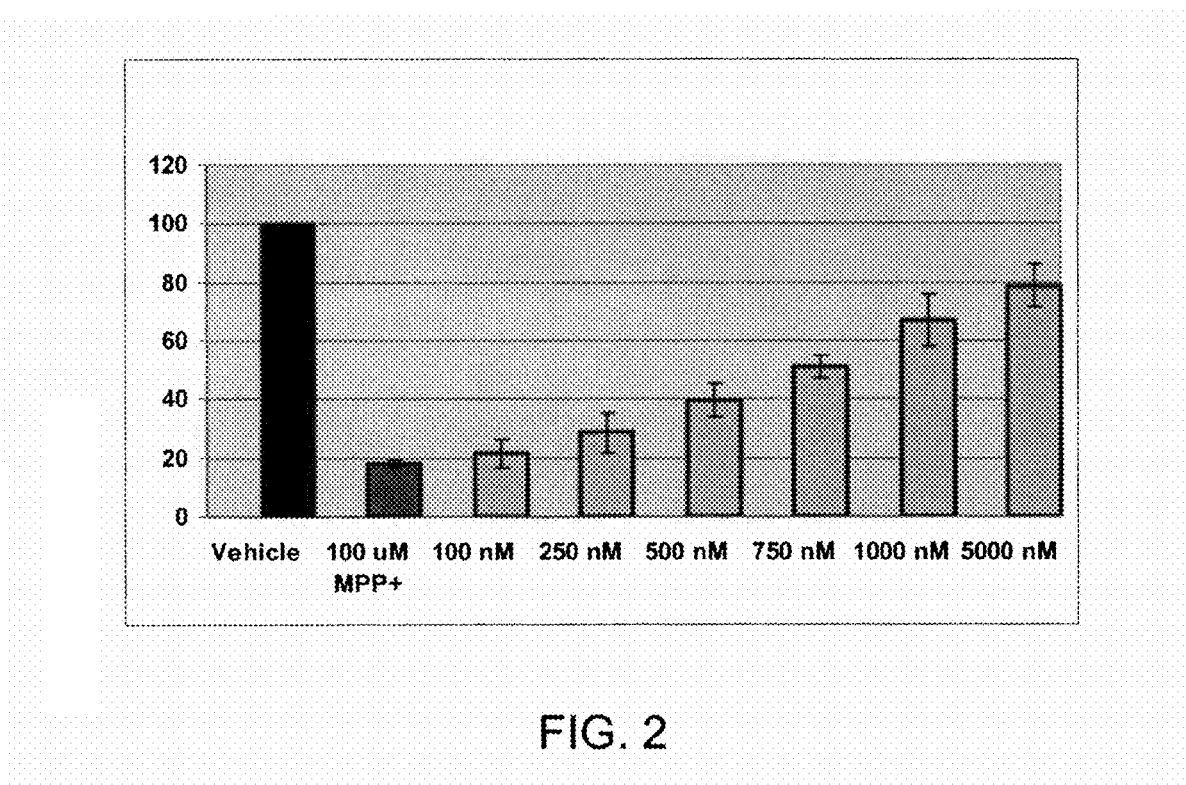
FIG. 2 is a graph of percent cell recovery of α-Syn and hDAT transfected M-17 cells after treatment with GSK-3β Inhibitor compound 15 as a function of increasing amounts of the inhibitor.

GSK-3β inhibitors are examined for their capacity to interfere with two of the regulated processes playing an important role in the MPP+-induced model (MPP+ is N-methyl-4-phenylpyridinium) of neurodegeneration: Tau phosphorylation at the PHF-1 binding site (PHF-Tau; epitope which belongs to AD-like Tau antigenicity) and α-Syn-induced toxicity. Compounds are screened in in vitro assays, where their neuroprotective effects to protect against MPP+-mediated cell death was estimated. The cell assays are conducted as follows: M-17 cancer cells are co-transfected with α-Syn and DAT at a 3:1 DNA mimicking that found in Substantia nigra ratio, as we have described previously (Wersinger, C., et al The FASEB journal 2003, 17, 2151-2153). Cells are treated with MPP+ for 48 h in the absence and presence of increasing amounts of GSK-3β inhibitors [0.1-10,000 nM], and cell death was measured by MTT (Thiazolyl Blue Tetrazolium Bromide) assays. Under these conditions, MPP+ caused ~80% cell death. Exemplary data for compound 15 (Table 1), which illustrate neuroprotection of the cells in the presence of the inhibitor and MPP+, are provided in FIG. 2.

We claim:
1. A compound of formula:

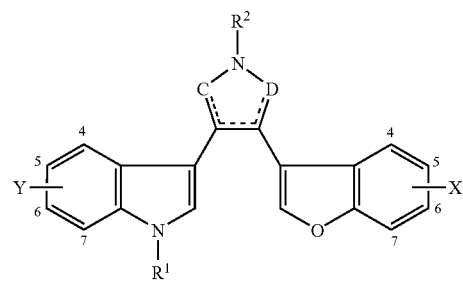

and pharmaceutically acceptable salts, and esters thereof, where:
C and D are selected from:

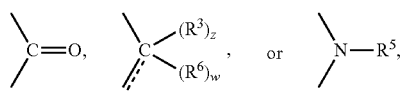

where w and z are 1 or 0, and w and z are not both 0; where doted lines in the central ring above and in the group indicate single or double bonds as appropriate to satisfy valency;

$R^1$ and $R^2$ are independently selected from hydrogen, alkyl, alkenyl, alkynyl, aryl, heterocyclic, arylalkyl, heteroaryl, heteroarylalkyl, alkoxyalkyl, aryloxyalkyl, aminoalkyl, hydroxyalkyl, haloalkyl, thioalkyl, thioalkoxy, ether or thioether;

$R^3$ is selected from alkyl, alkenyl, alkynyl, aryl, heterocyclic, arylalkyl, heteroaryl, heteroarylalkyl, alkoxyalkyl, aryloxyalkyl, aminoalkyl, hydroxyalkyl, haloalkyl, thioalkyl, thioalkoxy, ether or thioether;

$R^5$ is independently selected from hydrogen, alkyl, alkenyl, alkynyl, aryl, heterocyclic, arylalkyl, heteroaryl, heteroarylalkyl, alkoxyalkyl, aryloxyalkyl, aminoalkyl, hydroxyalkyl, haloalkyl, thioalkyl, thioalkoxy, ether or thioether;

$R^6$ takes any value of $R^3$ or —$OR^4$, where $R^4$ is selected from hydrogen, alkyl, alkenyl, alkynyl, aryl, heterocyclic, arylalkyl, heteroaryl, heteroarylalkyl, alkoxyalkyl, aryloxyalkyl, aminoalkyl, hydroxyalkyl, haloalkyl, thioalkyl, thioalkoxy, ether or thioether and X and Y represent one, two, three or four non-hydrogen substituents on the indicated ring, wherein each X and Y is independently selected from halogen, —OH, —CN, —$NO_2$, alkyl, alkenyl, alkynyl, aryl, heterocyclic, heteroaryl, —OR', —$N(R)_2$, —$N(R)_3^+$, —CO—$N(R)_2$, —NHCO—R, —NR'—CO—R, —NR—CO—$N(R)_2$, —CS—$N(R)_2$, —NHCSR, —NR'—CS—R, —NR—CS—$N(R)_2$, amidine, —COH, —CO—R', —$CO_2$H, —$CO_2^-$, —$CO_2$R', —CS—R, —OCO—R, —$SO_2$N$(R)_2$, —NR—$SO_2$R, —$SO_2$—R, —SO—R, —SH or —SR; and X and Y may also be hydrogens except that when $R^1$ is methyl and $R^2$ is hydrogen or methyl at least one of the X or Y substituents is a non-hydrogen substituent;

where each R is independently selected from hydrogen, alkyl, alkenyl, alkynyl, aryl or arylalkyl groups and each R' is independently selected from alkyl, alkenyl, alkynyl, aryl or arylalkyl groups;

wherein two X or two Y, substituted ortho to one another on the indicated ring, optionally can together form a 5- to 8-member carbon ring between the points of attachment of the X's and Y's, which ring may contain one or two heteroatoms;

wherein one of $R^3$, $R^4$, or $R^5$ together with one of X or Y substituted at the 4-position on the indicated ring, can together form a carbon ring which ring may contain one or two heteroatoms, and wherein any carbon atoms of any $R^1$, $R^2$, X, Y, R and R' group are optionally substituted with one or more halogens, —OH, —CN, alkyl, alkenyl, alkynyl, aryl, heterocyclic, heteroaryl, OR', —$N(R)_2$, —$N(R)_3^+$, —CO—$N(R)_2$, —NHCO—R, —NR'—CO—R, —NR—CO—$N(R)_2$, —CS—$N(R)_2$, —NHCSR, —NR'—CS—R, —NR—CS—$N(R)_2$, amidine, —COH, —CO—R', —$CO_2$H, —$CO_2^-$, —$CO_2$R', —CS—R, —OCO—R, —$SO_2N(R)_2$, —NR—$SO_2$R, —$SO_2$—R, —SO—R, —SH or —SR.

2. A compound of claim 1 having the formula:

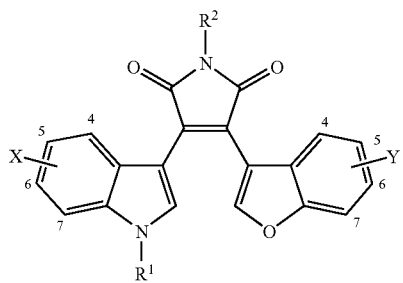

and pharmaceutically acceptable salts, and esters thereof wherein ring numbering for X and Y substituents on the indolyl and benzofuranyl rings are as indicated.

3. A compound of claim 1 wherein at least one of the Y substituents is a non-hydrogen substituent.

4. A compound of claim 1 wherein at least two of the Y substituents are non-hydrogen substituents.

5. A compound of claim 2 wherein $R^1$ is methyl, $R^2$ is hydrogen and X and Y are selected from the group consisting of:
  a. X is 5-F and undefined X are hydrogens, and all Y are hydrogen;
  b. X is 5-F and undefined X are hydrogens; Y is 6-$CH_2$—OH and undefined Y are hydrogens;
  c. X is 5-F and undefined X are hydrogens; Y is 6-OH and undefined Y are hydrogens;
  d. two X are 5-F and 6-Cl, undefined X are hydrogens; Y is 6-$CH_2$—OH and undefined Y are hydrogens;
  e. X is 5-Br and undefined X are hydrogens, and all Y hydrogens;
  f. X is 5-Br and undefined X are hydrogens; Y is 6-$OCH_3$ and all other Y are hydrogens;
  g. X is 5-Br and undefined X are hydrogens; Y is 6-$CH_2$—OH and all other Y are hydrogens;
  h. X is 5-Br and undefined X are hydrogens; Y is 6-$CH_2$—C≡CH and all other Y are hydrogens;
  i. X is 5-I and undefined X are hydrogens and all Y are hydrogens;
  j. X is 5-C≡CH and all other X are hydrogens and all Y are hydrogens;
  k. X is 5-C≡C-cyclopropyl, Y is 5-F and all other X and Y are hydrogens;
  l. X is 6-OH and undefined X and Y are hydrogens,
  m. X is 6-OH, Y is 5-F and all other X and Y are hydrogens; and
  n. X is 7-$CH_2$—OH and all other X and Y are hydrogens.

6. A compound of claim 2 selected from the group consisting of compounds wherein $R^2$ is H and
  all X substituents are H, Y is 5-F, other Y substituents are H and $R^1$ is H;
  all X substituents are H, Y is 5-Br other Y substituents are H, and $R^1$ is $CH_3$;
  all X substituents are H, Y is 7-$OCH_3$ other Y substituents are H, and $R^1$ is $CH_3$;
  X is 5-F, other X substituents are H, all Y substituents are H, and $R^1$ is H;
  X is 5-F, other X substituents are H, all Y substituents are H, and $R^1$ is $CH_3$;
  X is 5-Br, other X substituents are H, all Y substituents are H, and $R^1$ is $CH_3$;
  X is 5-Cl, other X substituents are H, Y is 5-F, other Y substituents are H, and $R^1$ is $CH_3$;
  X is 5-$OCH_3$, other X substituents are H, all Y substituents are H, and $R^1$ is $CH_3$;
  X is 5-OBn, other X substituents are H, all Y substituents are H, and $R^1$ is H;
  X is 5-OBn, other X substituents are H, all Y substituents are H, and $R^1$ is $CH_3$;
  X is 5-OBn, other X substituents are H, all Y substituents are H, and $R^1$ is $(CH_2)_3OH$;
  X is 5-OH, other X substituents are H, all Y substituents are H, and $R^1$ is $CH_3$;
  X is 6-OBn, other X substituents are H, all Y substituents are H, and $R^1$ is $CH_3$;
  X is 6-OH, other X substituents are H, all Y substituents are H, and $R^1$ is $CH_3$;
  X is 6-OBn, other X substituents are H, Y is 5-F, other Y substituents are H, and $R^1$ is $CH_3$;
  X is 6-OH, other X substituents are H, Y is 5-F, other Y substituents are H, and $R^1$ is $CH_3$;
  X is 7-OBn, other X substituents are H, all Y substituents are H, and $R^1$ is $CH_3$;

X is 7-OH, other X substituents are H, all Y substituents are H, and $R^1$ is $CH_3$;

X is 5-C≡CH, other X substituents are H, all Y substituents are H, and $R^1$ is $CH_3$; and X is 5-cyclopropane, other X substituents are H, all Y substituents are H, and $R^1$ is $CH_3$.

7. A compound of claim 2 selected from the group consisting of compounds wherein $R^2$ is H and X is 5-F, other X substituents are H, all Y substituents are H, and $R^1$ is $CH_3$;

X is 5-Br, other X substituents are H, all Y substituents are H, and $R^1$ is $CH_3$;

X is 5-Cl, other X substituents are H, Y is 5-F, other Y substituents are H, and $R^1$ is $CH_3$;

X is 5-$OCH_3$, other X substituents are H, all Y substituents are H, and $R^1$ is $CH_3$;

X is 6-OH, other X substituents are H, all Y substituents are H, and $R^1$ is $CH_3$;

X is 6-OH, other X substituents are H, Y is 5-F, other Y substituents are H, and $R^1$ is $CH_3$;

X is 7-OH, other X substituents are H, all Y substituents are H, and $R^1$ is $CH_3$; and X is 5-C≡CH, other X substituents are H, all Y substituents are H, and $R^1$ is $CH_3$.

8. A compound of claim 2 selected from the group consisting of compounds wherein X is 5-F, other X are H, Y is 6-$CH_2OH$, other Y are H, $R^1$ is $CH_3$, and $R^2$ is H;

X is 5-F, other X are H, Y is 6-$CH_2OCH_3$, other Y are H, $R^1$ is $CH_3$, and $R^2$ is H;

X is 5-F, other X are H, Y is 6-OH, other Y are H, $R^1$ is $CH_3$, and $R^2$ is H;

X is 5-F, 6-I, other X are H, Y is 7-$OCH_3$, other Y are H, $R^1$ is $CH_3$, and $R^2$ is H;

X is 5-F, 6-Br, other X are H, Y is 7-$OCH_3$, other Y are H, $R^1$ is $CH_3$, and $R^2$ is H;

X is 5-F, 6-Cl, other X are H, all Y are H, $R^1$ is $CH_3$, and $R^2$ is H;

X is 5-F, 6-Cl, other X are H, 6-$CH_2OH$, other Y are H, $R^1$ is $CH_3$, and $R^2$ is H;

X is 5-F, and 6-Cl, other X are H, Y is 6-$OCH_3$, other Y are H, $R^1$ is $CH_3$, and $R^2$ is H;

X is 5-F, and 6-Cl, other X are H, Y is 7-$OCH_3$, other Y are H, $R^1$ is $CH_3$, and $R^2$ is H;

X is 5-F, and 6-Cl, other X are H, Y is

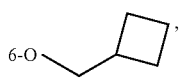

other Y are H, $R^1$ is $CH_3$, and $R^2$ is H;

X is 5-F, and 6-Cl, other X are H, Y is

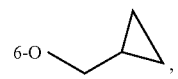

other Y are H, $R^1$ is $CH_3$, and $R^2$ is H;

X is 5-F, and 6-p—Cl—Ph, other X are H, Y is, 7-$OCH_3$, other Y are H, $R^1$ is $CH_3$, and $R^2$ is H;

X is 5-Br, other X are H, Y is 7-$OCH_3$, other Y are H, $R^1$ is $CH_3$, and $R^2$ is H;

X is 5-Br, other X are H, all Y are H, $R^1$ is $(CH_2)_3OH$, and $R^2$ is H;

X is 5-Br, other X are H, Y is 6-$CH_2OH$, other Y are H, $R^1$ is $CH_3$, and $R^2$ is H;

X is 5-Br, other X are H, Y is 6-O—$CH_2$—C≡CH, other Y are H, $R^1$ is $CH_3$, and $R^2$ is H;

X is 5-Br, other X are H, Y is 6-O—$CH_2$—CH=$CH_2$, other Y are H, $R^1$ is $CH_3$, and $R^2$ is H;

X is 5-Br, other X are H, Y is 6-O-(p-$CH_3O$)-Bn, other Y are H, $R^1$ is $CH_3$, and $R^2$ is H;

X is 5-,7-di-Br, other X are H, Y is 6-$OCH_3$, other Y are H, $R^1$ is $CH_3$, and $R^2$ is H;

X is 5-Cl, other X are H, Y is 5-F, other Y are H, $R^1$ is $CH_3$, and $R^2$ is H;

X is 5-I, other X are H, all Y are H, $R^1$ is $CH_3$, and $R^2$ is H;

X is 5-I, other X are H, Y is 5-F, other Y are H, $R^1$ is $CH_3$, and $R^2$ is H;

X is 5-CN, other X are H, all Y are H, $R^1$ is $CH_3$, and $R^2$ is H;

X is 5-CN, other X are H, Y is 6-$CH_2OH$, other Y are H, $R^1$ is $CH_3$, and $R^2$ is H;

X is 5-CN, other X are H, Y is 5,6-di-F, other Y are H, $R^1$ is

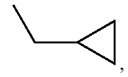

and $R^2$ is H;

X is

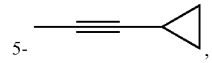

other X are H, Y is 5-F, other Y are H, $R^1$ is $CH_3$, and $R^2$ is H;

X is 5-Morpholine, other X are H, all Y are H, $R^1$ is $CH_3$, and $R^2$ is H;

X is 5,6-Methylene dioxy, other X are H, Y is 5-F, other Y are H, $R^1$ is $CH_3$, and $R^2$ is H;

X is 5-$OCH_3$, other X are H, Y is 6-Cl, H, $R^1$ is $CH_3$ and $R^2$ is H;

X is 5-$OCH_3$, and 6-I, other X are H, all Y are H, $R^1$ is $CH_3$ and $R^2$ is H;

X is 6-$CF_3$, other X are H, Y is 7-$OCH_3$, other Y are H, $R^1$ is $CH_3$ and $R^2$ is H;

X is 7-$CH_2OH$, other X are H, all Y are H, $R^1$ is $CH_3$ and $R^2$ is H;

X is 7-$CH_2OH$, other X are H, Y is 6-$CH_2OH$, other Y are H, $R^1$ is $CH_3$ and $R^2$ is H;

X is 7-$CH_2OMe$, other X are H, all Y are H, $R^1$ is $CH_3$ and $R^2$ is H;

X is 1H-benzo[g], other X are H, Y is 5-,6-di-F, other Y are H, $R^1$ is $CH_3$ and $R^2$ is H; and X is 5-F, other X are H, Y is 6-$CH_2OH$, other Y are H, $R^1$ is $CH_3$ and $R^2$ is H.

9. A compound of claim 2 selected from the group consisting of compounds wherein:

X is 7-$CH_2OH$, other X are H, all Y are H, $R^1$ is $CH_3$ and $R^2$ is H;

X is 5-Br, other X are H, Y is 7-$OCH_3$, other Y are H, $R^1$ is $CH_3$, and $R^2$ is H;

X is 5-Br, other X are H, all Y are H, $R^1$ is $(CH_2)_3OH$, and $R^2$ is H; and X is 5-F, 6-Cl, other X are H, 6-$CH_2OH$, other Y are H, $R^1$ is $CH_3$, and $R^2$ is H.

10. A compound of claim 1 having the formula:

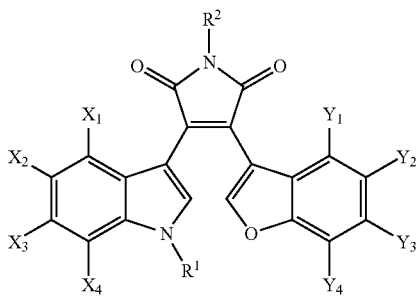

and pharmaceutically acceptable salts, and esters thereof wherein:
- $R^1$ and $R^2$ are independently selected from H or alkyl groups;
- $X_1$ and $Y_1$ are both hydrogens;
- $X_2$, $X_3$ and $X_4$ are selected from hydrogen, halogen, trifluoromethyl, alkoxy or two of $X_2$, $X_3$ or $X_4$ together form a six-member alkyl, alkenyl or aromatic ring in which one or two CH or $CH_2$ groups are optionally replaced with oxygen; and
- $Y_2$, $Y_3$ and $Y_4$, are selected from hydrogen, halogen, or alkoxy groups,
- wherein at least two of the $X_2$-$X_4$ are groups other than hydrogen, except that when $Y_4$ is an alkoxy group, at least one of $X_2$-$X_4$ is a group other than hydrogen; and
- wherein at least one of $Y_2$-$Y_4$ is a group other than hydrogen, except that when two of $X_2$, $X_3$ or $X_4$ are halogens $Y_2$-$Y_4$ can all be hydrogens.

11. A compound of claim 1 having the having the formula:

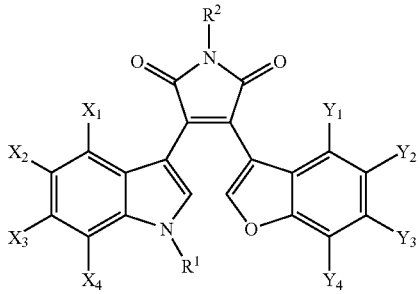

and pharmaceutically acceptable salts, and esters thereof wherein:
- $R^1$ and $R^2$ are independently selected from H, alkyl, aryl, heterocyclic, arylalkyl, heteroaryl, heteroarylalkyl, alkoxyalkyl, aryloxyalkyl, aminoalkyl, thioalkyl, thioalkoxy, ether or thioether;
- $X_4$ is an alkyl group substituted with an OH, an alkyl group substituted with alkoxy, an alkyl group substituted with a carboxylate or an alkyl group substituted with a carboxylate ester group;
- $X_1$-$X_3$ are independently selected from hydrogen, halogen, —OH, —CN, —$NO_2$, alkyl, alkoxy, alkenyl, alkynyl, aryl, alkoxyalkyl, thioalkoxylalkyl, ether, thioether, heterocyclic, heteroaryl, OR', —$N(R)_2$, —$N(R)_3^+$, —CO—$N(R)_2$, —NHCO—R, —NR'—CO—R, —NR—CO—$N(R)_2$, —CS—$N(R)_2$, —NHCSR, —NR'—CS—R, —NR—CS—$N(R)_2$, amidine, —COH, —CO—R', —$CO_2H$, —$CO_2^-$, —$CO_2R'$, —CS—R, —OCO—R, —$SO_2N(R)_2$, —NR—$SO_2R$, —$SO_2$—R, —SO—R, —SH, —SR or two of $X_1$-$X_3$ form a 5- to 8-member ring containing carbon and optionally containing one or two heteroatoms; and
- $Y_1$-$Y_4$ are independently selected from hydrogen, halogen, —OH, —CN, —$NO_2$, alkyl, alkoxy, alkenyl, alkynyl, aryl, alkoxyalkyl, thioalkoxylalkyl, ether, thioether, heterocyclic, heteroaryl, an alkyl group substituted with an OH, an alkyl group substituted with an alkoxy, an alkyl group substituted with a carboxylate, an alkyl group substituted with a carboxylate ester group, OR', —$N(R)_2$, —$N(R)_3^+$, —CO—$N(R)_2$, —NHCO—R, —NR'—CO—R, —NR—CO—$N(R)_2$, —CS—$N(R)_2$, —NHCSR, —NR'—CS—R, —NR—CS—$N(R)_2$, amidine, —COH, —CO—R', —$CO_2H$, —$CO_2^-$, —$CO_2R'$, —CS—R, —OCO—R, —$SO_2N(R)_2$, —NR—$SO_2R$, —$SO_2$—R, —SO—R, —SH or —SR, where R, independently of R', is selected from H, alkyl, alkenyl, alkynyl, aryl and arylalkyl groups and R', independent of R, is selected from alkyl, alkenyl, alkynyl, aryl or arylalkyl groups.

12. The compound of claim 11 wherein $X_1$-$X_3$ are selected from hydrogen, halogen, or alkoxy groups and wherein $Y_1$-$Y_4$ are independently selected from hydrogen, halogen, alkyl, alkoxy, an alkyl group substituted with an OH, an alkyl group substituted with an alkoxy, an alkyl group substituted with a carboxylate, or an alkyl group substituted with a carboxylate ester group.

13. The compound of claim 11 wherein $X_1$-$X_3$ are hydrogens or halogens and $Y_1$-$Y_4$ are hydrogens or halogens.

14. A compound of claim 1 of formula

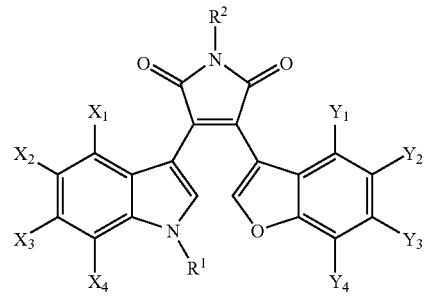

and pharmaceutical acceptable salts, and esters thereof wherein:
- $R^1$ and $R^2$, independently selected from H, alkyl, aryl, heterocyclic, arylalkyl, heteroaryl, heteroarylalkyl, alkoxyalkyl, aryloxyalkyl, aminoalkyl, thioalkyl, thioalkoxy, ether or thioether;
- $Y_3$ is an alkyl group substituted with an OH, an alkyl group substituted with alkoxy, an alkyl group substituted with a carboxylate or an alkyl group substituted with a carboxylate ester group;
- $Y_1$, $Y_2$ and $Y_4$ are independently selected from hydrogens, halogens and alkoxy groups, and
- $X_1$-$X_4$ are independently selected from hydrogen, halogen, an alkoxy group, an alkyl group substituted with an OH, an alkyl group substituted with alkoxy, an alkyl group substituted with a carboxylate or an alkyl group substituted with a carboxylate ester group.

15. A pharmaceutical acceptable composition which comprises a pharmaceutically acceptable carrier and a therapeutically effective amount of a compound of claim 1.

16. A method for treating a protein kinase-related disorder, disease or condition which comprises the step of administering a therapeutically effective amount of a compound of claim 1 to an individual in need of such treatment, wherein the protein kinase-related disorder, disease or condition is bipolar disorder, mania, schizophrenia, stroke, epilepsy, motor neuron diseases, cranial or spinal trauma, multiple sclerosis (MS), Alzheimer's disease, Fragile X syndrome, autism, Huntington's disease, Parkinson's disease, amylotrophic lateral sclerosis (ALS), AIDS-assoClated dementia, diabetes, type II diabetes, cardiomycete hypertrophy, reperfusion/ischemia, allergies, asthma, inflammation, hair loss or baldness.

17. A method for treating cancer which comprises the step of administering a therapeutically effective amount of a compound of claim 1 to an individual in need of such treatment.

18. The method of claim 17 wherein the cancer being treated is cancer or colorectal cancer, pancreatic cancer or ovarian cancer.

19. A method for inhibition proliferation of cancer cells which comprises the step of contacting a cancer cell with an amount of a compound of claim 1 effective for inhibition of proliferation.

20. The method of claim 19 wherein the cancer cell is a pancreatic cancer cell or an ovarian cancer cell.

21. The method of claim 20 wherein the compound is a compound having the formula:

where:
X, Y and $R^2$ are H, and $R^1$ is methyl;
X is 5-fluoro, 6-iodo, Y is 7-methoxy, $R^2$ is H and $R^1$ is methyl;
X is 5-fluoro, 6-chloro, Y is H, $R^2$ is H and $R^1$ is methyl;
X is 5-fluoro, 6-chloro, Y is 7-methoxy, $R^2$ is H and $R^1$ is methyl;
X is 5-,7-dibromo, Y is 7-methoxy, $R^2$ is H and $R^1$ is methyl;
X is 6-trifluoromethyl, Y is 7-methoxy, $R^2$ is H and $R^1$ is methyl;
X is Y is 5-fluoro, $R^2$ is H and $R^1$ is methyl;
X is 5,6-methylene dioxy, Y is 5-fluoro, and $R^2$ is H and $R^1$ is methyl; or
X is 1-H-benzo[g], Y is 5,6-difluoro, $R^2$ is H and $R^1$ is methyl or a pharmaceutically acceptable salt or ester thereof.

22. A compound having formula:

where:
X is H, Y is H, $R^1$ is $CH_3$ and $R^2$ is H;
X is H, Y is 5-F, $R^1$ is H and $R^2$ is H;
X is H, Y is 5-Br, $R^1$ is $CH_3$ and $R^2$ is H;
X is H, Y is 7-$OCH_3$, $R^1$ is $CH_3$ and $R^2$ is H;
X is 5-F, Y is H, $R^1$ is H and $R^2$ is H;
X is 5-F, Y is H, $R^1$ is $CH_3$ and $R^2$ is H;
X is 5-F, Y is 6-$CH_2$—OH, $R^1$ is $CH_3$ and $R^2$ is H;
X is 5-F, Y is 6-$CH_2$—$OCH_3$, $R^1$ is $CH_3$ and $R^2$ is H;
X is 5-F, Y is 6-OH, $R^1$ is $CH_3$ and $R^2$ is H;
X is 5-F, 6-I, Y is 7-$OCH_3$, $R^1$ is $CH_3$ and $R^2$ is H;
X is 5-F, 6-Br, Y is 7-$OCH_3$, $R^1$ is $CH_3$ and $R^2$ is H;
X is 5-F, 6-Cl, Y is H, $R^1$ is $CH_3$ and $R^2$ is H;
X is 5-F, 6-Cl, Y is 6-$CH_2$—OH, $R^1$ is $CH_3$ and $R^2$ is H;
X is 5-F, 6-Cl, Y is 6-$CH_3$, $R^1$ is $CH_3$ and $R^2$ is H;
X is 5-F, 6-Cl, Y is 7-$OCH_3$, $R^1$ is $CH_3$ and $R^2$ is H;
X is 5-F, 6-Cl—, $R^1$ is $CH_3$, $R^2$ is H and Y is X is 5-F, 6-Cl—, $R^1$ is $CH_3$, $R^2$ is H and Y is X is 5-F, 6-p-Cl-Ph, Y is 7-$OCH_3$, $R^1$ is $CH_3$ and $R^2$ is H;
X is 5-Br, Y is H; $R^1$ is $CH_3$ and $R^2$ is H;
X is 5-Br, Y is 7-$OCH_3$; $R^1$ is $CH_3$ and $R^2$ is H;
X is 5-Br, Y is H, $R^1$ is $(CH_2)_3OH$ and $R^2$ is H;
X is 5-Br, Y is 6-$CH_2OH$; $R^1$ is $CH_3$ and $R^2$ is H;
X is 5-Br, Y is 6-O—$CH_2$—CH≡CH, $R^1$ is $CH_3$ and $R^2$ is H;
X is 5-Br, Y is 6-O—$CH_2$—CH=$CH_2$, $R^1$ is $CH_3$ and $R^2$ is H;
X is 5-Br, Y is 6-O—(p—$CH_3O$)—Bn, $R^1$ is $CH_3$ and $R^2$ is H;
X is 5-, 7-di-Br, Y is 7-$OCH_3$, $R^1$ is $CH_3$ and $R^2$ is H;
X is 5-Cl, Y is 5-F, $R^1$ is $CH_3$ and $R^2$ is H;
X is 5-I, Y is H, $R^1$ is $CH_3$ and $R^2$ is H;
X is 5-I, Y is 5-F, $R^1$ is $CH_3$ and $R^2$ is H;
X is 5-OH, Y is H, $R^1$ is $CH_3$ and $R^2$ is H;
X is 5-OBn, Y is H, $R^1$ is $CH_3$ and $R^2$ is H;
X is 5-OBn, Y is H, $R^1$ is $(CH_2)_3OH$ and $R^2$ is H;
X is 5-CN, Y is H, $R^1$ is $CH_3$ and $R^2$ is H;
X is 5-CN, Y is 6-$CH_2OH$, $R^1$ is $CH_3$ and $R^2$ is H;

X is 5-CN, Y is 5,6-di-F, $R^2$ is H and $R^1$ is

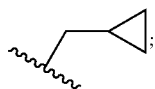

X is 5-C≡CH, Y is H, $R^1$ is $CH_3$ and $R^2$ is H;
X is 5-cyclopropyl, Y is H, $R^1$ is $CH_3$ and $R^2$ is H;
Y is 5-F, $R^1$ is $CH_3$ and $R^2$ is H and X is 5-

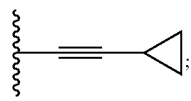

X is 5-Morpholine, Y is H, $R^1$ is $CH_3$ and $R^2$ is H;
X is 5,6-Methylene dioxy, Y is 5-F; $R^1$ is $CH_3$ and $R^2$ is H;
X is 5-$OCH_3$, Y is H, $R^1$ is $CH_3$ and $R^2$ is H;
X is 5-$OCH_3$, 6-Cl, Y is H, $R^1$ is $CH_3$ and $R^2$ is H;
X is 5-$OCH_3$, 6-I, Y is H, $R^1$ is $CH_3$ and $R^2$ is H;
X is 5-OBn, Y is H, $R^1$ is H and $R^2$ is H;
X is 6-OH, Y is H, $R^1$ is $CH_3$ and $R^2$ is H;
X is 6-OH, Y is 5-F, $R^1$ is $CH_3$ and $R^2$ is H;
X is 6-OBn, Y is H, $R^1$ is $CH_3$ and $R^2$ is H;
X is 6-OBn, Y is 5-F, $R^1$ is $CH_3$ and $R^2$ is H;
X is 6-$CF_3$, Y is 7-$OCH_3$, $R^1$ is $CH_3$ and $R^2$ is H;
X is 7-$CH_2OH$, Y is H, $R^1$ is $CH_3$ and $R^2$ is H;
X is 7-$CH_2OH$, Y is 6-$CH_2OH$, $R^1$ is $CH_3$ and $R^2$ is H;
X is 7-$CH_2OCH_3$, Y is H, $R^1$ is $CH_3$ and $R^2$ is H;
X is 7-OH, Y is H, $R^1$ is $CH_3$ and $R^2$ is H;
X is 7-OBn, Y is H, $R^1$ is $CH_3$ and $R^2$ is H;
X is 1H-benzo[g], Y is 5-,6-di-F, $R^1$ is $CH_3$ and $R^2$ is H;
X is 5-F, Y is 6-$CH_2OH$, $R^1$ is $CH_3$ and $R^2$ is $CH_3$;
X is 5-F, 6-CN, Y is 5-F, $R^1$ is $CH_3$ and $R^2$ is H;
X is 5-F, 6-$CF_3$, Y is 5-F, $R^1$ is $CH_3$ and $R^2$ is H;
X is 5-F, 6-CH=$CH_2$, Y is 5-F, $R^1$ is $CH_3$ and $R^2$ is H;
X is 5-F, 6-C≡CH, Y is 5-F, $R^1$ is $CH_3$ and $R^2$ is H;
X is 5-F, 6-OH, Y is 5-F, $R^1$ is $CH_3$ and $R^2$ is H;
X is 5-F, 6-$SCH_3$, Y is 5-F, $R^1$ is $CH_3$ and $R^2$ is H;
X is 5-F, 6-$SCH_2CH_3$, Y is 5-F, $R^1$ is $CH_3$ and $R^2$ is H;
X is 5, 6-di-Cl, Y is 5-F, $R^1$ is $CH_3$ and $R^2$ is H;
X is 5-Cl, 6-OH, Y is 5-F, $R^1$ is $CH_3$ and $R^2$ is H;
X is 5-$CF_3$, Y is 5-F, $R^1$ is $CH_3$ and $R^2$ is H;
X is 5-CN, Y is 5-F, $R^1$ is $CH_3$ and $R^2$ is H;
X is 5-$OCH_3$, 6-Cl, Y is 5-F, $R^1$ is $CH_3$ and $R^2$ is H;
X is 5-$OCH_3$, 6-Br, Y is 5-F, $R^1$ is $CH_3$ and $R^2$ is H;
X is 5-CN, Y is 5-F, $R^1$ is $CH_3$ and $R^2$ is H;
X is 5-$CF_3$, Y is 6-$OCH_3$, $R^1$ is $CH_3$ and $R^2$ is H;
X is 5-CN, Y is 6-$OCH_3$, $R^1$ is $CH_3$ and $R^2$ is H;
X is 6-$CHF_2$, Y is 7-$OCH_3$, $R^1$ is $CH_3$ and $R^2$ is H;
X is 5-$CF_3$, Y is 7-$OCH_3$, $R^1$ is $CH_3$ and $R^2$ is H;
X is 5-Cl, 6-OH, Y is 6-$CH_2OH$, $R^1$ is $CH_3$ and $R^2$ is H;
X is 5-F, 6-$CH_3$, Y is 6-$CH_2OH$, $R^1$ is $CH_3$ and $R^2$ is H;
X is 5-F, 6-Cl, Y is 6-$CH_2OCH_3$, $R^1$ is $CH_3$ and $R^2$ is H;
X is 5-CN, Y is 6-$CH_2CH_2OH$, $R^1$ is $CH_3$ and $R^2$ is H;
X is 5-Br, Y is 6-$CH_2CH_2CO_2H$, $R^1$ is $CH_3$ and $R^2$ is H;
X is 6-$CH_2OH$, Y is H, $R^1$ is $CH_3$ and $R^2$ is H;
X is 6-$CH_2OCH_3$, Y is H, $R^1$ is $CH_3$ and $R^2$ is H;
X is 7-$CH_2OH$, Y is H, $R^1$ is $CH_3$ and $R^2$ is H;
X is 7-$CH_2OH$, Y is 6-$CH_2OH$, $R^1$ is $CH_3$ and $R^2$ is H;
X is 7-$CH_2OCH_3$, Y is H, $R^1$ is $CH_3$ and $R^2$ is H;
X is 7-$CH_2CH_2OH$, Y is H, $R^1$ is $CH_3$ and $R^2$ is H;
X is 7-$CH_2CH_2CO_2H$, Y is H, $R^1$ is $CH_3$ and $R^2$ is H;
X is 7-$CH(CH_3)=CH_2$, Y is H, $R^1$ is $CH_3$ and $R^2$ is H;
X is 7-$C(CH_3)_2OCH_3$, Y is H, $R^1$ is $CH_3$ and $R^2$ is H;
X is 5-$CF_3$, Y is 5-F, $R^1$ is $CH_2CF_3$ and $R^2$ is H;
X is H, Y is 5-F, $R^1$ is $CH_2CF_3$ and $R^2$ is H;
X is 5-F, Y is 6-$CH_2OH$, $R^1$ is $CH_3$ and $R^2$ is H;
X is 7-$CH_2OCH_3$; Y is 6-$CH_2OH$, $R^1$ is $CH_3$ and $R^2$ is H;
X is 7-$CH_2CH_2OC_2H_5$; Y is H, $R^1$ is $CH_3$ and $R^2$ is H; or a pharmaceutically acceptable salt thereof.

* * * * *

UNITED STATES PATENT AND TRADEMARK OFFICE
CERTIFICATE OF CORRECTION

PATENT NO. : 8,207,216 B2
APPLICATION NO. : 12/488433
DATED : June 26, 2012
INVENTOR(S) : Alan P. Kozikowski and Irina Gaysina It is certified that error appears in the above-identified patent and that said Letters Patent is hereby corrected as shown below:

Title page (56) References Cited, line 11, replace "Beat et al." with --Bear et al.--.

In Claim 14, line 4 (Col. 98, line 50), replace "and $R^2$," with --and $R^2$ are--.

In Claim 15, line 1 (Col. 98, line 65), replace "pharmaceutical" with --pharmaceutically--.

Signed and Sealed this
Fourth Day of September, 2012

David J. Kappos
*Director of the United States Patent and Trademark Office*